United States Patent
Scott et al.

(10) Patent No.: US 10,485,704 B2
(45) Date of Patent: Nov. 26, 2019

(54) CORNEAL TOPOGRAPHY MEASUREMENT AND ALIGNMENT OF CORNEAL SURGICAL PROCEDURES

(71) Applicant: OptiMedica Corporation, Santa Ana, CA (US)

(72) Inventors: David D. Scott, Oakland, CA (US); Javier Gonzalez, Palo Alto, CA (US); David Dewey, Sunnyvale, CA (US); Noah Bareket, Sunnyvale, CA (US); Georg Schuele, Menlo Park, CA (US)

(73) Assignee: OPTIMEDICA CORPORATION, Santa Ana, CA (US)

(*) Notice: Subject to any disclaimer, the term of this patent is extended or adjusted under 35 U.S.C. 154(b) by 1207 days.

(21) Appl. No.: 14/256,307

(22) Filed: Apr. 18, 2014

(65) Prior Publication Data

US 2015/0018674 A1    Jan. 15, 2015

Related U.S. Application Data

(60) Provisional application No. 61/813,613, filed on Apr. 18, 2013, provisional application No. 61/873,071, filed on Sep. 3, 2013.

(51) Int. Cl.
*A61F 9/008* (2006.01)
*A61B 3/107* (2006.01)
(Continued)

(52) U.S. Cl.
CPC .......... *A61F 9/00825* (2013.01); *A61B 3/10* (2013.01); *A61B 3/107* (2013.01); *A61B 5/0073* (2013.01);
(Continued)

(58) Field of Classification Search
CPC ......... A61B 3/107; A61B 3/10; A61B 5/0073; A61F 2009/0087; A61F 9/00825–00829;
(Continued)

(56) References Cited

U.S. PATENT DOCUMENTS

| 4,692,003 A | * | 9/1987 | Adachi | .................. | A61B 3/107 351/212 |
| 5,092,863 A | | 3/1992 | Schanzlin | | |

(Continued)

FOREIGN PATENT DOCUMENTS

| JP | 2006522629 A | 10/2006 |
| JP | 2011502585 A | 1/2011 |

(Continued)

OTHER PUBLICATIONS

International Search Report and Written Opinion for Application No. PCT/US2014/020343, dated May 15, 2014, 10 pages.

(Continued)

*Primary Examiner* — Bo Joseph Peng
(74) *Attorney, Agent, or Firm* — Johnson & Johnson Surgical Vision, Inc.

(57) ABSTRACT

Methods and apparatus are configures to measure an eye without contacting the eye with a patient interface, and these measurements are used to determine alignment and placement of the incisions when the patient interface contacts the eye. The pre-contact locations of one or more structures of the eye can be used to determine corresponding post-contact locations of the one or more optical structures of the eye when the patient interface has contacted the eye, such that the laser incisions are placed at locations that promote normal vision of the eye. The incisions are positioned in relation to the pre-contact optical structures of the eye, such as an astigmatic treatment axis, nodal points of the eye, and visual axis of the eye.

19 Claims, 29 Drawing Sheets

(51) Int. Cl.
*A61B 3/10* (2006.01)
*A61B 5/00* (2006.01)

(52) U.S. Cl.
CPC ...... *A61F 9/00827* (2013.01); *A61F 9/00829* (2013.01); *A61F 2009/0087* (2013.01); *A61F 2009/0088* (2013.01); *A61F 2009/00846* (2013.01); *A61F 2009/00853* (2013.01); *A61F 2009/00872* (2013.01); *A61F 2009/00882* (2013.01); *A61F 2009/00887* (2013.01); *A61F 2009/00889* (2013.01)

(58) Field of Classification Search
CPC .............. A61F 9/00827; A61F 9/00829; A61F 2009/00846; A61F 2009/00853; A61F 2009/00872; A61F 2009/00882; A61F 2009/00887; A61F 2009/00889; A61F 2009/0088
See application file for complete search history.

(56) References Cited

U.S. PATENT DOCUMENTS

| | | | |
|---|---|---|---|
| 5,634,920 A * | 6/1997 | Hohla | A61F 9/008 606/10 |
| 5,720,894 A | 2/1998 | Neev et al. | |
| 5,957,915 A | 9/1999 | Trost | |
| 5,984,916 A | 11/1999 | Lai | |
| 6,019,472 A | 2/2000 | Koester et al. | |
| 6,090,100 A * | 7/2000 | Hohla | A61F 9/008 606/10 |
| 6,454,761 B1 | 9/2002 | Freedman | |
| 7,655,002 B2 | 2/2010 | Myers et al. | |
| 7,717,907 B2 | 5/2010 | Ruiz et al. | |
| 8,262,646 B2 | 9/2012 | Frey et al. | |
| 8,350,183 B2 | 1/2013 | Vogel et al. | |
| 8,382,745 B2 | 2/2013 | Naranjo-Tackman et al. | |
| 8,414,564 B2 | 4/2013 | Goldshleger et al. | |
| 2004/0254568 A1* | 12/2004 | Rathjen | A61F 9/00827 606/4 |
| 2006/0116765 A1 | 6/2006 | Blake et al. | |
| 2007/0173794 A1* | 7/2007 | Frey | A61F 9/008 606/5 |
| 2007/0216867 A1* | 9/2007 | Campbell | A61F 9/00806 351/246 |
| 2009/0198326 A1 | 8/2009 | Zhou et al. | |
| 2009/0251664 A1 | 10/2009 | Norrby et al. | |
| 2010/0022995 A1* | 1/2010 | Frey | A61F 9/008 606/4 |
| 2011/0105943 A1 | 5/2011 | De et al. | |
| 2011/0190740 A1* | 8/2011 | Frey | A61F 9/00825 606/5 |
| 2011/0202046 A1 | 8/2011 | Angeley et al. | |
| 2011/0319873 A1 | 12/2011 | Raksi et al. | |
| 2011/0319875 A1 | 12/2011 | Loesel et al. | |
| 2013/0041354 A1 | 2/2013 | Brownell et al. | |

FOREIGN PATENT DOCUMENTS

| | | |
|---|---|---|
| JP | 2011507572 A | 3/2011 |
| JP | 2013248303 A | 12/2013 |
| WO | 03000154 A2 | 1/2003 |
| WO | 03022137 A2 | 3/2003 |
| WO | 2008065362 A1 | 6/2008 |
| WO | 2009142961 A1 | 11/2009 |

OTHER PUBLICATIONS

International Search Report for Application No. PCT/US2014/034628, dated Oct. 30, 2014, 7 pages.

\* cited by examiner

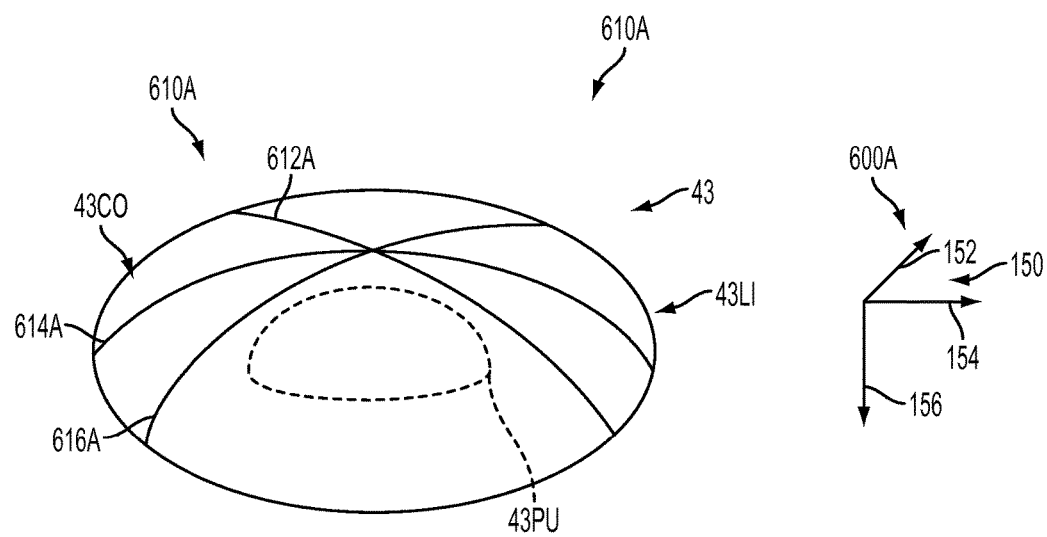
FIG. 6A1
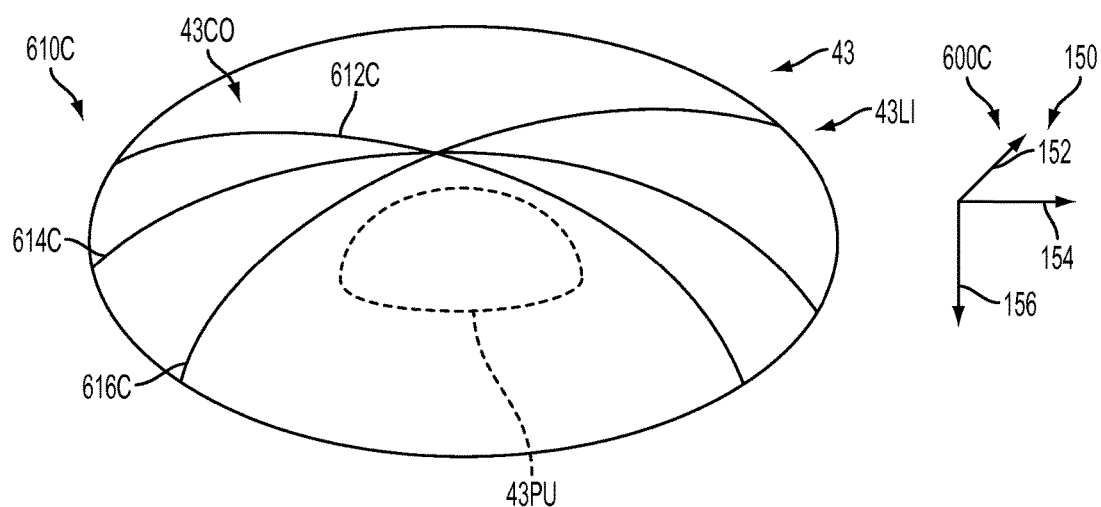
FIG. 6C1

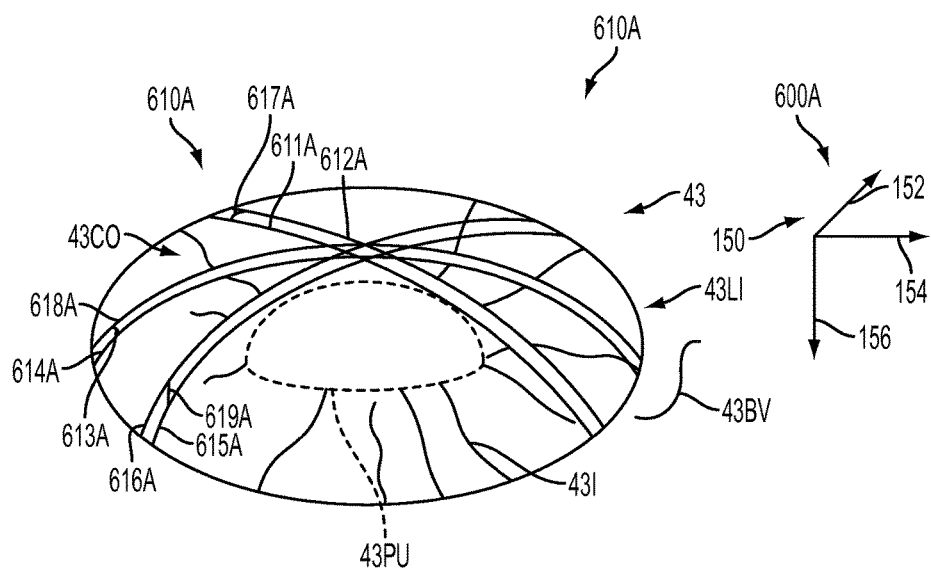
FIG. 6A2
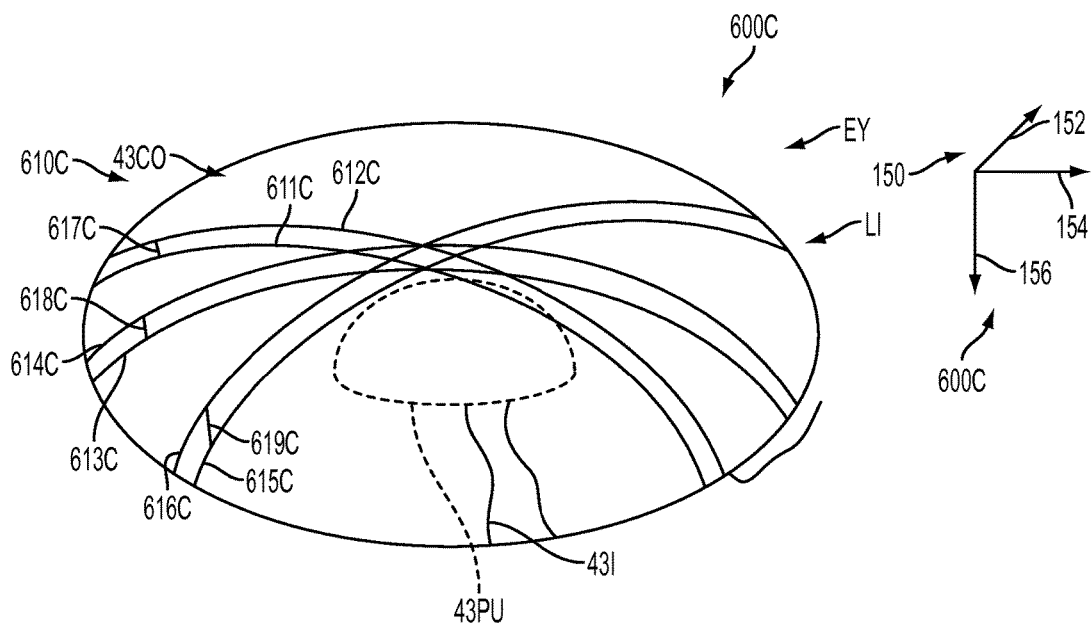
FIG. 6C2

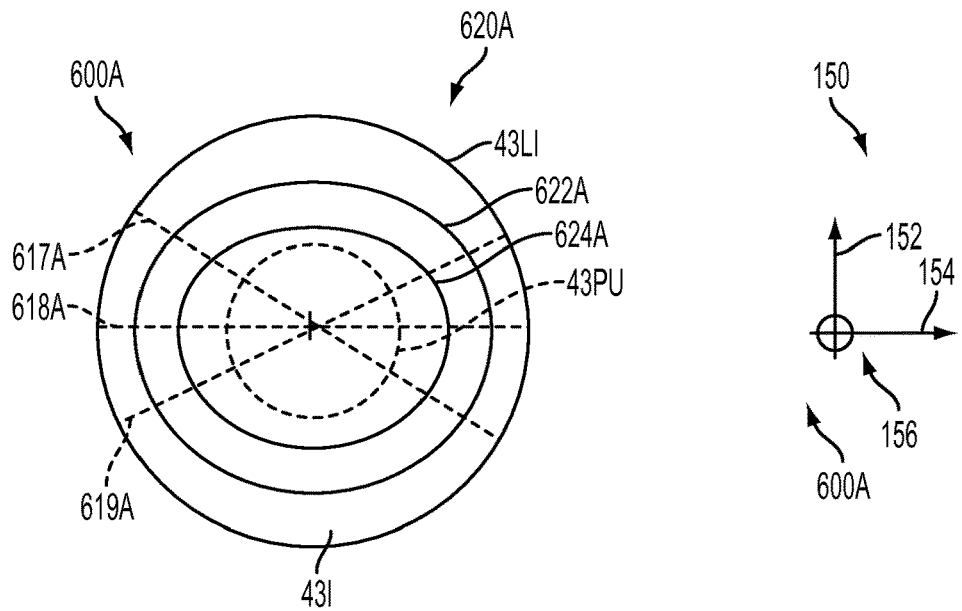
FIG. 6A3
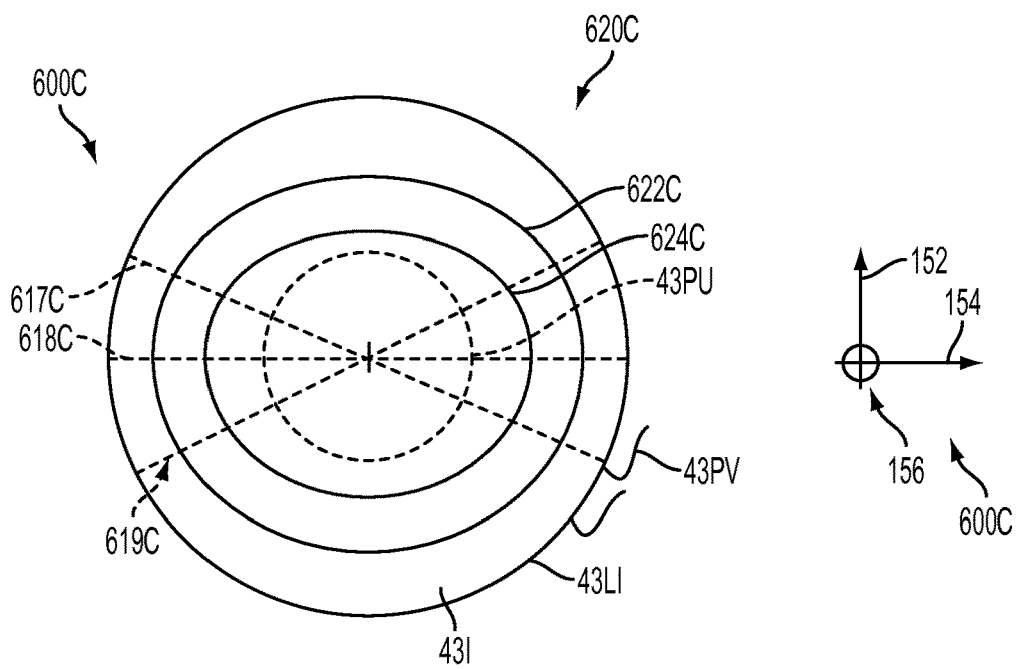
FIG. 6C3

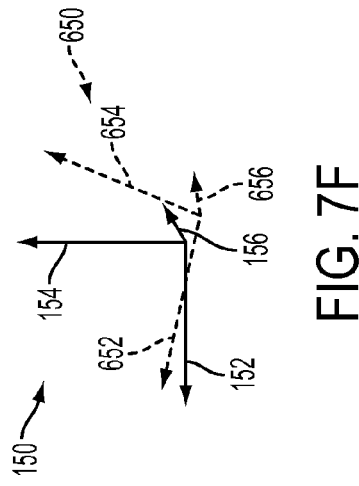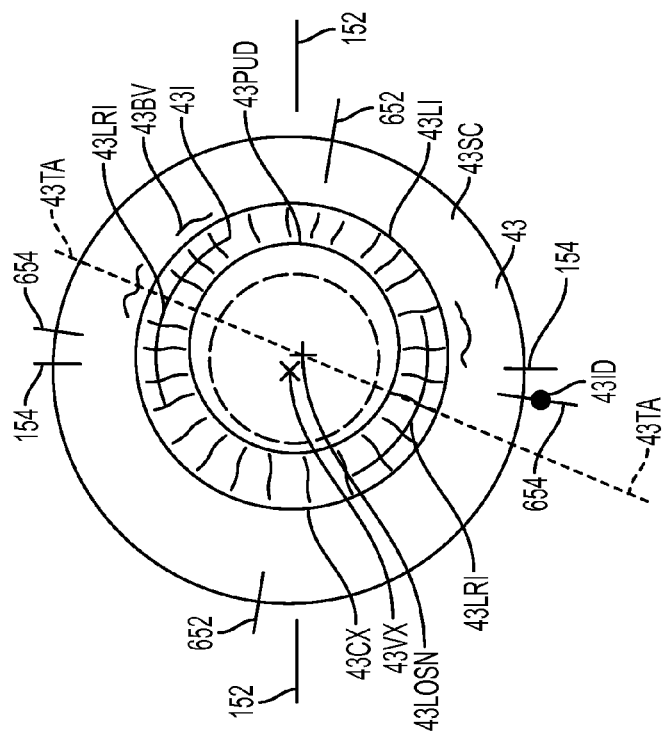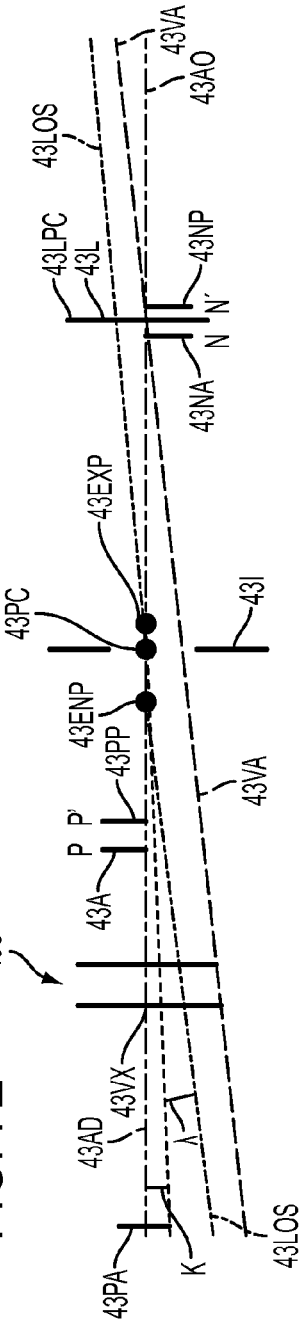

CORNEAL TOPOGRAPHY MEASUREMENT AND ALIGNMENT OF CORNEAL SURGICAL PROCEDURES

CROSS-REFERENCE

This application claims priority to U.S. provisional application No. 61/813,613, filed on Apr. 18, 2013, entitled "CORNEAL TOPOGRAPHY MEASUREMENT AND ALIGNMENT OF CORNEAL SURGICAL PROCEDURES," and U.S. provisional application No. 61/873,071, filed on Sep. 3, 2013, entitled "CORNEAL TOPOGRAPHY MEASUREMENT AND ALIGNMENT OF REFRACTIVE SURGICAL PROCEDURES," the entire contents of which are incorporated herein by reference.

The subject matter of the present disclosure is related to the following patent applications: U.S. application Ser. No. 12/048,182, filed 3 Mar. 2008, entitled "METHOD AND APPARATUS FOR CREATING INCISIONS TO IMPROVE INTRAOCULAR LENS PLACEMENT"; U.S. application Ser. No. 12/048,186, filed 13 Mar. 2008, entitled "METHOD AND APPARATUS FOR CREATING OCULAR SURGICAL AND RELAXING INCISIONS"; U.S. App. Ser. No. 61/722,064, filed 2 Nov. 2012, entitled "LASER EYE SURGERY SYSTEM CALIBRATION"; U.S. App. Ser. No. 61/813,613, filed Apr. 18, 2013, entitled "CORNEAL TOPOGRAPHY MEASUREMENT AND ALIGNMENT OF CORNEAL SURGICAL PROCEDURES"; U.S. Pat. App. Ser. No. 61/788,201, filed Mar. 15, 2013, entitled "MICROFEMTOTOMY METHODS AND SYSTEMS"; U.S. Ser. No. 61/813,172, filed Apr. 17, 2013, entitled "LASER FIDUCIALS FOR ALIGNMENT IN CATARACT SURGERY,"; the entire disclosures of which are incorporated herein by reference and suitable for combination in accordance with embodiments disclosed herein.

BACKGROUND

The present disclosure relates generally to photodisruption induced by a pulsed laser beam and the location of the photodisruption so as to treat a material, such as a tissue of an eye. Although specific reference is made to cutting tissue for surgery such as eye surgery, embodiments as described herein can be used in many ways with many materials to treat one or more of many materials, such as cutting of optically transparent materials.

Cutting of materials can be done mechanically with chisels, knives, scalpels and other tools such as surgical tools. However, prior methods and apparatus of cutting can be less than desirable and provide less than ideal results in at least some instances. For example, at least some prior methods and apparatus for cutting materials such as tissue may provide a somewhat rougher surface than would be ideal. Pulsed lasers can be used to cut one or more of many materials and have been used for laser surgery to cut tissue.

Examples of surgically tissue cutting include cutting the cornea and crystalline lens of the eye. The lens of the eye can be cut to correct a defect of the lens, for example to remove a cataract, and the tissues of the eye can be cut to access the lens. For example the cornea can be to access the cataractous lens. The cornea can be cut in order to correct a refractive error of the eye, for example with laser assisted in situ keratomileusis (hereinafter "LASIK") or photorefractive keratectomy (hereinafter "PRK"), for example.

Many patients may have visual errors associated with the refractive properties of the eye such as nearsightedness, farsightedness and astigmatism. Astigmatism may occur when the corneal curvature is unequal in two or more directions. Nearsightedness can occur when light focuses before the retina, and farsightedness can occur with light refracted to a focus behind the retina. There are numerous prior surgical approaches for reshaping the cornea, including laser assisted in situ keratomileusis (hereinafter "LASIK"), all laser LASIK, femto LASIK, corneaplasty, astigmatic keratotomy, corneal relaxing incision (hereinafter "CRI"), Limbal Relaxing Incision (hereinafter "LRI"), photorefractive keratectomy (hereinafter "PRK") and Small Incision Lens Extraction (hereinafter "SMILE"). Astigmatic Keratotomy, Corneal Relaxing Incision (CRI), and Limbal Relaxing Incision (LRI), corneal incisions are made in a well-defined manner and depth to allow the cornea to change shape to become more spherical.

Cataract extraction is a frequently performed surgical procedure. A cataract is formed by opacification of the crystalline lens of the eye. The cataract scatters light passing through the lens and may perceptibly degrade vision. A cataract can vary in degree from slight to complete opacity. Early in the development of an age-related cataract the power of the lens may increase, causing near-sightedness (myopia). Gradual yellowing and opacification of the lens may reduce the perception of blue colors as those shorter wavelengths are more strongly absorbed and scattered within the cataractous crystalline lens. Cataract formation may often progresses slowly resulting in progressive vision loss.

A cataract treatment may involve replacing the opaque crystalline lens with an artificial intraocular lens (IOL), and an estimated 15 million cataract surgeries per year are performed worldwide. Cataract surgery can be performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small round hole can be formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye.

Prior short pulse laser systems have been used to cut tissue, and have been used to treat many patients. However, the prior short pulse systems may provide less than ideal results in at least some instances. For example, the alignment of the eye with the laser surgery system can be less than ideal in at least some instances, such as when refractive treatment of the cornea of the eye is combined with a treatment of the lens of the eye such as removal of the cortex and nucleus from the eye.

The eye comprises complex optical structures, and at least some of the prior laser eye surgery systems can be less than ideally suited to treat at least some eyes. For example, it could be helpful to decrease higher order aberrations of the eye such as spherical aberration and coma, and at least some of the prior methods and apparatus of treating the eye can be less than ideally suited for correcting aberrations of the eye. For example, misalignment of the eye with the surgical treatment apparatus can result in less than ideal placement of incisions in at least some instances.

Although prior systems have attempted to combine laser eye surgery systems with data from eye measurement devices, the results can be less than ideal in at least some instances. The surgical eye can be altered as compared with the natural eye, and anatomical structures of the surgical eye may not coincide with anatomical structures of the eye prior to surgery. For example, the cornea can be distorted during surgery, for example from contact with the patient interface or from alternation of the surface of the cornea. Also, the eye can undergo cyclotorsion when moved from one measurement system to another measurement system such that alignment of the angle of the eye can be less than ideal. Also, the pupil of the eye during surgery can differ from the pupil of the eye that would be used for normal vision, which can make alignment of the eye with surgical incisions and intraocular lenses more challenging than would be ideal. For example, in at least some instances the pupil of the eye can dilate and affect the location of the center of the pupil.

There are other factors that may limit the usefulness of data provided to a surgical laser from eye measurement devices such as tomography and topography systems. For example, there can be at least some distortion of at least some of the images taken among different devices, and this distortion can make the placement of laser incisions less than ideal in at least some instances. Also, the use of different systems for measurement and treatment can introduce alignment errors, may take more time that would be ideal, and may increase the cost of surgery such that fewer patients than would be ideal can receive beneficial treatments.

At least some prior ophthalmic laser surgery systems can be less than ideally suited for combination with prior topography systems. For example, prior laser surgery systems for cutting the cornea may rely on a patient interface that can make measurements of the cornea less than ideal in at least some instances. The prior patient interfaces may apply force to the eye, for example with a suction ring that engages the eye near the limbus. The resulting force can distort the corneal shape and decrease accuracy of the corneal measurements in at least some instances. The distortions of the cornea related to placement of the patient interface can limit the accuracy of corneal measurements and alignment of the corneal surgical procedures. Also, the images obtained with prior laser systems configured to couple to the eye with patient interfaces can be distorted at least partially in at least some instances, which can make combination of the images from prior laser surgery system with prior eye measurement systems such as corneal topography and tomography systems less than ideal in at least some instances.

In light of the above, it would be desirable to provide improved methods and apparatus that overcome at least some of the above limitations of the above prior systems and methods. Ideally, these improved systems and methods will provide improved alignment with the eye during surgery, improved placement of laser beam pulses to incise the eye, improved placement of refractive incisions of the eye, improve placement of incisions for intraocular lenses, corneal topography from the laser surgery system without distorting the corneal shape, and integration of the measurement data with the laser treatment parameters, in order to provide an improved result for the patient.

SUMMARY

Embodiments as described herein provide improved treatment of materials such tissue. In many embodiments the tissue comprise ocular tissue such as one or more of corneal tissues or lenticular tissue incised, for refractive surgery such as the placement of intraocular lenses or corneal incisions and combinations thereof. In many embodiments, improved methods and apparatus for performing laser eye surgery are provided for beneficially placing laser incisions on tissue structures of the eye when the eye comprises distortions related to the laser eye surgery, such as distortion related to coupling the eye to an interface of the laser system or distortions related to substances applied to the eye during surgery. The embodiments as described can also be used to align the incisions with locations of the eye that may not be readily measured when the patient interface contacts the eye and inhibits movement of the eye, such as optical structures defined when the patient views a target and the eye moves freely and optical structures defined without distortion of the eye. Many of the embodiments as disclosed herein are also well suited for combination with laser eye surgery systems that do not rely on patient interfaces, such as laser surgical systems used in combination with pharmacological substances that may affect vision of the eye. The embodiments as described herein can provide improved placement of intraocular lenses in relation to treatment axes and the nodal points of the eye, such that the placed lens can provide a post surgical eye having similar nodal points to the pre-operative eye in order to provide improved accuracy of correction and decreased aberrations with the replacement lens. In many embodiments, intraocular lenses are identified for treatment in response to locations of the measured nodal points of the eye in order to provide similar locations of the nodal points of the post-operative eye.

In many embodiments, the eye is initially measured without contacting the eye with a patient interface, and these measurements are used to determine alignment of the incisions when the patient interface contacts the eye or when the eye has been distorted with a pharmacological substance, and combinations thereof. The eye of the patient can be measured when the patient has been placed on a patient support of the surgical laser prior to the patient interface contacting the eye, and these measurements can be used to determine locations of the laser incisions when the patient interface contacts the eye. Alternatively or in combination, one or more tissue structures of the eye can be measured away from the patient support of the surgical laser and prior to contacting the eye with the patient interface, and these measurements used to determine locations of one or more optical structures of the eye when the patient interface contacts the eye. The pre-contact locations of the one or more structures of the eye can be used to determine corresponding post-contact locations of the one or more optical structures of the eye when the patient interface has contacted the eye, such that the laser incisions are placed at locations that promote normal vision of the eye. This approach has the advantage of positioning the incisions in relation to the pre-contact optical structures of the eye, even when the eye has been distorted as may occur with the patient interface or with substances placed on the eye during surgery such as mydriatic substances.

While the locations of the incisions on the eye can be determined in one or more of many ways, in many embodiments an image of the eye coupled to the patient interface is displayed to a user with one or more identifiable markings provided on the display to show the user the locations of the one or more optical structures of the eye. The locations of the one or more optical structures of the eye can be determined from the measurements obtained prior to contacting the eye with the interface and positioned on the image of the eye coupled to the interface in order to reference the incisions of the eye in relation to the locations of the one or more optical structures prior to the patient interface contacting the eye. The image of the eye may comprise a sagittal view of the eye, a transverse view of the eye, or an anterior view of the eye, and combinations thereof. The one or more images of the eye may comprise a tomography image showing a plane of the eye and an anterior camera view of the eye, and the one or more optical structures can be placed on the one or more images to provide one or more reference locations to the user. In many embodiments, the one or more images comprise real time images provided for the user to plan and evaluate the progress of the incisions placed on the eye. Providing the tomography image and the anterior image with markers can be particularly helpful for the user to identify one or more axes of the eye related to vision when the interface contacts the eye, such as when the one or more axes of the eye extend away from an axis of the optical delivery system through one or more apparent layers of the eye, such as from an entrance pupil of the eye adjacent the lens to the front surface of the cornea.

The optical structure of the eye may comprise one or more structures of the eye related to optics of the eye, and the tissue structure of the eye may comprise one or more tissues of the eye. The optical structure of the eye may comprise one or more of an optical axis of the eye, a visual axis of the eye, a line of sight of the eye, a pupillary axis of the eye, a fixation axis of the eye, a vertex of the cornea, an anterior nodal point of the eye, a posterior nodal point of the eye, an anterior principal point of the eye, a posterior principal point of the eye, a keratometry axis, a center of curvature of the anterior corneal surface, a center of curvature of the posterior corneal surface, a center of curvature of the anterior lens capsule, a center of curvature of the posterior lens capsule, a center of the pupil, a center of the iris, a center of the entrance pupil, or a center of the exit pupil of the eye. The optical structure of the eye may comprise a pre-contact optical structure determined with measurements obtained prior to the interface contacting the eye, or a post-contact optical structure of the eye determined with measurements obtained when the interface has contacted the eye. In many embodiments, the optical structure comprises the pre-contact optical structure and the location of the pre-contact structure is determined on the post-contact eye in relation to one or more post-contact tissue structures of the eye. The one or more post-contact tissue structures may comprise one or more of the iris, a plane of the iris, an outer boundary of the iris, the limbus, a center of the limbus, sclera blood vessels, a center of the cornea, a thickness profile of the cornea, a center of curvature of a thickness profile of the cornea, a tissue stained with a dye such as an ink, the vertex of the cornea, the optical axis of the eye, a center of curvature of the anterior surface of the cornea, a center of curvature of the anterior lens capsule, a center of curvature of the posterior lens capsule In many embodiments, an axis of the optical delivery system is shown on the display and the one or more images of the eye with an identifiable mark on the display such, such as a reticle to indicate the location of the axis of the optical delivery system.

In many embodiments, the laser eye surgery system comprises a fixation light viewed by the patient when a ring of the patient interface is placed on the eye in order to improve alignment of the patient interface with the eye. The fixation light may be adjustable to the patient in order to decrease blur when the patient views the light prior to placement of the patient interface on the eye and also when patient interface contacts the eye and decreases optical power of the eye. When the patient interface has been placed on the eye, the patient may be asked to look at the light or describe the location of the light in order to confirm alignment of the patient interface with the eye. Alternatively or in combination, the reflection light from the cornea may be displayed with the real time anterior image of the eye, which can assist the user with alignment of the eye. In many embodiments, the one or more marks indicating the locations of one or more optical structures of eye can be shown on the display with the reflection of the fixation light in order for the user to determine alignment of the eye. The one or more marks may identify locations of one or more optical structures of the eye prior to contact with the patient interface, or identify locations of one or more structures of the eye contacting the patient interface such as a center of the limbus of the eye or centers of curvature of the lens of the eye, for example.

In many embodiments, one or more measurements of a cornea in a substantially undistorted shape are used to determine parameters that are used to determine locations of incisions of the cornea, such as corneal incisions. The one or more measurements can be obtained in many ways, such as with images used for measuring corneal topography or tomography, or without imaging the eye. One or more additional images can be obtained when the one or more measurements are obtained, and these one or more additional images can be used in combination with the measurements for aligning the measurement coordinates and the cutting coordinates.

In many embodiments, a surface profile of the cornea is measured when the eye is placed in an undistorted shape, for example without being in contact with an external structure such as a patient interface, such that distortion of the cornea and measurement distortion is substantially inhibited. When the eye has been placed in an undistorted configuration such as when the patient is supported with a patient support of the laser surgery system and views the fixation light, the cornea of the eye can be exposed to air with a tear film or other liquid over the cornea. The surface profile of the substantially undistorted cornea can be measured in one or more of many ways, and may comprise one or more of an anterior corneal surface topography profile, a posterior a corneal surface topography profile, or a corneal thickness profile. In many embodiments, the surface profile comprises a representation of a three dimensional profile and may comprise an extraction of one or more parameters from one or more images, such as an extraction of keratometry values from a corneal topography system or tomography system integrated with the surgical laser. The one or more parameters can be used to determine a tissue treatment pattern on the eye, such as the angular location, depth, arc length and anterior to posterior dimensions of relaxing incisions. Alternatively or in combination, a first image of the eye can be generated for aligning the eye such as a pupil image of the eye when the eye rests naturally and the surface profile is measured.

Subsequently, the eye can be contacted with a patient interface that may at least partially distort the cornea. In many embodiments, a ring of the patient interface is coupled to the eye with suction, and the ring can induce distortion of the cornea with mechanical coupling to the cornea. Additional components of the interface may induce additional distortion when an optically transmissive structure of the patient interface contacts the cornea, or when the optically transmissive structure is separated from the cornea with a liquid or viscoelastic material, and combinations thereof. The first image can be compared with a second image in order to align the eye with the laser surgery system.

The first image or the one or more measurements, or both, can be obtained in one or more of many ways. In many embodiments, the one or more measurements and the first image are obtained when the patient is placed on a patient support of the laser eye surgery system, such as a patient bed of the laser eye surgery system. The laser eye surgery system may comprise biometry system such as a keratometer, topography or tomography system and the biometry system is used to obtain the corneal measurement to determine treatment parameters and the first image to determine alignment when the patient is supported with the patient support of the laser eye surgery system. The first image may comprise a plurality of first images obtained together, such as a pupil image from a pupil camera and a corneal profile image from the biometery system. The one or more corneal measurements can be used to determine the one or more treatment parameters such as a treatment axis when the patient is supported with the patient support.

When the cornea of the eye is covered with the patient interface, the image of the eye may be at least partially distorted with the interface. In many embodiments, one or more of the second image of the eye or the eye itself can be distorted when liquid or viscoelastic material is placed on the cornea to separate the cornea from an optically transmissive window or lens of the patient interface. The distortion can be corrected in one or more of many ways and may comprise known amounts of distortion that can be corrected in the second image or combined with the first image to provide a more accurate comparison of the first and second images, such that the patient can receive a more accurate treatment.

With the patient interface coupled to the eye, the first image and the second image can be used in one or more of many ways to determine a position and orientation of the eye coupled to the patient interface. In many embodiments, the distortion of the second image resulting from patient interface comprises a determined distortion that can be increased in the first image so that the first image looks like the second image and the second image shown on the display with the first image. Alternatively or in combination, distortion of the second image can be decreased from the second image so that the second image looks like the first image. The distortion can be related to one or more of image magnification variation, translation of the image, rotation of the image, mapping distortion of the imaging apparatus, or placement of the interface over the eye. In many embodiments, the imaging apparatus comprises a first amount of distortion prior to placement of the patient interface over cornea and a second amount of distortion different from the first amount when the interface is placed over the eye, and one or more of the first distortion or the second distortion can be used to determine the mapping function to correct or distort the images. In many embodiments, a mapping function can be used to map the first image to the second image based on predetermined amounts of distortion. In many embodiments, a laser eye surgery system comprises a processor, such as a processor system, and instructions of a computer program are stored on a tangible medium comprising a computer memory. The instructions are configured to adjust one or more of the first image or second image in response to predetermined amounts of distortion, such as by mapping the first image to a distorted first image. The distorted first image can be provided on a display for the physician to align with the second image shown on the display. Alternatively or in combination, the alignment of first and second images can be done with software algorithms, such as one or more of correlation or pattern recognition.

In a first aspect, a method of treating an eye of a patient is provided. A first image of the eye is generated when the eye is separated from the patient interface such that the eye comprises a natural, undistorted state. A ring of a patient interface can be coupled to the eye, and the cornea covered with an optic of the patient interface. A second image of the eye with the patient interface over the cornea is generated. In this second image, the patient interface alters distortion of the second image of the eye. In many embodiments, one or more of a position or an orientation of the eye is determined in response to the first image and the second image when the patient interface has been placed over the cornea.

A shape profile of the cornea of the eye can be measured when at least the eye of the patient is supported with a patient support of a laser surgery system. The shape profile can be measured and the first image can be generated before a suction ring of a patient interface is placed on the eye. The second image can be generated when the patient is supported with the patient support of the laser surgery system. The shape profile can be used to determine an axis of treatment of an astigmatism of the eye. The shape profile can comprise one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack topography of the eye, a Scheimpflug image topography of the eye, a confocal tomography of the eye, or a low coherence reflectometry of the eye. The shape profile can be used to determine an axis of treatment of a plurality of arcuate incisions, the plurality of arcuate incisions extending along an arc transverse to the axis of treatment. Locations of the plurality of arcuate incisions can be displayed on the second image of the eye distorted with the patient interface. Locations of the plurality of arcuate incisions can be mapped from first locations of the first image to second locations of the second image with the second locations corresponding to distortion of the eye with the patient interface. The first image and the second image may be generated with a camera of the laser surgery system.

In many embodiments, the first image is modified to provide a distorted first image comprising distortion similar to the second image. The distorted first image can be provided on a display visible to a user. A user can adjust one or more of a location or an angle of the first distorted image on the display. Locations of a plurality of laser beam pulses can be adjusted in response to the location or the angle of the first distorted image on the display. The distorted first image can be overlaid on the second image on the display to determine the position and the angle of the eye for treatment. A processor can determine the position and the angle of the distorted first image on the display in response to user input to adjust the locations of the plurality of laser beam pulses.

In many embodiments, the second image is modified to provide a corrected second image comprising less distortion similar to the first image.

In many embodiments, the patient interface comprises a light transmissive optic disposed along an optical path with one or more of a liquid or a viscoelastic material disposed between the cornea and the light transmissive optic. The optic and the one or more of the liquid or the viscoelastic may distort the image of the eye.

In many embodiments, the first image comprises a plurality of image structures corresponding to a plurality of tissue structures of the eye. The plurality of image structures can be moved from a first plurality of locations of the first image to a second plurality of locations of the distorted first image in response to distortion of the patient interface.

In many embodiments, the first image and the second image correspond to a coordinate reference of a laser treatment system. A plurality of locations of the first image can be mapped from first locations of the coordinate reference of the laser system to second locations of the coordinate reference of the laser system to provide distortion of the first distorted image corresponding to distortion of the second image in order to position the first distorted image in alignment with the second image.

In many embodiments, the first image and the second image correspond to a first coordinate reference of an ancillary diagnostic device and a second coordinate reference of a laser treatment system, respectively. A plurality of locations of the first image can be mapped from first locations of the first coordinate reference to second locations of the second coordinate reference of the laser system in order to determine of the position and the orientation of the eye with the patient interface over the cornea.

In many embodiments, the gas comprises air and the liquid comprises one or more of a solution, saline or a viscoelastic fluid.

In many embodiments, the first image of the eye and the second image of the eye comprise images of an iris of the eye from a camera. One or more structures of the first image and the second image may correspond to one or more structures of the iris.

In many embodiments, the cornea exposed to the gas comprises a tear layer.

In another aspect, an apparatus comprising a processor having a tangible medium configured to perform any combination of the method steps above is provided.

In yet another aspect, an apparatus for treating an eye having a cornea is provided. The apparatus comprises a topography measurement system, an image capture device, a patient interface, and a processor. The topography measurement system measures a topography of the cornea of the eye. The image capture device captures an image of the eye. The patient interface couples to and retains the eye. The processor comprises a tangible medium configured to determine a position of the eye.

The topography measurement system may comprise one or more of a keratometry system, an optical coherence tomography system, a Placido disc topography system, a Hartmann-Shack topography system, a Scheimpflug image topography system, a confocal tomography system, or a low coherence reflectometry system. The patient interface may comprise a suction ring.

In many embodiments, the image capture device is configured to capture a first image of the eye when the cornea is exposed to a gas and a second image of the eye with the patient interface over the cornea. The processor comprising the tangible medium may be configured to determine one or more of a position or an orientation of the eye in response to the first image and the second image when the patient interface has been placed over the cornea.

The topography measurement system may be configured to measure a shape profile of the cornea of the eye when at least the eye of the patient is supported with a patient support of a laser surgery system. The shape profile can be measured and the first image can be generated before a suction ring of a patient interface is placed on the eye. The second image can be generated when the patient is supported with the patient support of the laser surgery system. The shape profile can be used to determine an axis of treatment of an astigmatism of the eye. The shape profile may comprise one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack topography of the eye, a Scheimpflug image topography of the eye, a confocal tomography of the eye, or a low coherence reflectometry of the eye. The shape profile can be used to determine an axis of treatment of a plurality of arcuate incisions, the plurality of arcuate incisions extending along an arc transverse to the axis of treatment. Locations of the plurality of arcuate incisions can be displayed on the second image of the eye distorted with the patient interface. Locations of the plurality of arcuate incisions can be mapped from first locations of the first image to second locations of the second image. The second locations may correspond to distortion of the eye with the patient interface. The first image and the second image may be generated with a camera of the laser surgery system.

The apparatus may further comprise a display visible to a user. The processor comprising the tangible medium may be configured to modify the first image to provide a distorted first image comprising distortion similar to the second image and provide the distorted first image on the display. The display can be configured to allow a user to adjust one or more of a location or an angle of the first distorted image on the display. Locations of a plurality of laser beam pulses can be adjusted in response to the location or the angle of the first distorted image on the display. The distorted first image can be overlaid on the second image on the display to determine the position and the angle of the eye for treatment. The processor comprising the tangible medium can be configured to determine the position and the angle of the distorted first image on the display in response to user input to adjust the locations of the plurality of laser beam pulses.

In many embodiments, the processor comprising the tangible medium can be configured to modify the second image to provide a corrected second image comprising less distortion similar to the first image.

In many embodiments, the patient interface comprises a light transmissive optic disposed along an optical path with one or more of a liquid or a viscoelastic material disposed between the cornea and the light transmissive optic. The optic and the one or more of the liquid or the viscoelastic may distort the image of the eye.

In many embodiments, the first image comprises a plurality of image structures corresponding to a plurality of tissue structures of the eye. The plurality of image structures can be moved from a first plurality of locations of the first image to a second plurality of locations of the distorted first image in response to distortion of the patient interface.

In many embodiments, the first image and the second image correspond to a coordinate reference of a laser treatment system. A plurality of locations of the first image can be mapped from first locations of the coordinate reference of the laser system to second locations of the coordinate reference of the laser system to provide distortion of the first distorted image corresponding to distortion of the second image in order to position the first distorted image in alignment with the second image.

In many embodiments, the first image and the second image correspond to a first coordinate reference of an ancillary diagnostic device and a second coordinate reference of a laser treatment system, respectively. A plurality of locations of the first image can be mapped from first locations of the first coordinate reference to second locations of the second coordinate reference of the laser system in order to determine of the position and the orientation of the eye with the patient interface over the cornea.

The gas the cornea may be exposed to may comprise air. The liquid the cornea may be exposed to may comprise one or more of a solution, saline or a viscoelastic fluid. The cornea exposed to the gas may comprise a tear layer.

The first image of the eye and the second image of the eye may comprise images of an iris of the eye from the image capture device. One or more structures of the first image and the second image may correspond to one or more structures of the iris.

In another aspect, embodiments provide method of measuring an eye. The method comprises coupling a corneal topography measurement structure to a patient interface structure to place the topography measurement structure in front of the eye. The eye is measured with the topography measurement structure and the patient interface away from the eye. The corneal topography measurement structure is decoupled from the patient interface structure. The patient interface structure is coupled to a component of the patient interface in order to contact the eye. An astigmatism axis of the eye is determined in response to the measurement of the eye with the corneal topography structure removable coupled to the patient interface.

In another aspect, embodiments provide an apparatus to measure an eye. The apparatus comprises a patient interface. A topography measurement structure is configured to couple to the patient interface to measure the eye without contacting the eye

BRIEF DESCRIPTION OF THE DRAWINGS

FIG. 6A1 shows corneal profile data for the coordinate system and image of FIG. 6A;

FIG. 6A2 shows corneal thickness profile data for the coordinate system and images of FIGS. 6A and 6A1;

FIG. 6A3 shows corneal thickness profile maps for the coordinate system and images of FIGS. 6A, 6A1 and 6A2;

FIG. 6C1 shows corneal profile data for the coordinate system and image of FIG. 6C;

FIG. 6C2 shows corneal thickness profile data for the coordinate system and images of FIGS. 6C and 6C1;

FIG. 6C3 shows corneal thickness profile maps for the coordinate system and images of FIGS. 6C, 6C1 and 6C2;

FIGS. 7D and 7E show the eye as in FIGS. 7A to 7C coupled to a patient interface for treatment, in accordance with many embodiments;

FIG. 7F shows coordinate transformations of the measurement coordinate reference system prior to contacting the eye with the laser system and the measurement coordinate reference system when the eye contacts the patient interface as in FIGS. 7D and 7E;

FIG. 7G shows an optical schematic of the eye as in FIGS. 7A and 7B;

DETAILED DESCRIPTION

Figure 1:
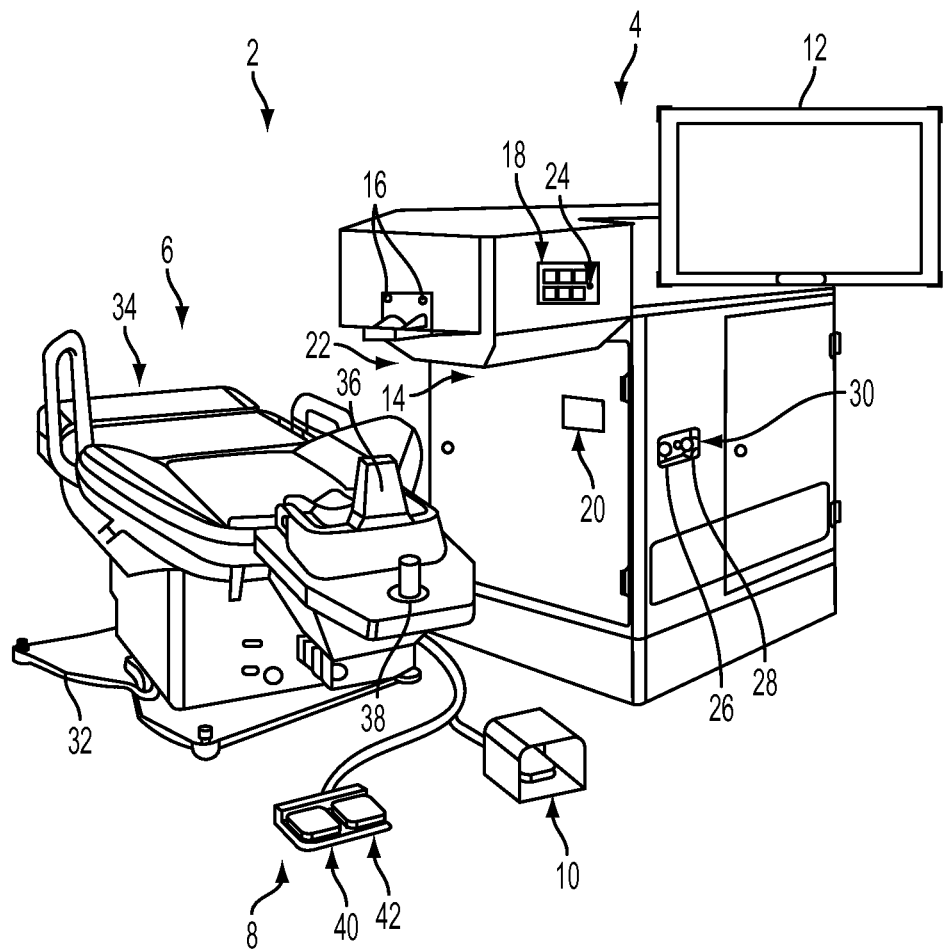
FIG. 1 shows a perspective view showing a laser eye surgery system, in accordance with many embodiments.

Methods and systems related to laser eye surgery are disclosed. In many embodiments, a laser is used to form precise incisions in the cornea, in the lens capsule, and/or in the crystalline lens nucleus. Although specific reference is made to tissue retention for laser eye surgery, embodiments as described herein can be used in one or more of many ways with many surgical procedures and devices, such as orthopedic surgery, robotic surgery and microkeratomes.

The embodiments as describe herein are particularly well suited for treating tissue, such as with the surgical treatment of tissue. In many embodiments, the tissue comprises an optically transmissive tissue, such as tissue of an eye. The embodiments as described herein can be combined in many ways with one or more of many known refractive surgical procedures such as cataract surgery, corneal incisions, including laser assisted in situ keratomileusis (hereinafter "LASIK"), all laser LASIK, femto LASIK, corneaplasty, astigmatic keratotomy, corneal relaxing incision (hereinafter "CRI"), Limbal Relaxing Incision (hereinafter "LRI"), photorefractive keratectomy (hereinafter "PRK") and Small Incision Lens Extraction (hereinafter "SMILE"), for example.

The embodiments as described herein are particularly well suited for combination with intraocular lenses, for example with components of one or more known intraocular lenses such as one or more of accommodating intraocular lenses or intraocular lenses to correct aberrations of the eye, for example accommodating aberration correcting lenses of the eye. The embodiments disclosed herein can be used to combine refractive surgical procedures with intraocular lenses, for example.

The embodiments as described herein can be used position to incisions of the lens capsule sized to receive structures of an intraocular lens in order to retain the placed IOL in alignment with one or more axes the eye as described herein, for example in combination with lens capsules and structures as described in U.S. Pat. App. Ser. No. 61/788,201, filed Mar. 15, 2013, entitled "Microfemtotomy methods and systems", the entire disclosure of which is incorporated herein by reference.

The embodiments as described herein can be used to position fiducial markings on the eye aligned with one or more axes of the eye as described herein in order to align an axis of an IOL with the eye, for example in combination with fiducial markings and lenses as described in U.S. Ser. No. 61/813,172, filed Apr. 17, 2013, entitled "Laser fiducials for alignment in cataract surgery (attorney docket number U.S. 43406-747.101)

Methods and systems related to laser treatment of materials and which can be used with eye surgery such as laser eye surgery are disclosed. A laser may be used to form precise incisions in the cornea, in the lens capsule, and/or in the crystalline lens nucleus, for example. The embodiments as described herein can be particularly well suited for increasing the accuracy of the cutting of the material such as tissue, for example.

In many embodiments, a patient interface coupled to the eye influences distortion of images and measurements of the eye obtained through the patient interface. The patient interface may comprise a suction ring that can be placed on the eye near the limbus, and placement of the suction ring on the eye can influence distortion of the cornea. The patient interface may comprise an optically transmissive structure such as a flat plate or lens, and the optically transmissive structure can influence distortion of the second image. For example, the patient interface may add barrel distortion to images of the eye taken through the patient interface as compared with images of the eye taken when the patient interface has been separated from the eye and the eye comprises a natural configuration. Alternatively, the patient interface be designed to add pincushion distortion, for example. The embodiments disclosed herein are particularly well suited for combination with a patient interface having an optically transmissive element separated from the cornea. The curved lower surface of the optically transmissive lens structure separated from the cornea to urge gas bubbles away from the optical axis can increase the depth of field and range of the treatment, and the embodiments disclosed herein are ideally suited for use with such a patient interface.

The embodiments disclosed herein also suited for combination with corneal measurement systems. The corneal measurement system may comprise a component of the laser surgery system, which allows the cornea to be measured with the corneal measurement system when the patient is supported with a patient support such as a bed of the laser surgery system. Alternatively, the corneal measurement system may comprise a corneal measurement system separated from the laser system, such as in another room of a physician's office.

The embodiments disclosed herein are well suited for combination with prior laser surgery systems, such as Catalys™ commercially available from Optimedica, and similar systems. Such systems can be modified in accordance with the teachings disclosed herein and to more accurately measure and treat the eye.

As used herein like characters such as reference numerals and letters described like elements.

As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

As used herein the term anterior and posterior nodal points of the eye may have the property that a ray aimed at one node will be refracted by the eye such that it appears to have come from the other node, and with the same angle with respect to the optical axis.

The embodiments disclosed herein enable accurate and substantially distortion-free corneal topography measurement and subsequent integration with the laser treatment. In many embodiments, means for accomplishing at least three steps are provided:

1. Positioning the patient eye within the capture range of the measurement system;

2. A measurement system that is capable of accurately measuring the corneal; and 3. Correcting for one or more of many changes in the patient eye orientation that may occur between the measurement time and the laser treatment time.

Positioning

In many embodiments, positioning of the patient for laser surgery is provided by motion of the patient bed or by motion of the laser system. The operator has manual control of the lateral and axial position, guiding the docking mechanism into place. In the absence of a docking mechanism, the operator can be provided with means for guiding the motion so that the eye, such that the cornea is placed within the operative range of the measurement system. This can be accomplished with the subsystems of Catalys™ and similar systems, with some modifications in accordance with embodiments disclosed herein. Initial patient position can be guided by the video camera, in order to guide the eye into lateral position by centering the video image and into axial position by focusing the image with the video camera, for example. At the completion of this step the cornea is within the capture range of the tomography system. The tomography system may comprise one or more of many tomography systems as described herein, and may comprise an optical coherence tomography system (hereinafter "OCT" system), a Scheimpflug imaging system, a low coherence reflectometry system, or a scanning confocal spot imaging system, for example. The tomography system such as the OCT system is used to measure the axial position of the cornea, and a suitable display provides the operator guidance for final, accurate positioning.

In many embodiments, the video and OCT systems are configured to operate with the docking system, which has additional optical elements and liquid medium in the optics path, it may be helpful to adjust the focusing algorithms of the laser system to account for operation without the docking mechanism optics and interface medium such as a liquid or viscoelastic.

Measurement

In many embodiments, the laser system has a subsystem for mapping the ocular surfaces that are being treated, such as with tomography as described herein. The measurement step is preferable done when the eye has been positioned correctly. A fixation light can optionally be introduced to help the patient keep the eye pointed at in a fixed direction at a fixed angle. If the measurement data capture is fast enough, on the order of one second for example, a fixation light may not be as beneficial. Multiple tomography scans, such as OCT, of the cornea surfaces can be acquired in a short time. Multiple scans increase the accuracy of the data, and can provide topography data of the cornea. Post processing of the scans may be used to remove potential eye motion and improves the measurement accuracy.

When the corneal surfaces have been mapped, polynomial fitting algorithms or other fitting algorithms can be used to calculate useful parameters of the cornea such as one or more of the optical power of the cornea, the astigmatic axis angle, and astigmatism magnitude, for example.

Examples of fitting algorithms suitable for mapping optical tissue surfaces include elliptical surfaces, Fourier transforms, polynomials, a spherical harmonics, Taylor polynomials, a wavelet transform, or Zernike polynomials. In many embodiments, three dimensional elevation profile data of an optical tissue surface of the eye is provided, and the data fit to the optical tissue surface. The optical tissue surface may comprise one or more of the anterior surface of the cornea, the posterior surface of the cornea, the anterior surface of the lens capsule, the posterior surface of the lens capsule, an anterior surface of the lens cortex, a posterior surface of the lens cortex, an anterior surface of the lens nucleus, a posterior surface of the lens nucleus, one or more anterior surfaces of the lens having a substantially constant index of refraction, one or more posterior surfaces of the lens having a substantially constant index of refraction, the retinal surface, the foveal surface, a target tissue surface to correct vision such as a target corneal surface, an anterior surface of an intraocular lens, or a posterior surface of an intraocular lens, for example. As the index of refraction of the lens can vary from about 1.36 to about 1.41, optical surfaces of the lens may define one or more layers of the lens having a similar index of refraction, for example.

Coordinate System Transfer

In many embodiments, when the patient eye is docked for treatment, the eye changes one or more of position or rotation relative to the laser system coordinates. The position may comprise three positional dimensions, and the rotation may comprise three rotational dimensions, and the change in position or orientation may comprise all six degrees of freedom in at least some embodiments. This change in one or more of position or orientation can be a result of patient head movement, eye movement, or related to force applied during docking of the eye with the patient interface. It may be helpful to transform the corneal measurements, like the astigmatic axis angle, to the new coordinate system. There are several methods for accomplishing this.

One method allows the operator to mark the patient eye, prior to the measurement, with ink dots that are typically positioned diametrically across on the periphery of the cornea. These dots can be acquired by the imaging camera after docking for treatment and used for calculating the coordinate transformation.

Another method is to use ocular features that are visible in the video images, or the OCT scans, taken during the corneal measurement step and to determine the position and orientation of the eye. This determination can be made with correlation for example, or identification for example, of the features of the first image in relation to features of the second image taken after docking for treatment. This identification or correlation can be done by digital image processing algorithms, or manually by the operator. When done manually the operator is presented by overlapped images (measurement and treatment steps) on the display screen, and the images are manually manipulated in translation and rotation until they are visibly matched. The image manipulation data is detected by the display software and used for the coordinate transform.

The processor system may comprise tangible medium embodying instructions of a computer program to perform one or more of the method steps as described herein.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen display control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
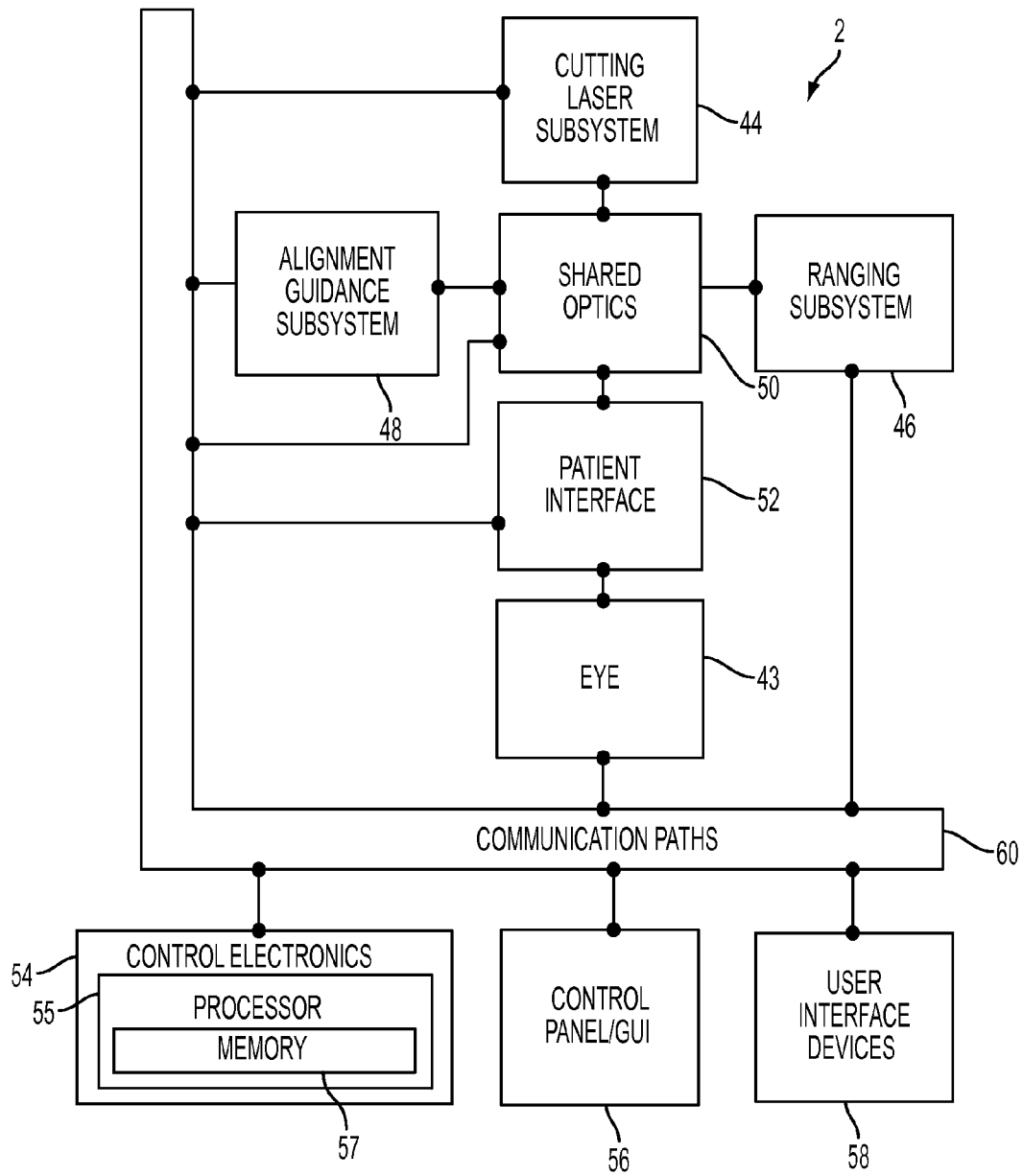
FIG. 2 shows a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea 43C, a lens 43L and an iris 43I. The iris 43I defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components. The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3A:
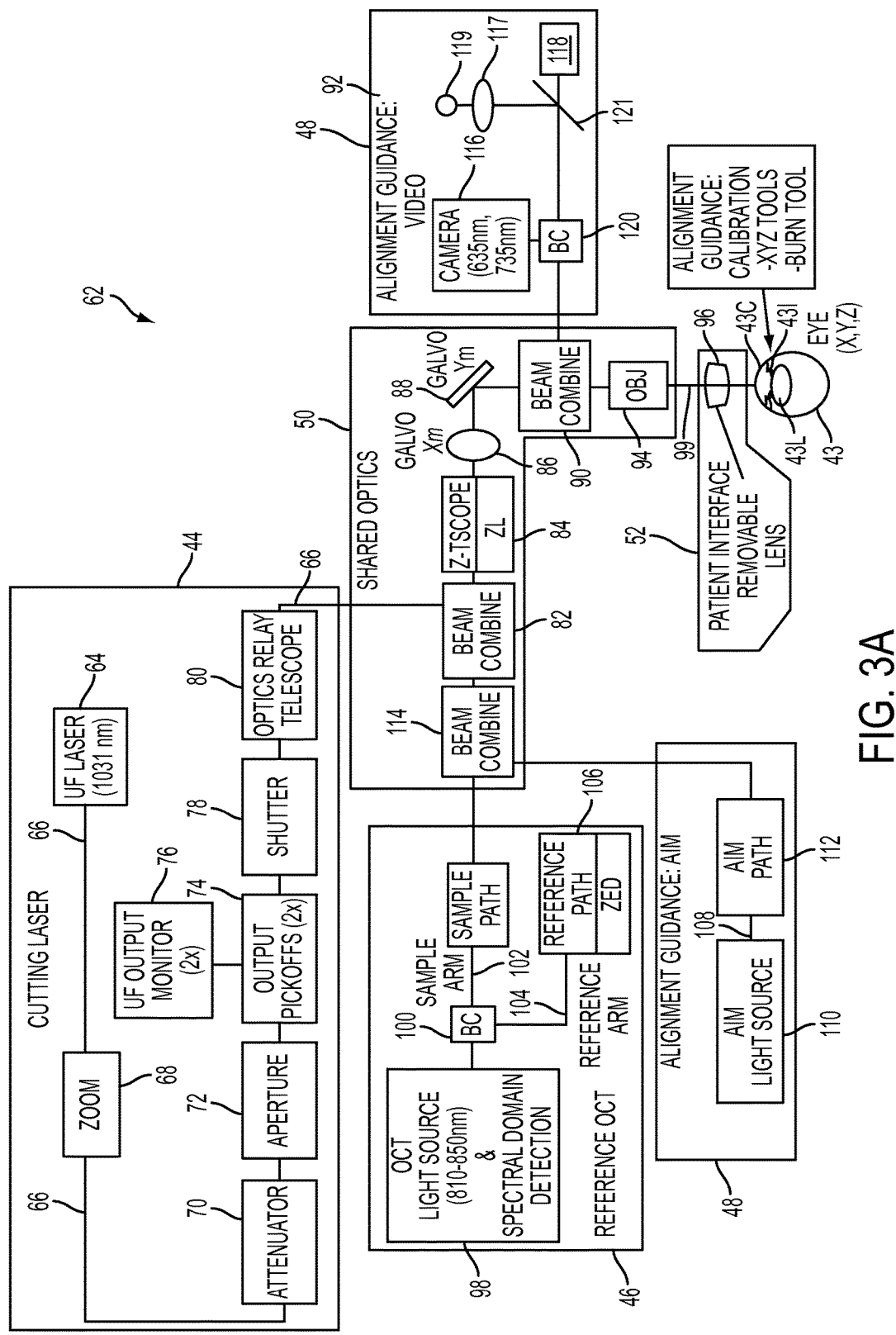
FIG. 3A shows a simplified block diagram illustrating the configuration of an optical assembly of a laser eye surgery system, in accordance with many embodiments.

FIG. 3A is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials places on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

The ranging subsystem 46 in FIG. 3 includes an OCT light source and detection device 98. The OCT light source and detection device 98 includes a light source that generates and emits light with a suitable broad spectrum. For example, in many embodiments, the OCT light source and detection device 98 generates and emits light with a broad spectrum from 810 nm to 850 nm wavelength. The generated and emitted light is coupled to the device 98 by a single mode fiber optic connection.

The light emitted from the OCT light source and detection device 98 is passed through a beam combiner 100, which divides the light into a sample portion 102 and a reference portion 104. A significant portion of the sample portion 102 is transmitted through the shared optics 50. A relative small portion of the sample portion is reflected from the patient interface 52 and/or the patient's eye 43 and travels back through the shared optics 50, back through the beam combiner 100 and into the OCT light source and detection device 98. The reference portion 104 is transmitted along a reference path 106 having an adjustable path length. The reference path 106 is configured to receive the reference portion 104 from the beam combiner 100, propagate the reference portion 104 over an adjustable path length, and then return the reference portion 106 back to the beam combiner 100, which then directs the returned reference portion 104 back to the OCT light source and detection device 98. The OCT light source and detection device 98 then directs the returning small portion of the sample portion 102 and the returning reference portion 104 into a detection assembly, which employs a time domain detection technique, a frequency detection technique, or a single point detection technique. For example, a frequency-domain technique can be used with an OCT wavelength of 830 nm and bandwidth of 10 nm.

Once combined with the UF laser pulse beam 66 subsequent to the beam combiner 82, the OCT sample portion beam 102 follows a shared path with the UF laser pulse beam 66 through the shared optics 50 and the patient interface 52. In this way, the OCT sample portion beam 102 is generally indicative of the location of the UF laser pulse beam 66. Similar to the UF laser beam, the OCT sample portion beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the beam combiner 100, and back into the OCT light source and detection device 98. The returning back reflections of the sample portion 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for a axially stationary surface in the eye of patient interface volume because the optical path length does not change as a function of different settings of the Z-telescope 84. The ranging subsystem 46 has an inherent Z range that is related to light source and the detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path 106 via a stage ZED within ranging subsystem 46. Passing the OCT sample portion beam 102 through the Z-telescope 84, while not impacting the sample path length, allows for optimization of the OCT signal strength. This is accomplished by focusing the OCT sample portion beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample portion 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample portion beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-filed configuration such that the illumination sources are directed to the independent surfaces outside the capture numerical aperture of the image portion of the video system. Alternatively the illumination may also be in a bright field configuration. In both the dark and bright field configurations, the illumination light source can be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The assembly 62 of system 2 may comprise a fixation light 119 that provides visible light for the patient to fixate during measurement, alignment and treatment of the eye, for example. A lens 117 can be provided to direct light to the eye 43 with vergence suitable for viewing the fixation light. Light emitted from lens 117 is reflected with beam splitter 121 along the optical path of the video camera and illumination optics.

The lens 117 may comprise a fixed lens or a variable lens, for example. The lens 117 may comprise a first configuration to provide a first optical vergence of the light entering the eye prior to placement of fluid on the eye and a second vergence subsequent placement of the interface fluid on the eye in order to correct for changes in refraction of the eye when fluid contacts the cornea. The first configuration may comprise a substantially fixed vergence, or a variable vergence adjusted to the refractive properties of the eye, for example with a variable lens. For an emmetropic patient, the light entering the eye prior to placement of the interface fluid can be collimated, for example. The second configuration of lens 117 can provide a convergent light beam to the eye to focus light onto the retina. As the cornea comprises about 40 Diopters (hereinafter "D") of optical power, and the interface fluid can substantially decrease the optical power of the eye, the lens 117 in the second configuration may provide about 40 D of positive optical power to focus light onto the retina of the eye. This approximately 40D of positive vergence can be quite helpful with embodiments where the patient is asked to fixate on the light when the patient interface fluid has been placed on the cornea.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 3B:
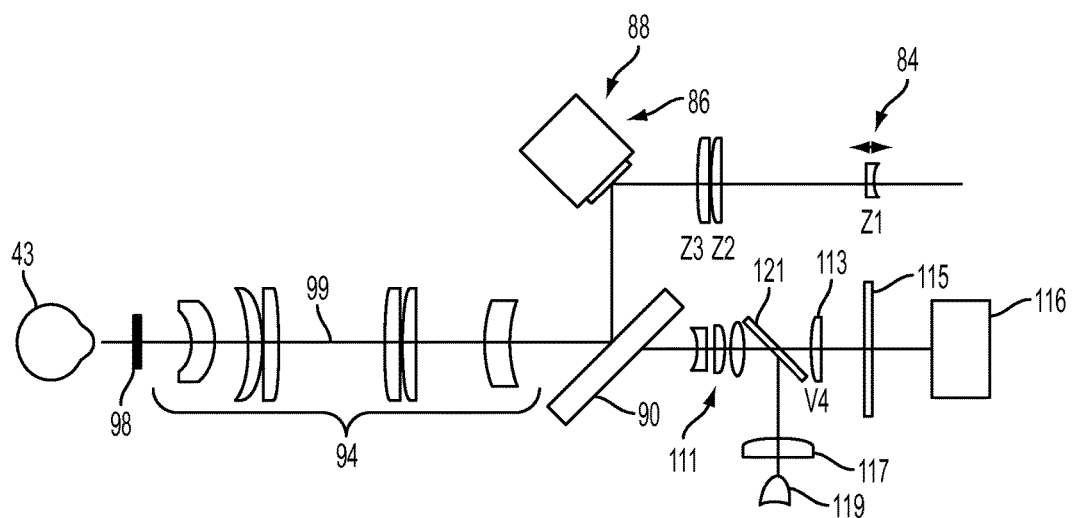
FIG. 3B shows a fixation light integrated into a fixed optical path of a laser system configured to illuminate the eye with external illumination, in accordance with many embodiments.

FIG. 3B shows a fixation light integrated into the fixed video optical path of laser system 2, in which assembly 62 is configured to illuminate the eye with external illumination. The video camera to view the pupil and limbus of the eye may comprise a plurality of lenses to image the iris onto the sensor array of the camera. The plurality of lenses may comprise first one or more lenses 111 and second one or more lenses 113. The beam splitter 121 can be located between the first lens and the second lens, for example. The beam splitter 121 may comprise a thin plate of optically transparent material, for example. The light emitted from the fixation light 119 is transmitted through lens 117 and deflected along the substantially fixed video optical path. The eye 42 can be illuminated with an external light source, for example a light source located away from axis 99 of the optical delivery system as described herein.

Figure 3C:
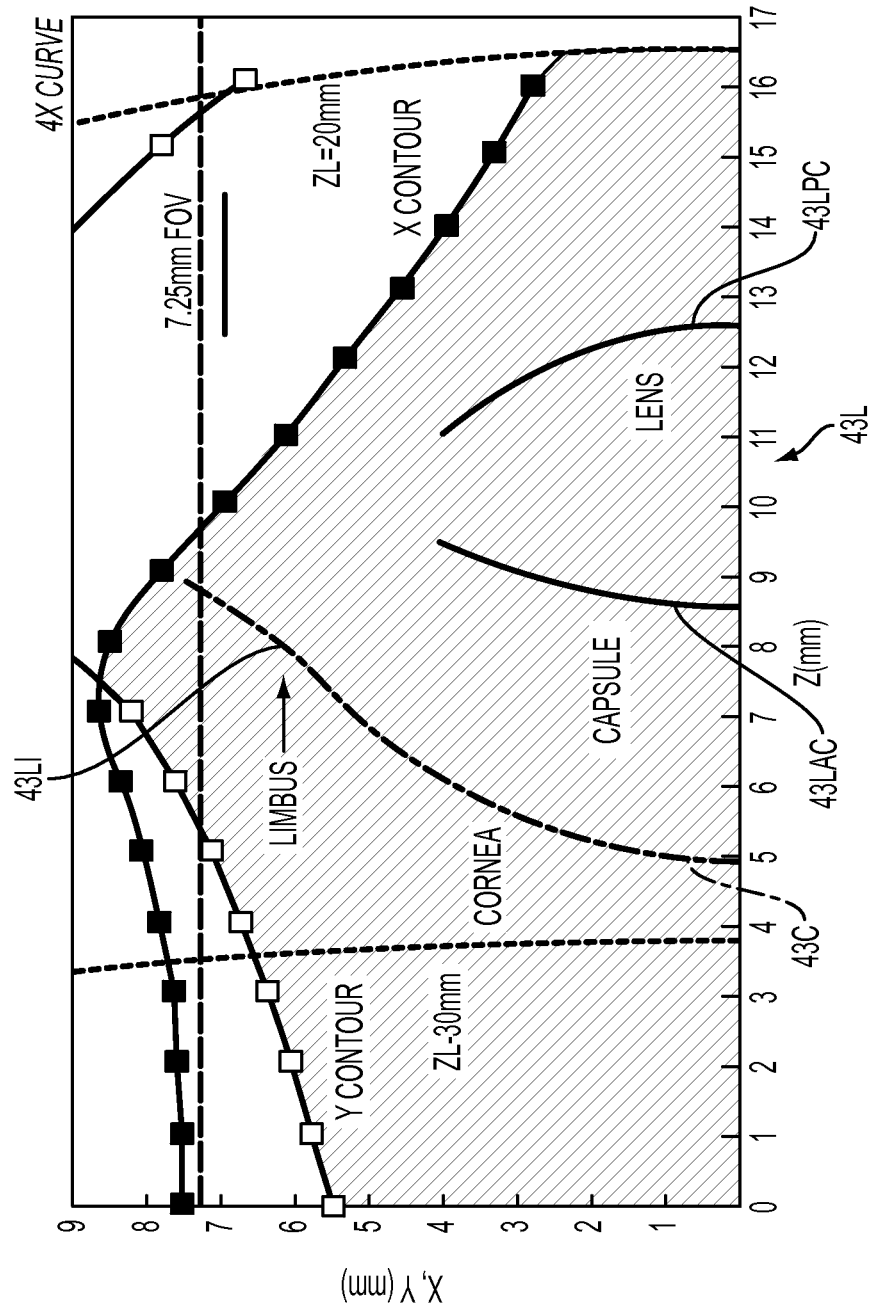
FIG. 3C shows a mapped treatment region of the eye comprising the cornea, the posterior capsule, and the limbus, in accordance with many embodiments.

FIG. 3C shows a mapped treatment region of the eye comprising the cornea 43C, the lens 43L, the anterior lens capsule 43LAC, the posterior capsule 43LPC, and the limbus 43LI. The treatment region can be mapped with computer modeling, for example ray tracing and phased based optical modeling to incorporate factors such as laser beam quality, pulse width, system transmission, numerical aperture, polarization, aberration correction, and alignment. The treatment volume is shown extending along the Z-axis from the posterior surface of the optically transmissive structure of the patient interface a distance of over 15 mm, such that the treatment volume includes the cornea, and the lens in which the treatment volume of the lens includes the anterior capsule, the posterior capsule, the nucleus and the cortex. The treatment volume extends laterally from the center of the cornea to beyond the limbus. The lateral dimensions of the volume are defined by a Y contour anterior to the limbus and by an X contour posterior to the limbus. The treatment volume shown can be determined by a person of ordinary skill in the art based on the teachings described herein. The lateral positions of predicted optical breakdown for ZL fixed to 30 mm and ZL fixed to 20 mm are shown. These surfaces that extend transverse to the axis 99 along the Z-dimension correspond to locations of optical scanning of the X and Y galvos to provide optical breakdown at lateral locations away from the axis 99. The curved non-planner shape of the scan path of optical breakdown for ZL-30 mm and ZL-20 mm can be corrected with the mapping and look up tables as described herein. The curved shape of the focus can be referred to as a warping of the optical breakdown depth and the look up tables can be warped oppositely or otherwise adjusted so as to compensate for the warping of the treatment depth, for example. Additionally, the warping inherent in the prediction from the model can be incorporated in the generic look-up table and any further error from this predicted form as indicated by measurement and application of a correction factor to offset this error may also be called a warping of the look up table.

The treatment region is shown for setting the laser beam energy about four times the threshold amount for optical breakdown empirically determined for a beam near the limbus of the system. The increased energy or margin above ensures that the beam system will be able to treat given variability in contributing factors. Theses contributing factors may include degradation over lifetime of the laser with regard to energy, beam quality, transmission of the system, and alignment.

The placement of the posterior surface of the optically transmissive structure of the patient interface away from the surface of the cornea can provide the extended treatment range as shown, and in many embodiments the optically transmissive structure comprises the lens. In alternative embodiments, the posterior surface of the optically transmissive structure can be placed on the cornea, for example, and the mapping and look up tables as described herein can be used to provide the patient treatment with improved accuracy.

The optically transmissive structure of the patient interface may comprise one or more of many known optically transmissive materials used to manufactures lenses, plates and wedges, for example one or more of glass, BK-7, plastic, acrylic, silica or fused silica for example.

The computer mapping of the treatment volume may optionally be adjusted with mapping based on measurements of a constructed system as described herein.

Figure 4A:
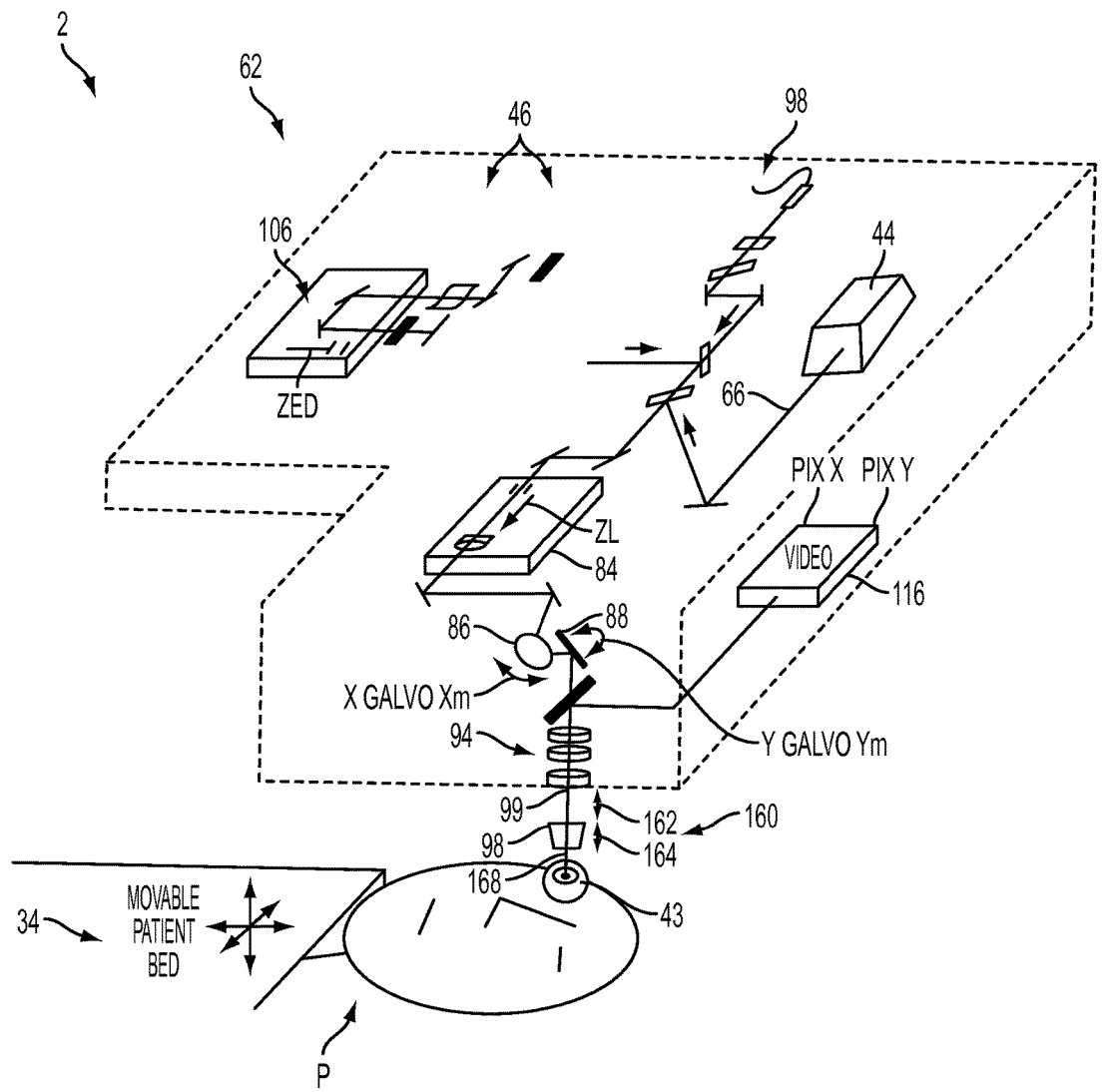
FIG. 4A shows correspondence among movable and sensor components of the laser delivery system, in accordance with many embodiments.

FIG. 4A shows correspondence among movable and sensor components of the laser delivery system 2. The movable components may comprise one or more components of the laser delivery system 2 as described herein. The movable components of the laser delivery system may comprise the zoom lens capable of moving distance ZL, the X galvo mirror 96 capable of moving an angular amount Xm, and the Y galvo mirror 88 capable of moving an angular amount Ym. The movable components of the OCT system may comprise the movable OCT reference arm configured to move the reference path 106 a distance ZED. The sensor components of the laser system may comprise the video camera having X and Y pixels, Pix X and Pix Y, respectively, and sensor components of the OCT system such as the spectral domain detection as described herein. The patient support which may comprise a bed is movable in three dimensions so as to align the eye 43 of the patient P with laser system 2 and axis 99 of the system. The patient interface assembly comprises an optically transmissive structure which may comprise an interface lens 96, for example, configured to be aligned with system 2 and an axis of eye 43. The patient interface lens can be placed on the patient eye 43 for surgery, and the optically transmissive structure can be placed at a distance 162 from the objective lens 94. In many embodiments, the optically transmissive structure comprises lens 96 placed a contact lens optical distance 162 (hereinafter "CLopt"). The optically transmissive structure comprises a thickness 164, and the thickness 164 may comprise a thickness of the contact lens 96, for example. Although the optically transmissive structure comprising contact lens 96 may contact the eye 2, in many embodiments the contact lens 168 is separated from the cornea with gap 168 extending between the lens and the vertex of the cornea, such that the posterior surface of the contact lens 168 contacts a solution comprising saline or a viscoelastic solution, for example.

Figure 4B:
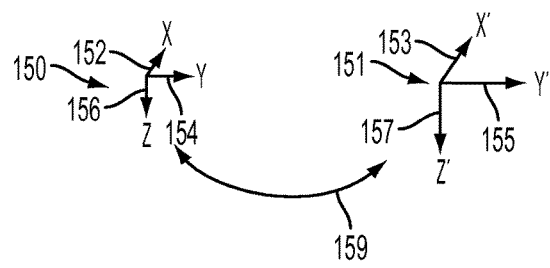
FIG. 4B shows mapping of coordinate references from an eye space coordinate reference system to a machine coordinate reference system, in accordance with many embodiments.

FIG. 4B shows mapping of coordinate references from an eye space coordinate reference system 150 to a machine coordinate reference system 151 so as to coordinate the machine components with the physical locations of the eye. The laser system 2 can map physical coordinates of the eye 43 to machine coordinates of the components as described herein. The eye space coordinate reference system 150 comprises a first X dimension 152, for example an X axis, a second Y dimension 154, for example a Y axis, and a third Z dimension 156, for example a Z axis, and the coordinate reference system of the eye may comprise one or more of many known coordinate systems such as polar, cylindrical or Cartesian, for example. In many embodiments the reference system 150 comprises a right handed triple with the X axis oriented in a nasal temporal direction on the patient, the Y axis oriented superiorly on the patient and the Z axis oriented posteriorly on the patient. In many embodiments, the corresponding machine coordinate reference system 151 comprises a first X' dimension 153, a second Y' dimension 155; and a third Z' dimension 157 generally corresponding to machine actuators, and the coordinate reference system of the machine may comprise one or more of many known coordinate systems such as polar, cylindrical or Cartesian, and combinations thereof, for example.

The machine coordinate reference 151 may correspond to locations of one or more components of system 2. The machine coordinate reference system 151 may comprise a plurality of machine coordinate reference systems. The plurality of machine coordinate reference systems may comprise a coordinate reference system for each subsystem, for example. For example, dimension 157 may correspond to movement of the z-telescope lens capable of moving distance ZL. The dimension 153 may correspond to movement of the X galvo mirror 86 capable of moving an angular amount Xm, and the dimension 153 may correspond to movement of the Y galvo mirror 88 capable of moving an angular amount Ym. Alternatively or in combination, the dimension 157 may correspond to movable OCT reference arm configured to move the reference path 106 a distance ZED, along with dimension 157 corresponding to a movement of the z-telescope for the OCT beam, and the dimension 153 and the dimension 155 may correspond to movement of the X galvo mirror 86 and the Y galvo mirror 88, respectively, for the OCT beam. The dimension 151 may correspond to X pixels of the video camera and dimension 153 may correspond to Y pixels of the video camera. The axes of the machine coordinate reference system may be combined in one or more of many ways, for example the OCT reference arm movement of the reference path 106 the distance ZED can be combined with movement of the z-telescope lens capable of moving the distance ZL, for example. In many embodiments, the locations of the components of the laser system 2 are combined when in order to map the plurality of machine coordinate reference systems to the coordinate reference system 150 of eye 43.

In many embodiments, the eye coordinate reference system is mapped from an optical path length coordinate system to physical coordinates of the eye based on the index of refraction of the tissues of the eye. An example is the OCT ranging system where measurements are based on optical thicknesses. The physical distance can be obtained by dividing the optical path length by the index of refraction of the material through which the light beam passes. Preferable the group refractive index is used and takes into account the group velocity of the light with a center wavelength and bandwidth and dispersion characteristics of the beam train. When the beam has passed through more than one material, the physical distance can be determined based on the optical path length through each material, for example. The tissue structures of the eye and corresponding index of refraction can be identified and the physical locations of the tissue structures along the optical path determined based on the optical path length and the indices of refraction. When the optical path length extends along more than one tissue, the optical path length for each tissue can be determined and divided by the corresponding index of refraction so as to determine the physical distance through each tissue, and the distances along the optical path can be combined, for example with addition, so as to determine the physical location of a tissue structure along the optical path length. Additionally, optical train characteristics may be taken into account. As the OCT beam is scanned in the X and Y directions and departure from the telecentric condition occurs due to the axial location of the galvo mirrors, a distortion of the optical path length is realized. This is commonly known as fan error and can be corrected for either through modeling or measurement.

As one or more optical components and light sources as described herein may have different path lengths, wavelengths, and spectral bandwidths, in many embodiments the group index of refraction used depends on the material and the wavelength and spectral bandwidth of the light beam. In many embodiments, the index of refraction along the optical path may change with material. For example, the saline solution may comprise a first index of refraction, the cornea may comprise a second index of refraction, the anterior chamber of the eye may comprise a third index of refraction, and the eye may comprise gradient index lens having a plurality of indices of refraction. While optical path length through these materials is governed by the group index of refraction, refraction or bending of the beam is governed by the phase index of the material. Both the phase and group index can be taken into account to accurately determine the X, Y, and Z location of a structure. While the index of refraction of tissue such as eye 43 can vary with wavelength as described herein, approximate values include: aqueous humor 1.33; cornea 1.38; vitreous humor 1.34; and lens 1.36 to 1.41, in which the index of the lens can differ for the capsule, the cortex and the nucleus, for example. The phase index of refraction of water and saline can be about 1.325 for the ultrafast laser at 1030 nm and about 1.328 for the OCT system at 830 nm. The group refractive index of 1.339 differs on the order of 1% for the OCT beam wavelength and spectral bandwidth. A person of ordinary skill in the art can determine the indices of refraction and group indices of refraction of the tissues of the eye for the wavelengths of the measurement and treatment systems as described herein. The index of refraction of the other components of the system can be readily determined by a person of ordinary skill in the art based on the teachings described herein.

Figure 5A:
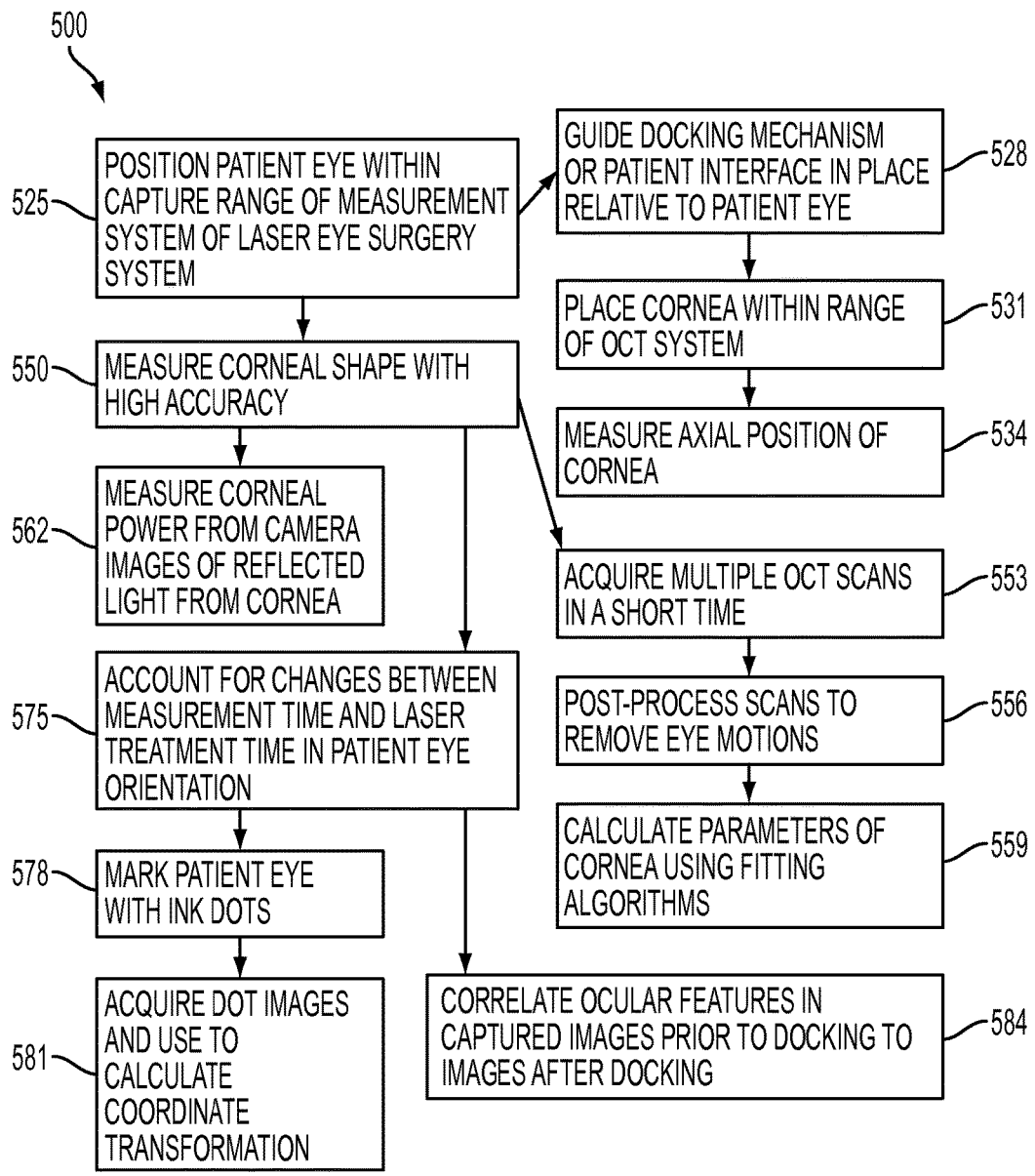
FIG. 5A shows a flow chart of a method for mapping the eye, in accordance with many embodiments.

FIG. 5A shows a flow chart of a method 500 for providing accurate and distortion-free corneal topography measurement and subsequent integration with the laser treatment, in accordance with embodiments. The method 500 comprises the following main steps. In a step 525, the patient's eye is positioned within the capture range of the measurement system of the laser eye surgery system 2 or 2A described herein. In a step 550, the measurement system is used to measure corneal shape with high accuracy. Such a measurement system may comprise the ranging subsystem 46 described above. In a step 575, any changes in the patient eye orientation that may occur between the measurement time and the laser treatment time is accounted for.

Positioning step 525: In the step 525, the patient's eye is positioned within the capture range of the measurement system of the laser eye surgery system as described herein, such as shown in FIGS. 2 and 3A, for example. Positioning of the patient for laser surgery is typically enabled by motion of the patient bed 34 or by motion of the laser system 2. Typically, the operator has manual control of the lateral and axial position, guiding the docking mechanism or patient interface 52 into place in a step 528. In the absence of a docking mechanism, an operator means for guiding the motion so that the eye, and specifically the cornea, is placed within the operative range of the measurement system may be provided. This can be accomplished with the use of subsystems of the laser system 2 or 2a described herein such as alignment guidance system 48 of laser system 2 or imaging subsystem 546 of laser system 2a. Initial patient position can be guided by a video camera, guiding the eye into lateral position by centering the video image, and into axial position by focusing the image. At this point, the cornea is placed within the capture range of the OCT system of the ranging subsystem 46 or imaging subsystem 546, typically X mm to Y mm axially, in a step 531. The OCT system can be used to measure the axial position of the cornea in a step 534, and a suitable display provides the operator guidance for final, accurate positioning. Alternatively, a visual imaging system such as a camera, a camera coupled to a microscope which may share optics with the laser system 2 or 2a, a CCD, among others may be used instead of the OCT system to facilitate the positioning step 525.

Since the video and OCT systems are typically configured to operate with the docking system, which often has additional optical elements and liquid medium in the optics path, the focusing algorithms of the laser system may be adjusted to account for operation without the docking mechanism optics and interface medium.

Measurement step 550: In the step 550, the measurement system is used to measure corneal shape with high accuracy. The laser system 2 or 2A comprises a subsystem for mapping the ocular surfaces that are being treated such as the ranging subsystem 46 having an OCT system described herein or the imaging subsystem 546. As described below, the imaging subsystem 546 may apply other modalities for mapping the ocular surfaces such as Placido imaging, Hartmann-shack wavefront sensing, confocal tomography, low coherence reflectometry, among others. The measurement step 550 can be performed once the eye is positioned correctly in the step 525 above. A fixation light can optionally be introduced to help the patient keep the eye pointed at a fixed angle. If the measurement data capture is sufficiently fast, for example, on the order of one second, a fixation light may not be necessary. In a step 553 of measurement 550, multiple OCT or other scans of the cornea surfaces can be acquired in a short time. Multiple scans can increase the confidence of obtaining good data. In a step 556, post-processing of the scans can remove potential eye motion and further improve the measurement accuracy. In a step 562 of measurement step 550, corneal power can be measured from camera images of reflected light from the cornea.

Once the cornea surfaces have been mapped, polynomial, or other fitting algorithms can be used to calculate commonly used parameters of the cornea in a step 559. Commonly used parameters include the optical power of the cornea, astigmatic axis angle, and astigmatism magnitude.

Coordinate system transfer step 575: In the step 575, any changes in the patient eye orientation that may occur between the measurement time and the laser treatment time is accounted for. Often times, it is probable that when the patient eye is docked for treatment such as with the suction ring of the patient interface 52, the eye, including its various anatomical features, will change its position relative to the laser system coordinates. This change can be a result of patient head movement, eye movement, or because of force applied during docking. In some cases, the refractive properties of the air or any liquid over the eye can distort the images of the eye. For example, the suction ring of the patient interface 52 may be filled with one or more of a solution, saline, or a viscoelastic fluid. It can be helpful to transform the corneal measurements, like the astigmatic axis angle, to a new coordinate system to account for any movement and distortion. Several means for accomplishing this are provided.

In some embodiments, the operator can mark the patient eye prior to the measurement with ink dots that are typically positioned diametrically across on the periphery of the cornea in a step 578. These dots can be acquired by the imaging camera after docking for treatment and used for calculating the coordinate transformation in a step 581.

In other embodiments, ocular features that are visible in the video images, or the OCT or other scans, taken during the measurement step are used. These features are correlated to the images taken after docking for treatment in a step 584. This correlation can be done by digital image processing algorithms, or manually by the operator. When done manually, the operator is presented by overlapped images (measurement and treatment steps) on the control screen, and the images are manually manipulated in translation and rotation until they are visibly matched. The image manipulation data can be detected by the display software and used for the coordinate transform.

Although the above steps show method 500 of providing accurate and distortion-free corneal topography measurement and subsequent integration with the laser treatment in accordance with many embodiments, a person of ordinary skill in the art will recognize many variations based on the teaching described herein. The steps may be completed in a different order. Steps may be added or deleted. For example, the shape of the cornea may be measures before, during, or after docking for treatment such as with a suction ring of the patient interface 52. Many of the steps may be repeated as often as beneficial to the method.

One or more of the steps of the method 500 may be performed with the circuitry as described herein, for example, one or more the processor or logic circuitry such as the programmable array logic for field programmable gate arrays. The circuitry may be programmed to provide one or more of the steps of method 500, and the program may comprise program instructions stored on a computer readable memory or programmed steps of the logic circuitry such as the programmable array logic or the field programmable gate array, for example.

Figure 5B:
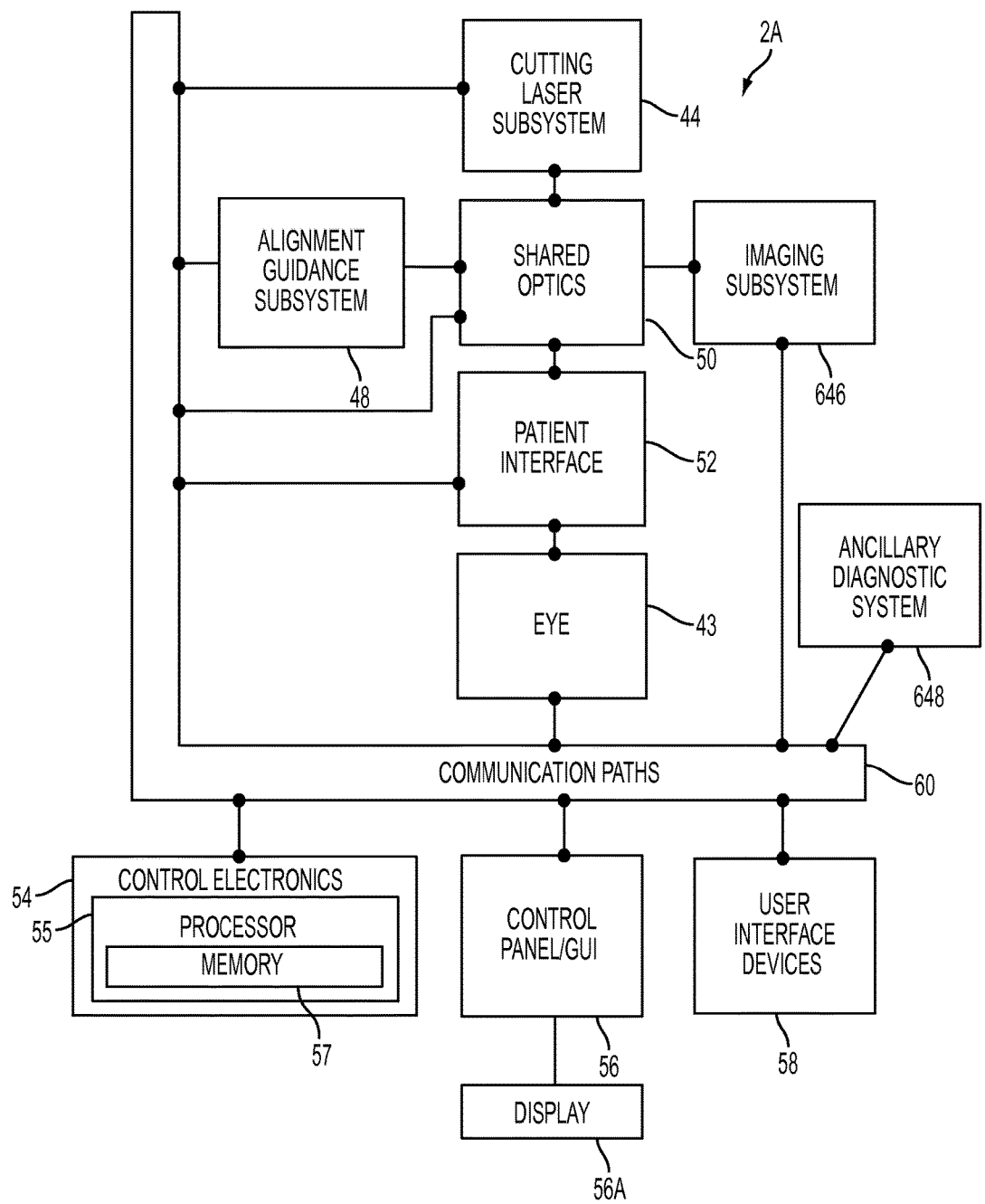
FIG. 5B shows a simplified block diagram showing a top level view of the configuration of a laser eye surgery system which can perform the method of FIG. 5A, in accordance with many embodiments.

FIG. 5B shows a laser eye surgery 2A similar to system 2 of FIG. 2 in accordance with embodiments. The laser eye surgery system 2 is similar to the laser eye surgery system 2 as described herein and comprises many of the same components. In particular, the laser eye surgery system 2A comprises an imaging subsystem 646 which may be used to visualize and image the eye 43, and the control panel/GUI 56 comprises a display 56A. The laser eye surgery system 2A may be configured to couple to a separate and distinct ancillary diagnostic system 648. For the laser eye surgery system 2, the OCT system of the ranging subsystem 46 may be used to position the patient eye in the step 525 and/or to measure the shape of the cornea in the step 550. For the laser eye surgery system 2A, the ancillary diagnostic system 648 is used to measure the shape of the cornea in the step 550. The ancillary diagnostic system 648 may apply any number of modalities to measure the shape of the eye including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack topography of the eye, a Scheimpflug image topography of the eye, a confocal tomography of the eye, or a low coherence reflectometry of the eye. The shape of the cornea can be measured before, during, or after the patient interface 52 is docked with the eye of the patient. The shape of the cornea may be measured using the ancillary diagnostic system 648 while the ancillary diagnostic system 648 is separate from the laser eye surgery system 2A, such as by being in a different room. Images captured by the ranging subsystem 46 of the laser eye surgery system 2 or the imaging subsystem 546 of the laser eye surgery system 2A and the ancillary diagnostic system 548 may be displayed with a display of the control panel/GUI 56 of the laser eye surgery system 2 or the display 56A of the laser eye surgery system 2A, respectively. The control panel/GUI 56 may also be used to modify, distort, or transform any of the displayed images.

Figure 6A:
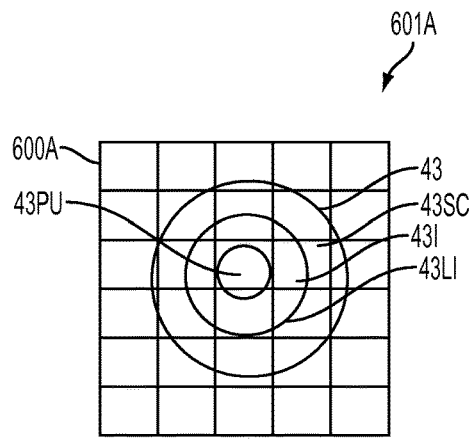
FIG. 6A shows a coordinate system overlaid on an image of the eye, in accordance with many embodiments.
Figure 6B:
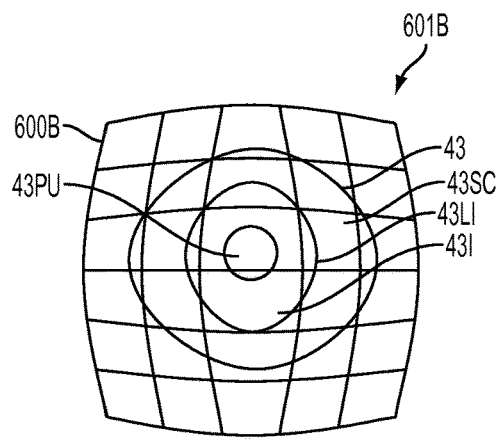
FIG. 6B shows a distorted coordinate system overlaid on the eye image of FIG. 6A to account for distortions due coupling of the eye to a patient interface, in accordance with many embodiments.
Figure 6C:
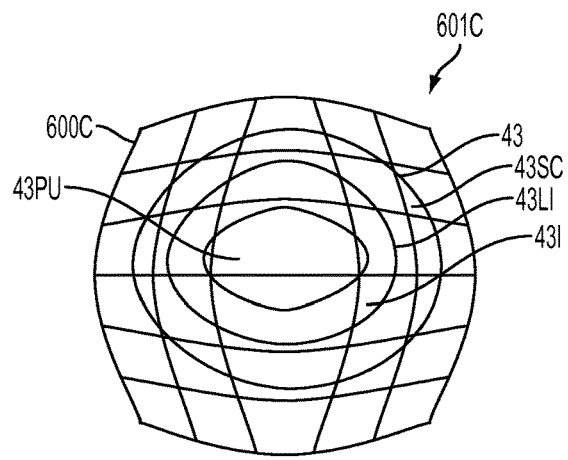
FIG. 6C shows a distorted coordinate system overlaid on the eye image of FIG. 6B to account for distortion due coupling of the eye to a patient interface as well as liquid in the patient interface disposed over the eye, in accordance with many embodiments.

FIGS. 6A to 6C show images of the eye which may be displayed for example in the display 56A of the laser eye surgery system 2A or the display of the laser eye surgery system 2, for example. The images shown illustrate distortion which may occur and the distortion may not be to scale and is provided for illustration purposes in accordance with embodiments.

FIG. 6A shows a coordinate system 600A overlaid on an image 601A of an eye EY. The image 601A of the eye 43 shows various anatomical features including the sclera 43SC, the limbus 43LI, the iris 43I, and the pupil 43PU. Similar images and biometric information can be obtained with similar maps. In many embodiments, this image 601A can be captured by the imaging subsystem 546 of the laser eye surgery system 2A. The image 601A is captured prior to coupling the eye with a suction ring of the patient interface 52 of the laser eye surgery system 2. The image 601A may most accurately represent the positions of the various tissue structures of the eye 43. The image 601A may comprise one or more of many images or measurements as described herein. A person of ordinary skill in the art will recognize that the pupil seen through the cornea/air interface comprises a virtual pupil of the eye. Although the shape and optical power of the cornea may provide distortion and magnification of the pupil and iris, a person of ordinary skill in the art can correct this distortion and magnification based on the teaching described herein and in accordance with embodiments as appropriate. For example, the virtual image of the pupil can be transformed to an eye space coordinate system 150 as described herein.

The structures shown in coordinate system 600A can be transformed to the coordinate reference system 150 of eye 2 in one or more of many ways. For example, the tissue structures shown in the image such as the limbus and the iris can be identified, and the transform to the eye coordinate reference system 150 determined based on the location of the tissue structure and depth and location in relation to correspondence optical tissue surfaces such as the surface of the cornea. The locations of the tissue structures identified in the image 601 can be determined and mapped to eye coordinate reference system 150 or to one or more coordinate reference systems as described herein.

In many embodiments, iris registration is used to determine a cyclotorsional angle of the eye. A first image of the iris can be obtained with a first camera prior to the patient interface contacting the eye, and a second image of the iris can be obtained when the patient interface contacts the eye. The first camera image of the iris can be registered with the second camera image of the iris of the patient in order to determine the cyclo torsional angle of the eye as described herein. In many embodiments, the first non-contact image of the eye comprises an image of the iris wherein the cornea of the eye magnifies and may distort the virtual image of the iris seen with the camera, and the second contact image of the eye comprises an image of the eye measured when the patient interface contacts the eye. The first image and the second image can be registered in one or more of many ways, and the processor can be configured with instructions to determine the cyclotorsional angle of the eye with instructions of an algorithm such as one or more of an image matching algorithm or a pattern recognition algorithm, for example. The processor comprising the instructions of the algorithm can be configured to identify a pattern of the first image in relation to an axis of the eye as described herein and to identify the location of the pattern in the second image in order to determine the cyclotorsional angle of the eye, for example.

In many embodiments, ray tracing through the full thickness corneal profile map can be used to correct distortions of the cornea, such as one or more of distortions of the anterior corneal surface of the posterior corneal surface. For example, when the eye has been docked and the fluid of the patient interface contacts the eye, distortions of the posterior surface of the eye can influence light rays travelling through the cornea, and distortions of images of tissue structure posterior to the posterior surface of the cornea can be corrected in response to ray tracing. The ray tracing can be performed by a person of ordinary skill in the art using Snell's law and the index of refraction of the cornea and contacting material such as air, interface fluid, or aqueous humor, for example. Alternatively or in combination, distortions of the anterior corneal surface and the corresponding distortion of images measured through the cornea can be corrected with ray tracing, for example when the cornea is exposed to air. While distortions of the anterior corneal surface can be corrected in a manner similar to the posterior surface with ray tracing, work in relation to embodiments suggests that coupling the eye to the patient interface with a fluid contacting the patient interface and having an index of refraction similar to the cornea can decrease the affect of distortions of the anterior corneal surface. Based on the teachings disclosed herein, a person of ordinary skill in the art can determine and correct for distortions of images of the eye related to corneal distortions with ray tracing and corneal profile maps as described herein, for example.

In many embodiments one or more of the first image or the second image is adjusted in response to distortion of the one or more of the first image or the second image. The distortion can be related to the index of refraction viscous fluid into the patient interface that affects the optical properties of the image of the eye, or the distortion of the optical delivery system, and combinations thereof. In many embodiments, the distortion of the cornea can be determined in response to a thickness profile of the cornea, and aberrations of the image introduced by the thickness profile of the cornea corrected.

FIG. 6A1 shows corneal profile data 610A of cornea 43C for the coordinate system and image of FIG. 6A. The corneal profile data 610A comprises a plurality of corneal profiles from the tomography system taken with the patient interface away from the eye as in FIG. 6A. The plurality of corneal profiles comprises a first corneal profile 612A, a second corneal profile 614A and a third corneal profile 616A. Additional corneal profiles can be taken. The cornea profiles can be obtained with tomography scans along a plane for example, and detection of the corneal surface. The corneal surface can be fit as described herein, for example with polynomials as described herein. The fit corneal surface can be used to determine the corneal topography and treatment parameters as described herein. The corneal profile data may comprise coordinate system 600A, for example.

FIG. 6B shows a distorted coordinate system 600B overlaid on the eye image 601B of the eye 43. The image 601A of the eye 43 shows various anatomical features including the sclera 43SC, the limbus 43LI, the iris 43I, and the pupil 43PU. In many embodiments, this image 601B is taken of the eye by a visual imaging system of the laser eye surgery system 2. This image 601B is taken when the anterior surface of the eye 43 is coupled with a suction ring of the laser eye surgery system 2 to expose the anterior surface to air. The suction ring may distort the tissue structures of the eye 43 when placed thereon. The locations of the various tissue structures of the eye, such as one or more structures of the iris, in relation to the distorted coordinate system 600B can be mapped to their respective locations the coordinate system 600A in image 601A to account for this distortion.

FIG. 6C shows a distorted coordinate system 600C overlaid on the eye image 601C of the eye 43. The image 601C of the eye 43 shows various anatomical features including the sclera 43SC, the limbus 43LI, the iris 43I, and the pupil 43PU. In many embodiments, this image 601C is taken of the eye by a visual imaging system of the laser eye surgery system 2. This image 601C is taken when the anterior surface of the eye 43 is coupled with a suction ring of the laser eye surgery system 2 and the suction ring is filled with a liquid such as saline or viscoelastic substance. In addition to distortion from interfacing with the suction ring, the refractive properties of the liquid may also distort light reflecting back from the anterior surface of the eye EY. The locations of the various tissue structures of the eye, such as one or more structures of the iris, in relation to the distorted coordinate system 600C can be mapped to their respective locations the coordinate system 600A in image 601A to account for these distortions. Alternatively or in combination, the structures can be mapped to eye coordinate reference system 150

FIG. 6C1 shows corneal profile data 610C of cornea CO for the coordinate system and image of FIG. 6C. The corneal profile data 610C can be provided with mapping of the corneal profile data 610A, or based on a second set of similar measurements. The corneal profile data 610C comprises a plurality of corneal profiles from the tomography system taken with the patient interface away from the eye as in FIG. 6A. The plurality of corneal profiles comprises a first corneal profile 612C, a second corneal profile 614C and a third corneal profile 616C. Additional corneal profiles can be taken. The cornea profiles can be obtained with tomography scans along a plane for example, and detection of the corneal surface. The corneal surface can be fit as described herein, for example with polynomials as described herein. The corneal profile data 610C may a coordinate system 600C overlaid. The corneal profile data 610C of coordinate system 600C may be mapped to eye coordinate reference 150 as described herein, for example. Alternatively or in combination, the corneal profile data 610C may comprise eye coordinate reference 150 as described herein, for example when the treatment is mapped based on the patient interface coupled to the eye.

In many embodiments, the non-distorted image 601A is modified to provide a distorted first image with a distortion similar to that in images 601B or 601C. The distorted image 601A may then be displayed on the display 56A or other display of the laser eye surgery system 2 or 2A. A user of the laser eye surgery system 2 or 2A can adjust one or more of a location or an angle of the distorted image 601A on the display 56A or other display. Locations of a plurality of laser beam pulses from the cutting laser subsystem 44 can then be adjusted in response to the location or the angle of the first distorted image 601A on the display 56A or other display. In some embodiments, the distorted first image 601A is overlaid on the distorted image 601B or 601C on the display 56A or other display to determine the position and the angle of the eye for treatment. A processor of the laser eye surgery system 2 or 2A can determine the position and the angle of the distorted first image 601A on the display in response to user input to adjust the locations of the plurality of laser beam pulses from the cutting laser subsystem 44.

FIG. 6A2 shows corneal thickness profile data for the coordinate system and images of FIGS. 6A and 6A1. The corneal profile data 610A comprises a plurality of corneal thickness profiles from the tomography system taken with the patient interface away from the eye as in FIG. 6A. The plurality of corneal profiles comprises a first corneal thickness profile 617A, a second corneal thickness profile 618A and a third corneal profile 619A. Additional corneal profiles can be taken.

Each of the thickness profiles may comprise a difference between an anterior surface profile and a posterior surface profile, for example. The first corneal thickness profile 617A may comprise a difference between a first anterior surface profile 612A and a first posterior surface profile 611A. The second corneal thickness profile 618A may comprise a difference between second anterior surface profile 614A and a second posterior surface profile 613A. A third corneal profile 619A may comprise a difference between third anterior surface profile 616A and a third posterior surface profile 615A. Additional corneal profiles can be taken.

Each of the corneal thickness profiles coordinate system 600AC of can be mapped to the physical eye coordinate reference system 150.

FIG. 6C2 shows corneal thickness profile data for the coordinate system and images of FIGS. 6C and 6C1. The corneal thickness profile data 610A comprises a plurality of corneal thickness profiles from the tomography system taken with the patient interface away from the eye as in FIG. 6C. The plurality of corneal profiles comprises a first corneal thickness profile 617C, a second corneal thickness profile 618C and a third corneal profile 619C. Additional corneal profiles can be taken.

Each of the thickness profiles may comprise a difference between an anterior surface profile and a posterior surface profile, for example. The first corneal thickness profile 617C may comprise a difference between a first anterior surface profile 612C and a first posterior surface profile 611C. The second corneal thickness profile 618C may comprise a difference between second anterior surface profile 614C and a second posterior surface profile 613C. A third corneal profile 619C may comprise a difference between third anterior surface profile 616C and a third posterior surface profile 615C. Additional corneal profiles can be taken.

Each of the corneal thickness profiles coordinate system 600C of can be mapped to the physical eye coordinate reference system 150.

FIG. 6A3 shows a corneal thickness profile map 620A for the coordinate system and images of FIGS. 6A, 6A1 and 6A2. The thickness profile map generally comprises a representation of three dimensional thickness profile data of the cornea, and may comprise three dimensional thickness data of the cornea. For example, the thickness profile data may comprise a two dimensional array in which the thickness of the cornea is stored for each two dimensional location of the array.

The corneal thickness profile map 620 can be determined based on the first corneal thickness profile 617A, the second corneal thickness profile 618A and the third corneal thickness profile 619A, for example. The corneal thickness profile map 620A can be shown in relation to the pupil 43PU and the limbus 43LI. The corneal thickness profile map 620A can be displayed to the user in one or more of many known formats such as with color coding of thicknesses or with equal depth contour lines. The equal depth contour lines may comprise a first equal depth contour line 622A, a second equal depth contour line 624A. The corneal thickness profile data can be fit as described herein, for example with a polynomial as described herein, in order to provide the corneal thickness profile map 620. The maps can be obtained with reference to coordinate system 600A and mapped to eye coordinate reference system 150, for example.

FIG. 6C3 shows a corneal thickness profile map 620C for the coordinate system and images of FIGS. 6C, 6C1 and 6C2. The corneal thickness profile map 620C can be determined based on the first corneal thickness profile 617C, the second corneal thickness profile 618C and the third corneal thickness profile 619C, for example. The corneal thickness profile map 620C can be shown in relation to the pupil 43PU and the limbus 43LI. The corneal thickness profile map 620C can be displayed to the user in one or more of many known formats such as with color coding of thicknesses or with equal depth contour lines. The equal depth contour lines may comprise a first equal depth contour line 622C, a second equal depth contour line 624C. The corneal thickness profile data can be fit as described herein, for example with a polynomial as described herein, in order to provide the corneal thickness profile map 620. The maps can be obtained with reference to coordinate system 600C and mapped to eye coordinate reference system 150, for example.

Work in relation to embodiments of the present disclosure suggest that the corneal thickness profile maps and data as disclosed herein are resistant to mechanical deformation when the suction ring is placed on the eye, and can be used to align the eye about the cyclotorsional axis, for example. The corneal thickness profile maps can be particularly well suited to align eyes having prior refractive surgery, such as eyes that have received LASIK or PRK or other refractive surgery, for example.

Figure 7A:
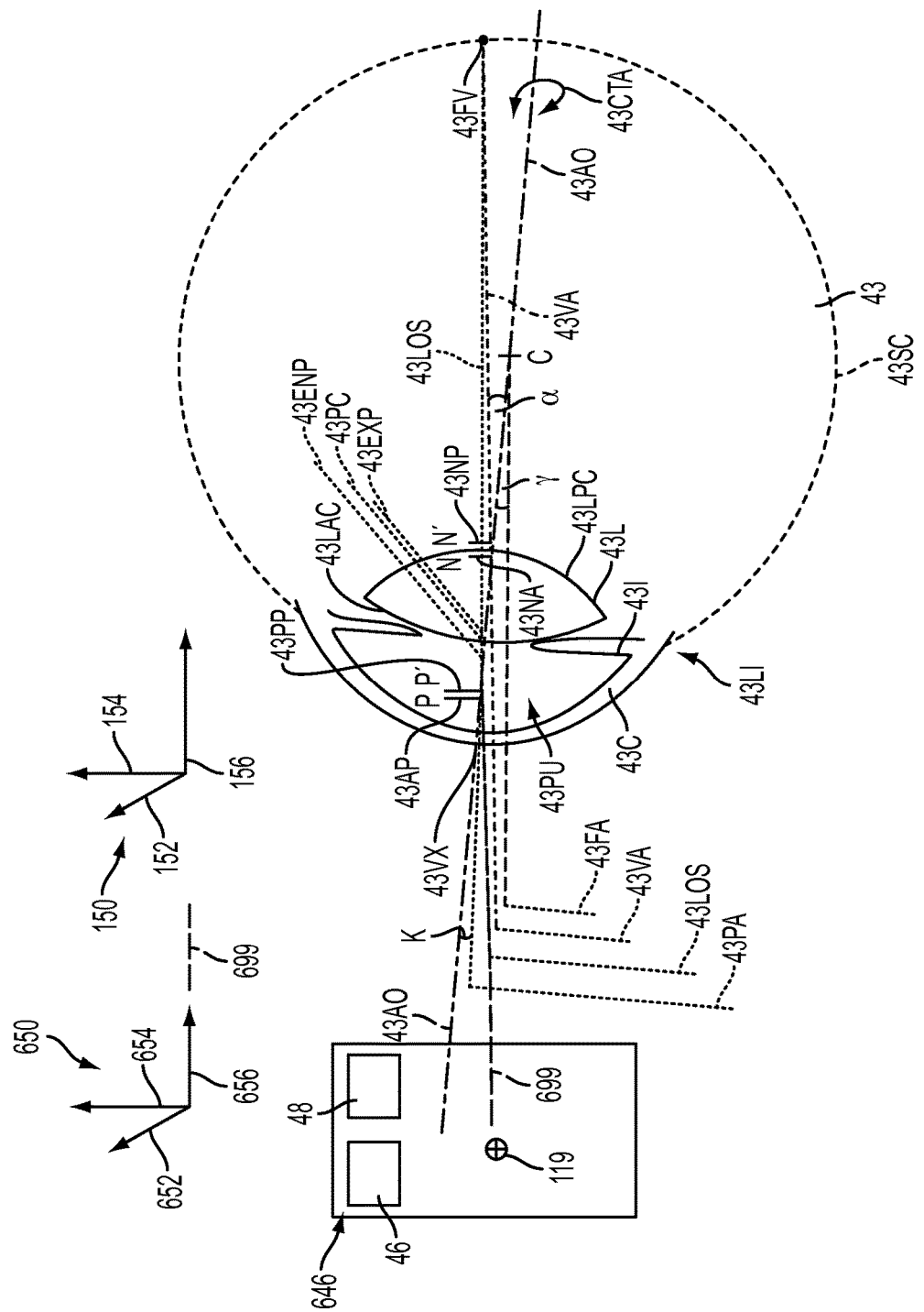
FIGS. 7A and 7B show side views of axes of the eye when the eye views a fixation target and the eye is measured prior to contacting a patient interface, in accordance with many embodiments.
Figure 7B:
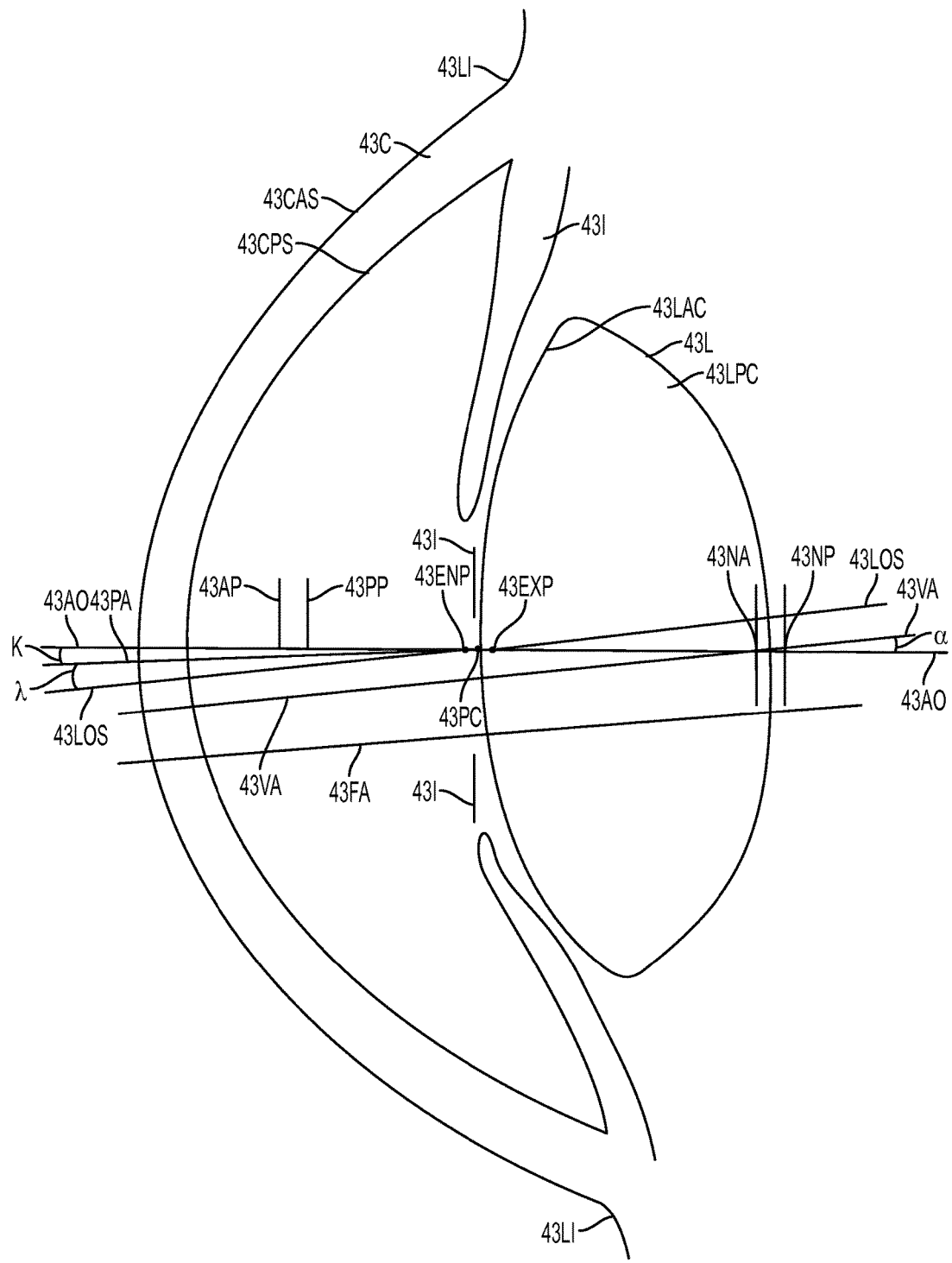

FIGS. 7A and 7B show side views of a plurality of axes of the eye 43 when the eye views a fixation target and the eye is measured with an imaging system 646 prior to contacting a patient interface. The imaging system 646 can be used to measure one or more optical structures of the eye, and the processor of the laser system can be used to determine locations of the incisions in response to locations of the one or more optical structures. The imaging system 646 may comprise one or more components of the ranging system 46 as described herein alignment and may comprise one or more components of guidance system 48 as described herein, for example the OCT system of ranging system 46 and video camera of alignment guidance system 48. Alternatively or in combination, the imaging system 646 may comprise one or more components of separate diagnostic system 648 as described herein. The imaging system 646 may by located on laser system 2, or may comprise separate and distinct ancillary diagnostic system 648, and combinations thereof, for example.

Imaging system 646 can be aligned with one or more axes of the eye as described herein, for example with the patient viewing the fixation light 119. In many embodiments, the patient views fixation light 119, and the imaging system 646 is aligned with the eye in one or more of many ways as described herein.

Imaging system 648 comprises fixation light 119 as described herein for the patient to view when measurements are obtained. The fixation light 119 allows the patient to fixate in order to align the axes of the coordinate system 150 of the eye with one or more reference axes of the coordinate system 650 of imaging system 646. The imaging system may 648 comprise a measurement axis 699 that extends along an optical axis of the measurement system, and the fixation light 119 can be located along the measurement axis 699 to align the eye with the measurement system. The measurement axis 699 may comprise axis 99 of the optical delivery system of laser system 2 when laser system 2 is used for measurements of the eye prior to contacting the eye with the patient interface. The initial measurement reference coordinate system 650 of imaging system 646 comprises a first dimension 652, a second dimension 654 and a third dimension 646, for example. The dimensions of the coordinate system 650 may comprise a right handed triple orthogonal coordinate reference system, for example. The third dimension 646 may comprise the measurement axis 699 of the measurement system, for example. For initial measurements of the eye prior to the patient interface contacting the eye, the coordinate reference system may comprise the eye coordinate reference system 150 as described herein. When the eye has been contacted with the patient interface, the eye coordinate reference system 150 for treatment with the laser can be one or more of rotate or translated with respect to the initial measurement reference coordinate system 650.

The imaging system 646 includes sensors to image one or more tissue structures of the eye and can be used to determine one or more axes of the eye as described herein. The imaging system 646 can image and profile one or more structures of the eye as described herein, such as one or more of the cornea of the eye 43C, the anterior surface of the cornea, the posterior surface of the cornea, the iris of the eye 43I, the pupil of the eye 43PU, the natural pupil of the eye 43PUN, the lens of the eye 43L, the anterior capsule of the lens 43LAC, the posterior capsule of the lens 43LPC, the entrance pupil of the eye 43ENP, the natural entrance pupil of the eye, the vertex of the cornea 43VX. In many embodiments, tomography of the cornea is combined with surface topography of the cornea and the video camera images of the cornea to determine one or more axes of the eye 43.

The vertex 43VX of the cornea may comprise a central part of the cornea located along the optical axis 43AO of the eye that extends substantially perpendicular to the plane of the eye, and may comprise a center of the cornea as determined in response to a measurement of the limbus extending around the perimeter of the cornea.

The imaging system 646 can be used to determine one or more optical structures of the eye when the eye fixates naturally without contacting the patient interface in order to determine locations of the one or more optical structures of the eye when the eye contacts the patient interface. In many embodiments, the imaging system 646 is used to determine one or more of the optical axis of the eye 43AO, the center of curvature of the anterior corneal surface, the center of curvature of the posterior corneal surface, the center of curvature of the lens capsule anterior surface, or the center of curvature of lens capsule posterior surface. The optical axis of the eye may comprise a straight line extending from the center of curvature of the anterior surface of the cornea to the center of curvature of the posterior surface of the posterior lens capsule. In many embodiments, the centers of curvature may not lie on a straight line, and the processor of the laser eye surgery system can be used to determine the optical axis 43AO with an orientation and location that decreases the distance from the optical axis to each of the center of curvature of the cornea anterior surface, the center of curvature of the cornea posterior surface, the center of curvature of the lens capsule anterior surface, and center of curvature of the capsule posterior surface, for example, with least squares fitting of the optical axis to the centers of curvature for example.

The curvatures and the centers of curvature of the eye can be used to determine the locations of the cardinal points of the eye comprising the object point where the fixation light 119 is located, the image point where the center of the fovea 43FV is located when the patient views the fixation light, the anterior nodal point 43NA of the eye, the posterior nodal point 43NP, the anterior principal point 43AP, and the posterior principal point 43PP. One or more of these cardinal points of the eye can be used to determine incision locations of the pulsed laser beam, and these cardinal points and the corresponding axes can be shown on a display to a user to determine locations on the incisions, in accordance with many embodiments.

One or more of the natural entrance pupil 43ENP or the natural exit pupil 43EXP of the eye can be determined and may be used to determine locations of the incisions with the pulsed laser beam. The entrance pupil 43ENP of the eye comprises a virtual image of the pupil of the eye as seen by light rays entering the eye from the fixation light 119. The natural exit pupil of the eye 43EXP may comprise the image of the iris 43I formed by lens 43L as seen from the fovea.

Referring to FIG. 7B, the cardinal points of the eye and image forming axes of the eye are shown in detail. The iris 43I can be seen in relation to the physical pupil center 43PC, the location of the center of the entrance pupil 43ENP along the optical axis 43AO, and the location of the center of the exit pupil 43EXP along the optical axis 43AO. The visual axis 43VA is shown extending from the fixation light to the anterior node 43NA, and from the posterior node 43NP to the center of the fovea, with the first and anterior node separated from the second and posterior node along the optical axis 43AO. The line of sight 43 LOS can be seen extending from the fixation light 119 to the center of the entrance pupil 43ENP, and from the center of the exit pupil 43EXP to the center of the fovea, with the center of the entrance pupil and the center of the exit pupil located along the optical axis.

The axes of the eye that can be identified and determined with the imaging system 646 or the processor of laser system (and combinations thereof) include a fixation axis 43FA, a visual axis 43VA, a line of sight 43LOS, a pupillary axis 43PA and an optical axis 43AO.

The 43FA fixation axis of the eye may comprise an axis extending from the fixation light 119 through a center of rotation of the eye 43C.

The line of sight 43LOS may comprise a straight line extending from the fixation light through the center of the entrance pupil 43EP when the patient views the fixation light. The line of sight 43LOS may also comprise a straight line extending from the fovea to the exit pupil of the eye when the patient views the fixation light. The entrance pupil P comprises a virtual image of the pupil that the light rays from the fixation light entering the eye are directed toward, and can be imaged with the video camera of the alignment assembly 48 as described herein. The exit pupil 43EXP comprises The pupillary axis 43PA may comprise a line perpendicular to the surface of the cornea, passing through the center of the pupil, for example.

The visual axis of the eye may comprise one or more of many axes of the eye, in accordance with embodiments as described herein. In many embodiments the visual axis comprises an axis extending from the fixation light 119 to the anterior optical nodal point of the eye N, in which the anterior optical nodal point of the eye N is located along the optical axis of the eye 43AO. The visual axis of the eye can extend from the posterior nodal point of the eye 43NP to the center of the fovea FV, with an angle α (Alpha), extending between the optical axis and the visual axis.

Alternatively, the visual axis of the eye may comprise an imaginary straight line passing from the fixation light located at the midpoint of the visual field, through the pupil, to the center of the fovea 43FV when the patient fixates on the fixation light, for example. A person of ordinary skill in the art, based on the teachings of the present disclosure, will recognize that the imaginary straight line of the visual axis can be approximated by a line extending between the anterior nodal point of the eye and the posterior nodal point of the eye, for example approximated with a single "nodal" point of the eye. For example, the eye may comprise a single index of refraction to provide the single nodal point of the eye, for example with Gullstrand's reduced schematic eye model. However, in many embodiments as described herein the eye comprises two or more indices of refraction, for example three or more indices of refraction, and the image guided treatment as described herein will provide treatment planning to the user in response to identification of the visual axis of the eye extending from the anterior nodal point of the eye to the fixation target and from the posterior nodal point of the eye to the fovea.

An angle γ (Gamma) can extend between the optical axis and the fixation axis, for example. An angle κ (Kappa) can extend between the visual axis 43VA and the pupillary axis 43PA, for example. Alternatively, angle κ (Kappa) can be defined so as to extend between the pupillary axis 43PA and the line of sight, for example. In many embodiments, the pupillary axis comprises a line extending normal to the surface of the cornea and through the center of the pupil, for example.

Figure 7C:
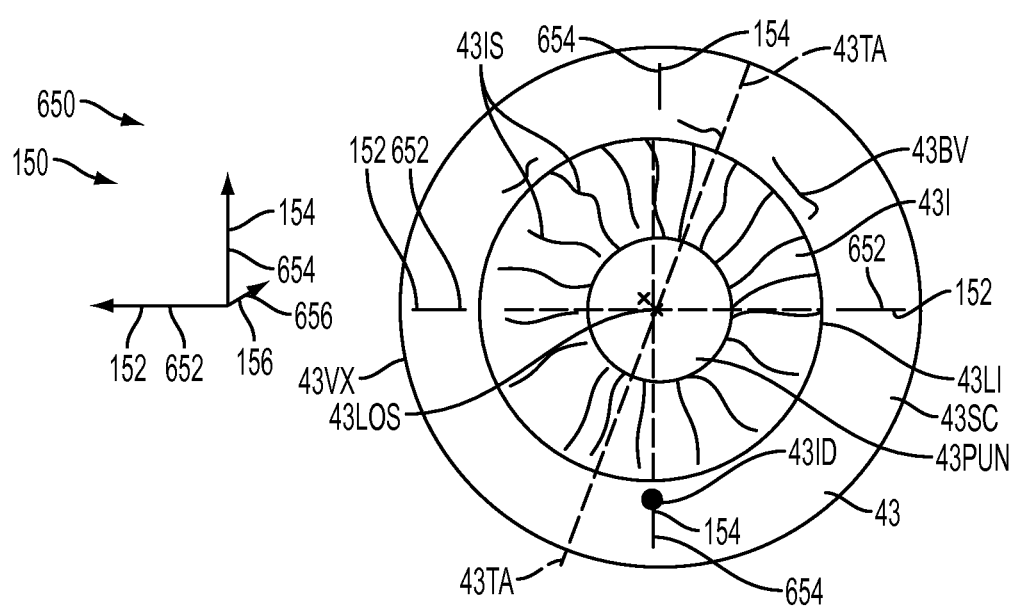
FIG. 7C shows an anterior view of an eye as in FIGS. 7A and 7B, in accordance with embodiments.

FIG. 7C shows an anterior view of an eye 43 as in FIGS. 7A and 7B. The view shows structure of the eye similar to the views of FIGS. 7A and 7B. In many embodiments, the images of FIGS. 7A and 7B are obtained with a tomography system such as an OCT system and the image of FIG. 7C is obtained with a video camera such as an alignment camera as described herein. The dimensions of coordinate system 650 can be aligned for each of the measurement systems of measurement system 150, and can define the measurement axis of the eye.

The image of the eye may comprise one or more structures that can be used to identify one or more treatment axes of the eye and structures and optical tissue surfaces of the eye as described herein, which can be combined with data from one or more of the tomography or the tomography system as described herein to determine treatment axis and alignment of the eye, for example. The structure of the image of the eye may comprise an image of a marker of the eye such as an ink dot 43ID placed by a health care provider such as a physician or an ophthalmic technician, which can be used for alignment of the eye such as cyclo torsional alignment of the eye around one or more optical axes of the eye as described herein. The ink dot 43ID may comprise a plurality of ink dots, for example a plurality of ink dots on a plurality of opposing sides of the pupil. The structure of the image of the eye may comprise images of blood vessels 43BV that can be used for alignment of the eye, such as cyclo torsional alignment of the eye around one or more axes of the eye as described herein, for example. The structure image of the eye may comprise structure of the iris that can be used for alignment of the eye, such as torsional alignment of the eye around one or more axes of the eye as described herein, for example.

The eye may comprise a treatment one or more treatment axes, such as treatment axis 43TA, and the location of treatment axis 43TA can depend upon the layer and tissue structure of the eye being treated, for example the lens or the cornea. The treatment axis 43TA may comprise an axis of an aberration of the eye such as an astigmatism of the eye or a higher order aberration of the eye such as coma or trefoil of the eye, for example. The treatment axis 43A can be identified by the system user such as a physician, and can be defined to have a center corresponding to one or more of the optical axes as described herein such as one or more of the vertex of the cornea, the line of sight of the eye, the visual axis of the eye, or the visual axis of the eye extending from the anterior node of the eye. Alternatively or in combination, the axis identified by the user can be different for the type of treatment of the eye. For example, with arcuate incisions such as limbal relaxing incisions, the treatment axis may comprise the line of sight or the vertex of the cornea, or other axis as described herein. With an intraocular lens to be placed, the treatment axis may comprise a center of the real pupil, a center of the line of sight, a center of the visual axis extending from an anterior node of the eye, or other axis as described herein, for example. Merely by way of example in accordance with embodiments, the treatment axis 43A is shown with reference to the line of sight 43 LOS corresponding to the center of the entrance pupil when the patient fixates on light 119 and the eye is viewed with the video camera as described herein, for example.

Each of images 7A to 7C can be shown on the display as described herein to the user for planning the locations of incisions in relation to one or more user identified axes of the eye as described herein, for example.

Figure 7D:
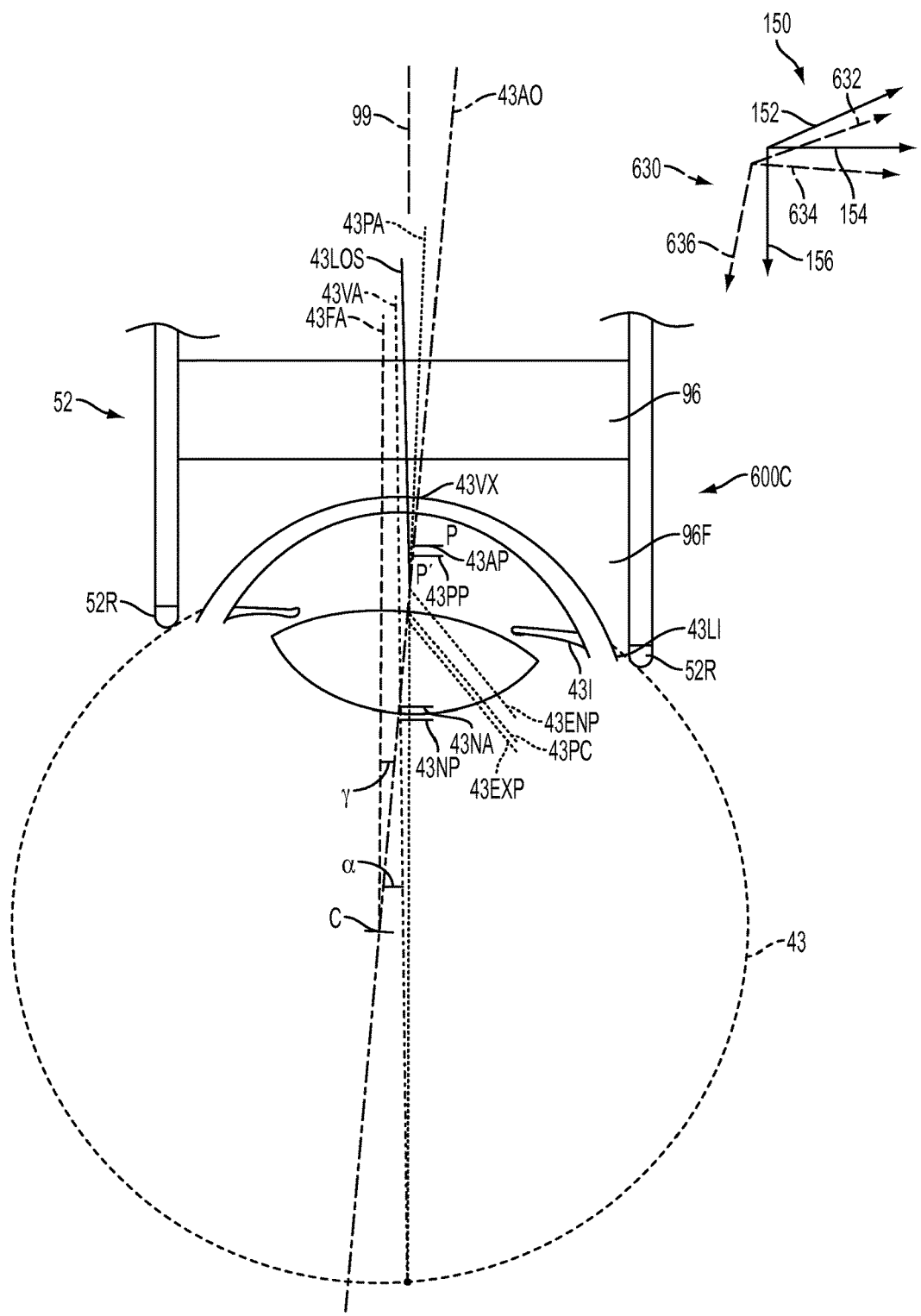

FIGS. 7D and 7E show an eye as in FIGS. 7A to 7C coupled to a patient interface for treatment, in which the eye has one or more of rotated or translated relative to one or more of three axes of the measurement system eye as described herein. The structures of the eye corresponding coordinate system 650 having dimensions along the axes of the eye for the initial measurements of the eye, such as dimension 652, dimension 654 and dimension 656 have rotated and translated with respect to the coordinate reference system 150 of the eye 43. The coordinate reference system 150 may comprise the coordinate reference system when the eye is coupled to the patient interface, for example contacts the patient interface, as described herein. The initial measurement coordinate reference system 650 comprising first dimension 652, second dimension 654 and third dimension 656 are show rotated and translated with respect to the eye coordinate reference system 150 when the patient interface is coupled to the eye with contacts to eye as described herein.

Referring to FIG. 7D, the optical axis of the eye 43AO can be aligned so as to extend away from the axis 99 of the optical delivery system of the patient interface and laser system. The alignment of the axes of the eye to the axis 99 of the optical delivery system can be determined in one or more of many ways.

The physician can perform one or more of many steps to align the eye 43 with axis 99 of the optical delivery system of the patient interface of the laser system as described herein. In many embodiments, the axis 99 of the optical delivery system is shown on the display, for example with a reticle, and the reticle on the display used to align the eye with the axis 99 of the optical delivery system. The reticle shown on the display may correspond to dimension 152, 154 and 156 of eye coordinate reference frame 150 when the eye contacts the patient interface. For example, the patient can be asked to view the fixation light 119 and the laser system aligned with one or more structures of the eye as described herein, such as the limbus of the eye, for example. Alternatively or in combination, the axis 99 can be aligned with the vertex of the cornea, for example. In many embodiments, the physician can align the axis 99 with the center of the light reflected from the front surface of the cornea, for example. Alternatively or in combination, the axis 99 of the system can be shown on the display when the patient views the fixation light, and a location of the vertex 43VX from prior to contact can be shown on the display and the Referring again to FIGS. 7D and 7E, the structures of the eye 43A are shown rotated and translated for the measurements prior to the eye contacting the patient interface and the measurements with the eye contacting the patient interface. The ink dot 43ID is shown rotated and translated with respect to the location prior to the interface contacting the eye. The blood vessels 43BV are shown rotated and translated with the respect to the locations prior to contacting the eye with the patient interface. The treatment axis 43TA is shown rotated and translated with respect to the locations determined prior to the patient interface contacting the eye.

One or more of the tissue structures of the eye can change when the eye has contacted the patient interface. With surgery, the eye may comprise a dilated pupil PUD that can dilate eccentrically with respect to the natural pupil PUN. The location of the capsulorhexis incision 43CX can be determined based on the natural pupil of the eye, for example. In many embodiments, the capsulorhexis incision is centered on the natural line of sight 43LOSN determined from the initial images prior to contacting the eye with the patient interface, for example. Alternatively or in combination, the capsulorhexis incision may be centered on the visual axis of the eye 43VA extending from the anterior nodal point of the eye as described herein. The location of the vertex 43VX of the cornea determined without contact to the eye can be shown on the display as the location of the vertex of the cornea can change, for example when the patient interface distorts the cornea.

The locations of the limbal relaxing incisions 43LRI can be determined in one or more of many ways and can be centered on the natural line of sight 43LOSN corresponding to the line of sight 43LOS determined prior to contacting the eye, for example. Alternatively or in combination, the locations of the limbal relaxing incisions can be centered on the vertex 43VX of the cornea determined prior to the patient interface contacting the cornea, and the location of corneal vertex 43VX prior to the patient interface contacting the cornea can be displayed to the user to for use as a reference point to center the limbal relaxing incisions 43LRI, for example.

In response to movement of the eye relative to the initial measurement axis and the axis 99 of the laser system, the treatment axis 43TA of the eye can be seen as rotated in relation to the coordinate reference frame 150 of the eye coupled to the laser system.

FIG. 7F shows rotation and translation of the measurement coordinate reference system 650 relative to the eye coordinate reference system 150 when the eye has contacted the patient interface, in which the rotation and translation of the measurement system 650 prior to contact with the patient interface corresponds to rotation and translation of the eye relative to the coordinate system 150 when the patient interface contacts the eye. The rotation and translation of one or more of the tissue structures of the eye determined with the natural pupil and vision of the eye can be correspondingly rotated and translated and provided on a display for the physician to determine the treatment of the eye. The locations and orientations of the tissue structures of the eye determined with measurements of the eye prior to coupling with the patient interface can be mapped from the coordinate system 650 to the coordinate 150 and shown on the display with the image of the eye coupled to patient interface. This allows the user to determine the treatment with the coordinate reference 150 with the eye contacting the patient interface, while showing the locations of the structures of the eye from used for natural vision from the coordinate reference frame 650 on the patient interface.

FIG. 7G shows an optical schematic of the eye as in FIGS. 7A and 7B, with structures of eye including the cardinal points of the eye and axes of the eye useful for vision. In many embodiments, one or more structures of the optical schematic of the eye are projected onto the display and aligned with the image of the eye shown on the display in order for the user to plan the incisions and surgical treatment of the eye.

In many embodiments, one or more of the tissue structures of each of images 7A to 7G can be shown on the display to the user for planning the locations of incisions as described herein, such as the location of the nodal points of the eye along the optical axis of the eye, the line of sight of the eye, the vertex of the cornea, and the visual axis extending from the anterior nodal point of the eye. For example, the one or more structures of the optical schematic of the eye determined from measurements prior to contacting the eye can be shown on the display aligned with images of the eye obtained when the patient interface has contacted the eye, in order for the surgeon to determine the locations of incisions in alignment with the one or more structures of the eye determined from measurements obtained prior to contact with the patient interface when the patient interface contacts the eye. Alternatively or in combination, the one or more optical structures of the eye shown on the display can be determined in response to measurements obtained when the patient interface contacts the eye, for example for comparison with locations of the one or optical structures determined from measurements obtained prior to the patient interface contacting the eye.

Figure 8A:
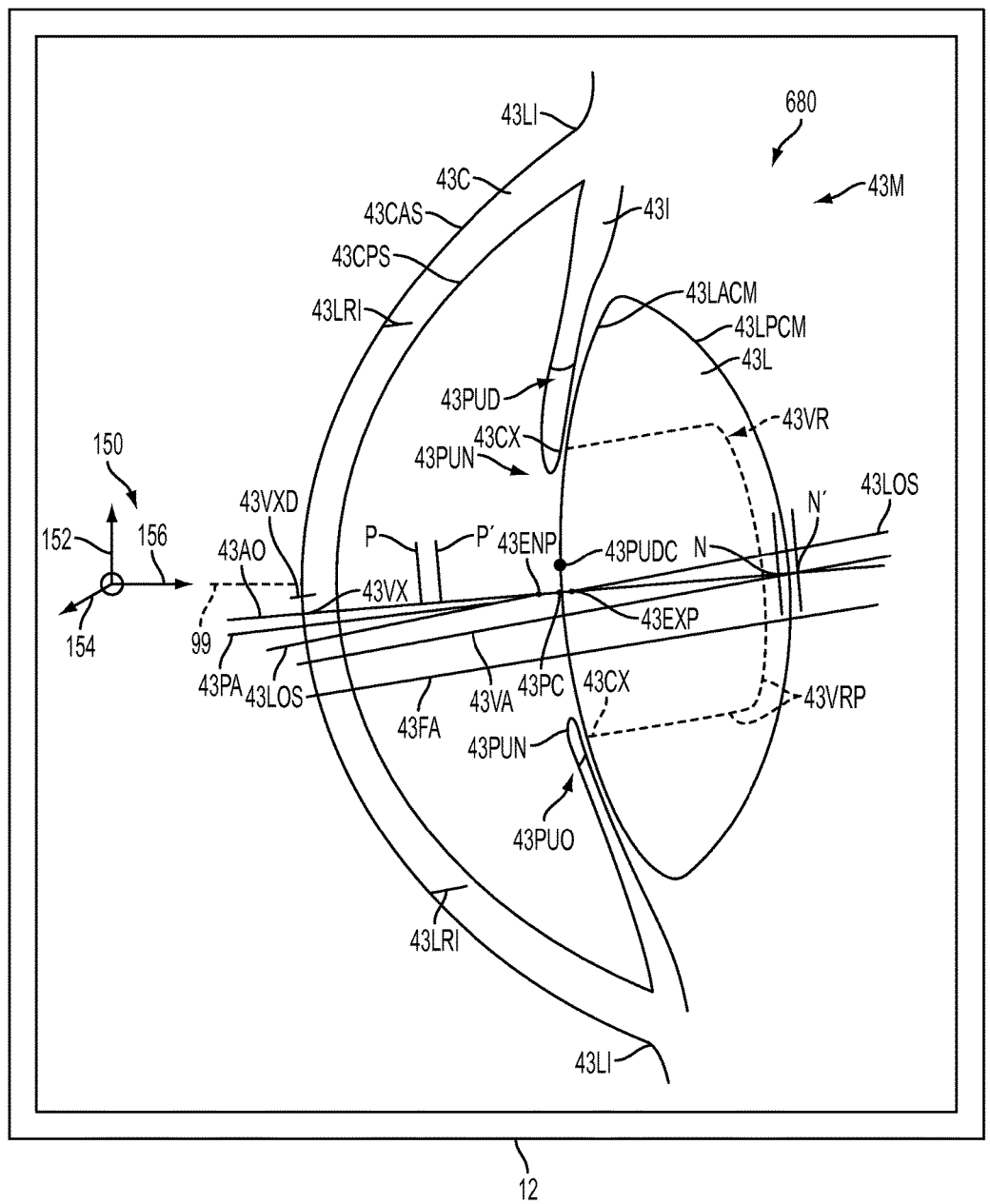
FIGS. 8A, 8B and 8C show images of a user interface display configured to show one or more optical structures of the eye to position the laser beam pulses of a tissue treatment in order to treat the eye, in accordance with embodiments.
Figure 8B:
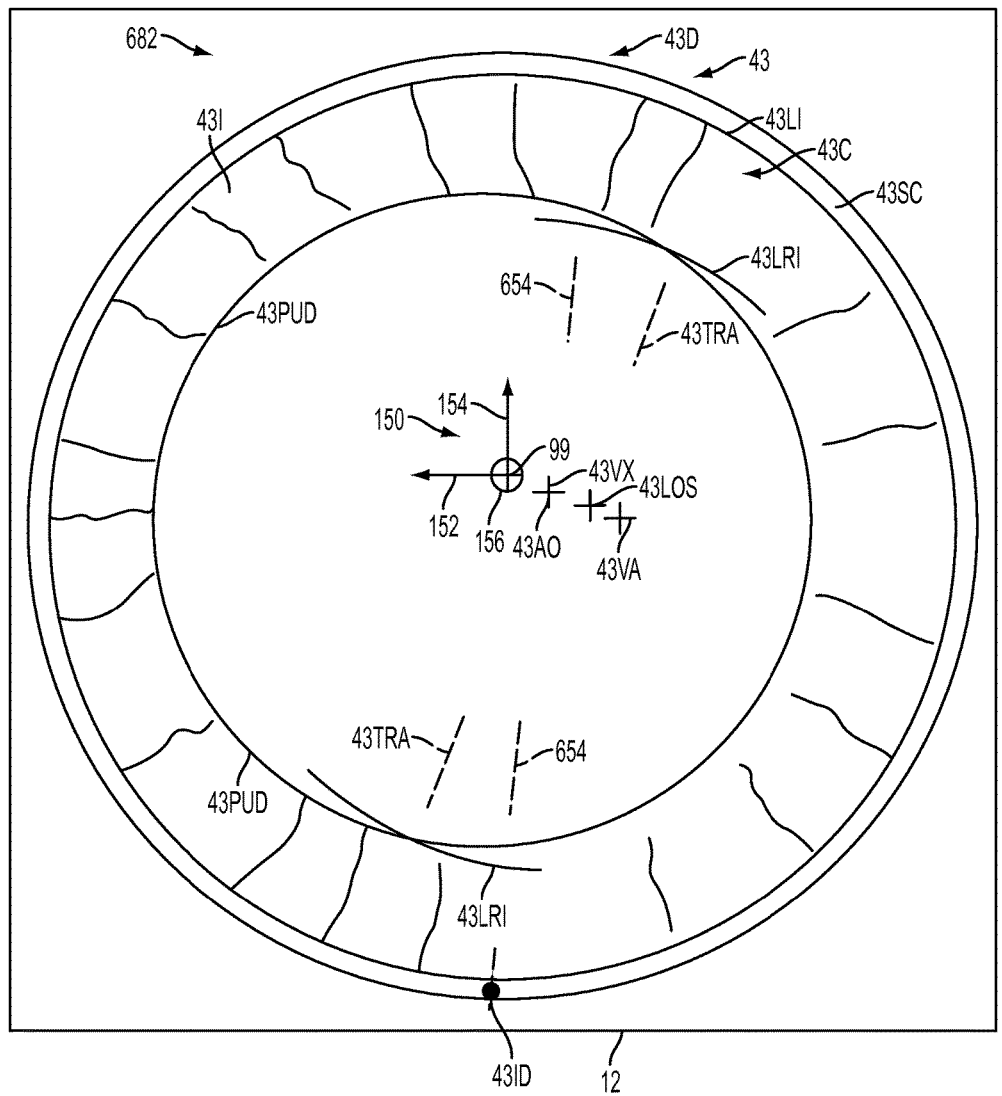
Figure 8C:
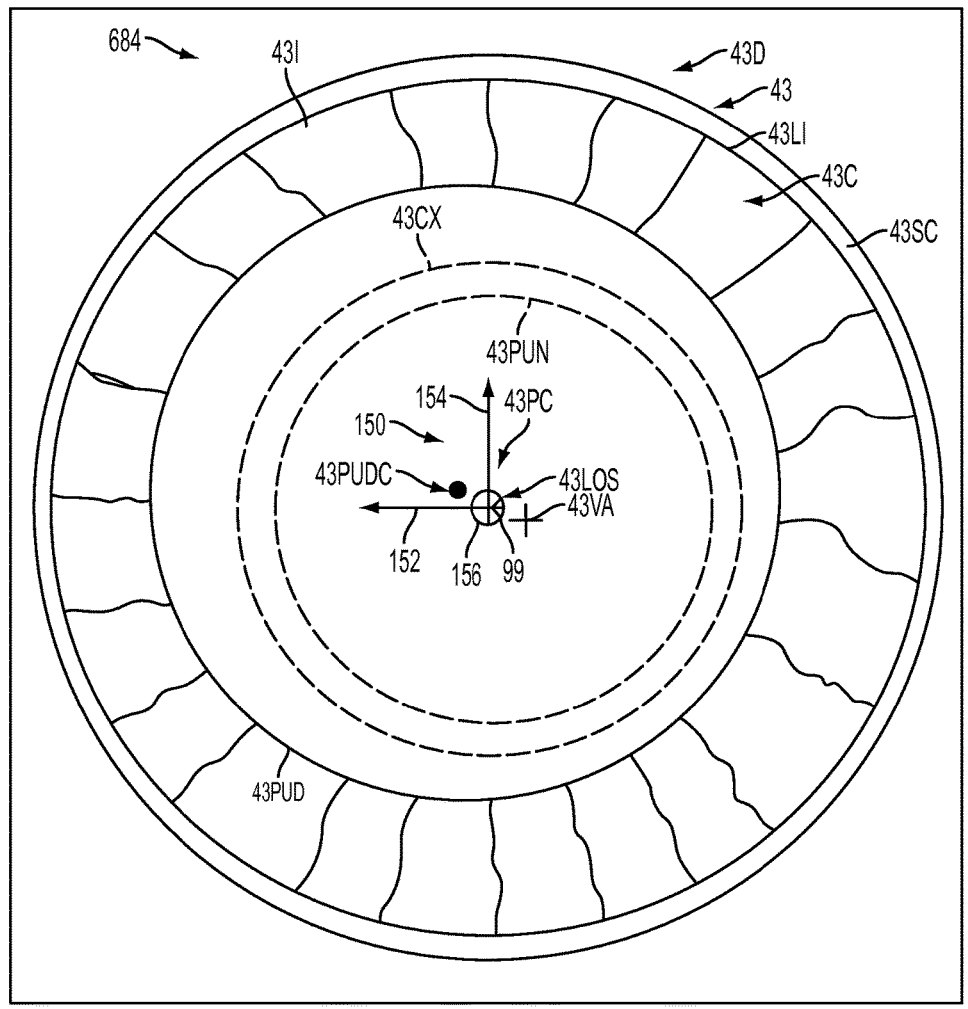

FIGS. 8A, 8B and 8C show images of a user interface display configured to show one or more optical structures of the eye to position the laser beam pulses of a tissue treatment in order to treat the eye. The images of the eye shown on the display may comprise one or more of an axial image of the eye, a sagittal image of the eye, or an anterior view of the eye, for example. Each of the images may comprise one or more markers to show one or more tissue structures of the eye, in accordance with embodiments. For example, one or more axes of the eye can be shown with one or more markers placed on the display at locations of the image of the eye to identify the location of the corresponding one or more axes of the eye. In many embodiments, one or more of the tissue structures of FIGS. 8A, 8B and 8C can shown on the display with corresponding marks placed over the image of the eye to show the location of the one or more tissue structures of the eye in relation to the eye prior to coupling the eye to the patient interface.

FIG. 8A shows an image 680 of the eye obtained with a tomography apparatus as described herein when the eye contacts the patient interface. The image 680 may comprise an image of a mydriatic eye 43M. The mydriatic eye 43M may comprise an eye treated with a mydriatic substance such as a cycloplegic agent in order to dilate the eye to visualize the lens 43L and allow access to the lens capsule with the laser beam and tomography beam. The image 680 may show a dilated pupil 43PUD having a dilated pupil center 43PUDC. The cornea coupled to the patient interface can be distorted slightly such that the vertex of the cornea has shifted to a distorted vertex 43VXD. The image 680 may show a lens of the eye treated with the mydriatic substance, such that the lens comprises a mydriatic anterior lens capsule 43LACM and a mydriatic posterior lens capsule 43LPCM, in which the mydriatic anterior lens capsule and mydriatic posterior lens capsule may be shifted posteriorly relative locations of the anterior lens capsule 43LAC and posterior lens capsule 43LPC measured prior to the patient interface contacting the eye, for example.

The eye 43 coupled to the patient interface can be displayed with a marker showing axis 99 of the optical delivery system aligned with the coordinate reference frame 150 of the eye, although axis 99 and coordinate reference frame 150 can be aligned in one or more of many ways and separate markers can be used to indicate the location of the axis and the center of the reference frame in accordance with the embodiments described herein. The markers of the eye can be shown with one or more axes of the eye rotated away from the axis 99 of the patient interface. Alternatively or in combination, one or more axes of the eye can be aligned with the axis 99 of the patient interface when the patient interface contacts the eye. Although the eye 43 is shown with a dilated pupil and a corresponding non-accommodative lens, the eye can be coupled to the patient interface without dilation of the pupil, for example.

The structures of the eye measured prior to the patient interface contacting the eye can be shown with markers on the display along with image 680 of the eye obtained when the patient interface has contacted the eye, in order to determine locations of laser incisions when the eye has contacted the patient interface. The locations of reference structures of the eye as described herein can be measured and one or more of the rotation or translation of the eye between the non-contact measurements and the contact measurements determined, for example.

The locations of one or more structures of the eye prior to contacting the interface can be shown on the display 12 with markers placed on the image 680, in order for the user to position the laser incisions on the eye contacting the patient interface with reference to locations the one or more structures prior to the eye contacting the patient interface. The pre-contact interface contact optical structure shown on the display with markers placed on image 680 may comprise one or more of, the optical axis 43AO, the pupillary axis 43PA, the line of sight 43LOS, the visual axis 43VA, the fixation axis 43FA, the natural pupil 43PUN, the anterior principal point 43AP, the posterior principal point 43PP, the entrance pupil 43ENP, the natural pupil center 43PUC, the exit pupil 43EXP, the anterior nodal point 43NA, or the posterior nodal point 43NP, for example. Alternatively or in combination, the optical structure shown on the display may comprise one or more optical structures of the eye when the interface has contacted the eye, such as one or more of the optical axis of the eye of image 680, the dilated pupillary axis, the line of sight of the dilated pupil, the visual axis of the mydriatic eye when the patient views the fixation light 119, the fixation axis, the dilated pupil 43PUD, the anterior principal point of the dilated eye of image 680, the posterior principal point of the dilated eye of the image 680, the entrance pupil of the dilated eye, the pupil center 43PUCD of the dilated pupil, the exit pupil of the mydriatic eye, the anterior nodal point of the mydriatic eye, or the posterior nodal point of the mydriatic eye, for example.

The image 680 of the eye can be shown to the user, and the user can determine one or more axis of the eye to display on the image of the eye, for example in response to user preference. The display and processor can be configured to receive user input, and the user may identify one or more axis of the eye as described herein to use as reference locations to place the capsulotomy, such as a capsulorhexis, and volume of material to be incised with the laser, for example. Alternatively or in combination, the user may identify one or more axes of the eye for corneal surgery of the eye as described herein. For example, the user may identify one axis to use as a reference to center the capsulorhexis incision, and another axis to center the corneal refractive procedure, although the same axis can be used for both.

The locations of the incisions of the eye can be determined at least in part in response to locations of the optical structures of the eye prior to the eye contacting the patient interface, for example. The location of the capsulorhexis 43CX can be determined in relation to the marker showing the natural pupil of the eye 43PUN, for example. The capsulorhexis 43CX can be centered one or more of the line of sight 43LOS, the natural entrance pupil 43ENP, the physical center of the natural pupil 43PC, the center of the exit pupil 43EXP, the natural optical axis 43AO, or the visual axis 43VA, for example. As shown in FIG. 8A, the planned capsulorhexis is shown with a marker centered in relation to the natural pupil of the eye 43PUN.

Work in relation to embodiments suggests that positioning the intraocular lens in relation to the anterior node of the eye, for example along the visual axis extending from the anterior node of the eye, can decrease deflection of the rays entering the eye when the IOL has been placed. For example, the IOL may comprise a nodal point corresponding substantially to the center of the IOL, and centering the IOL in relation to the anterior nodal point of the eye such that the IOL is aligned with the visual axis extending from the anterior nodal point can maintain the natural visual axis of the eye and inhibit deflection of the natural visual axis when the lens has been placed. In many embodiments, the capsulorhexis can be centered on the visual axis 43VA extending from the anterior node 43NA spaced apart from the posterior node 43NP, for example. The display and processor can be configured to show the visual axis 43A extending from the node on the display aligned with image 680 of the eye. Alternatively or in combination, structures can be incised in the lens capsule to inhibit movement of the lens in relation to the visual axis of the eye, for example. The structures incised in the lens may comprise incisions sized to receive protruding structures of the IOL to hold the IOL in place, for example. In many embodiments, markers indicating the locations of the structures to receive the protrusions are shown on the display.

One or more structures of the eye of image 680 can be used to identify the locations of incisions of the eye. For example, the laser can be configured to remove tissue from an incision volume 43VR of the eye defined and incision volume profile 43VRP. The incision volume 43VR and corresponding profile 43VR can be shown on the display to the user with the optical structures of the eye as described herein. The incision volume 43VR can define a volume of tissue to be incised with laser based volumetric photo fragmentation, for example. The incision volume profile 43VRP can be shown on the display positioned on image 680, for example.

The limbal relaxing incisions 43I are shown aligned with natural vertex of the cornea 43VX located along the optical axis 43AO, although one or more of many locations as described herein as described herein can be used as a reference to position the cornea incisions, for example. The limbal relaxing incisions 43LRI may comprise arcuate incisions having a center located along the optical axis of the eye 43AO, for example.

Although the eye is show coupled to an interface with the cornea away from solid structures of the interface, the embodiments as described herein can be combined with patient interfaces that flatten the cornea of the eye contact of the cornea to the interface, for example with an applanating the patient interface.

FIG. 8B shows an image 682 of anterior view of the eye as can be seen with the alignment camera and one or more tissue structures of the eye shown on the display for alignment of the eye, such as one or more optical tissue structures shown on the display for alignment of a corneal surgical procedure. The image 682 may show a dilated eye 43D as described herein, for example. The image 680 of the eye can be shown with reference axes of the coordinate reference systems as described herein. The axis 99 of the optical delivery system can be shown substantially aligned with the eye coordinate reference system 150 of the eye contacting the patient interface as described herein. The image of the eye may show the dilated pupil of the eye 43PUD. The reference axes can be shown at locations on the cornea of the eye in order to align the eye with one or more corneal surgical procedures as described herein, for example. The optical structures of the natural eye are shown at locations of the cornea and may comprise one or more optical structures determined in response to measurements obtained prior to contacting the eye with the patient interface such as one or more of the vertex of the cornea 43VX, the line of sight 43LOS, and the visual axis 43VA, for example. The locations shown on the display can be one or more of rotated or translated in response to measurements of the eye obtained when the eye contacts the patient interface. For example, the reference axis obtained prior to the patient contacting the interface may comprise dimension 654 one or more of rotated or translated in response to measurements of the eye as described herein. The treatment axis 43TRA can be one or more of rotated or translated as shown on the display for the user to plan the incisions of the eye, for example. The measurement axis can be one or more of rotated or translated about one or more axis as described herein, for example shown on the display rotated about the natural vertex of the cornea 43VX extending along the optical axis 43AO, for example. The ink dot 43ID that may have been placed on the eye can be shown on the image of the eye shown on the display, for example.

In many embodiments image 682 comprises a real time image from the alignment video camera shown on the display 12, and the axes of the eye and reference points are projected on the real time display, for example.

FIG. 8C shows an image 684 of anterior view of the eye as can be seen with the alignment camera and one or more tissue structures of the eye shown on the display for alignment of the eye, such as one or more optical tissue structures shown on the display for alignment of a corneal surgical procedure. The image 684 may comprise one or more structures of image 682, for example. The image 684 shows the dilated pupil 43PUD and the coordinate reference system 150 aligned with the eye. The dilated pupil center 43PUDC can be offset from the natural pupil 43PUN. The capsulorhexis incision 43CX can be aligned with one or more of the natural pupil 43PUN, the line of sight 43LOS, the visual axis 43VA, the axis 99 of the patient interface, the limbus 43LI, the dimension 156 of the coordinate reference system 150, or the dilated pupil center 43PUDC, for example. In many embodiments, the capsulorhexis incision is aligned with the natural pupil center 43PC of the eye.

The images of FIGS. 8A, 8B and 8C merely provide examples in accordance with some embodiments, and these figures can be combined in one or more of many ways in accordance with additional embodiments. For example, the images of FIGS. 8A and 8B can be combined to form a single image on the display, and the markers used to identify the tissue structures can be overlaid on a live image from the alignment video camera as described herein, for example. In many embodiments, the markers of the reference locations of the eye are shown on the display when the laser beam incises the tissue in order for the user to verify the placement of the laser beam incisions at the targeted locations.

Figure 9:
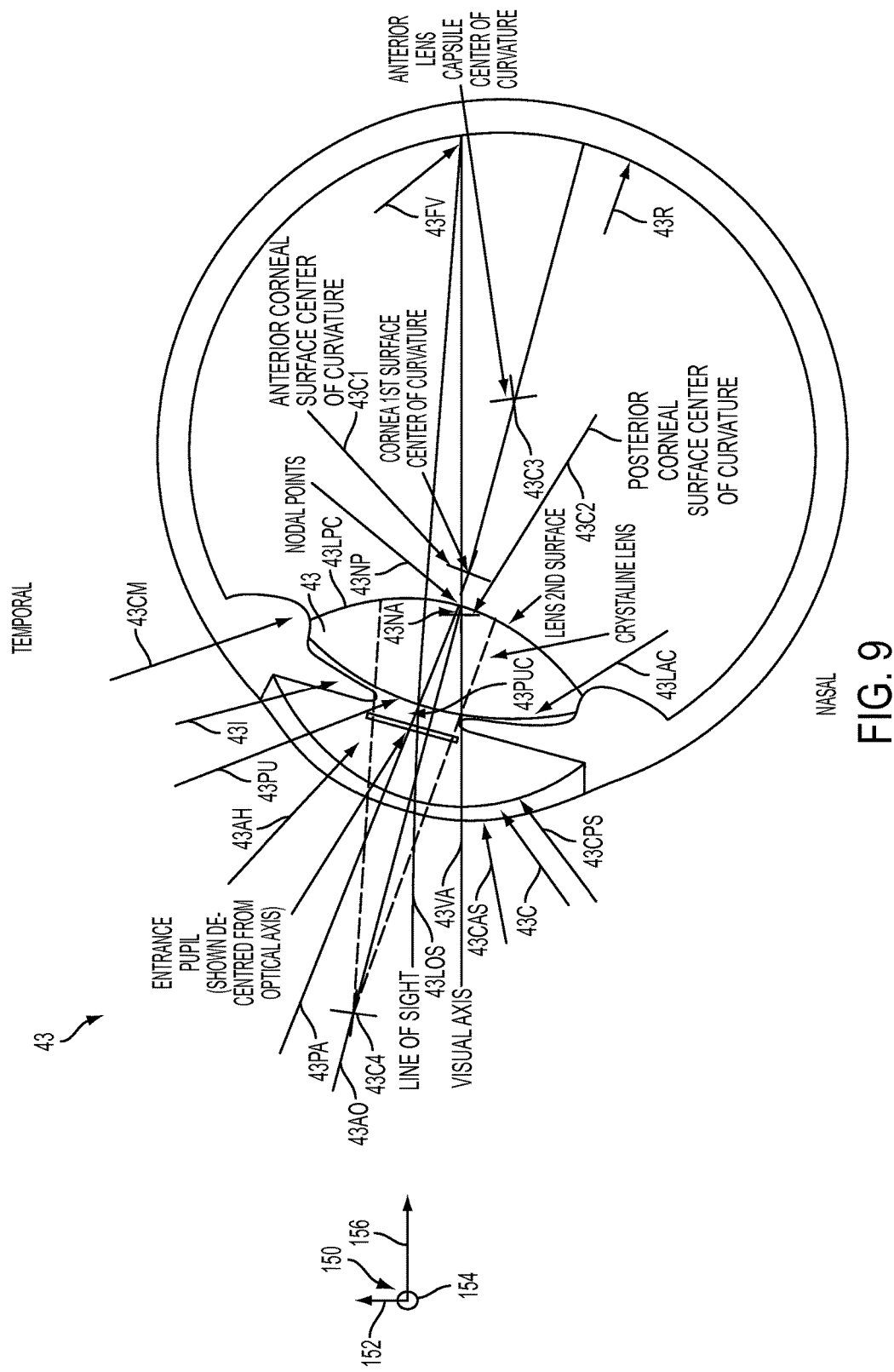
FIG. 9 shows an eye with an eccentric pupil, an offset fovea, and determination of an optical axis of the eye, in accordance with embodiments.

FIG. 9 shows a tomographic image of an eye 43 with an eccentric pupil 43PU and determination of the optical axis 43AO of the eye. The image of the eye may comprise an image of the eye obtained without the patient interface contacting the eye or an image of the eye measured with the patient interface contacting the eye. The locations and profiles of structures of the eye as described herein can be determined from the tomographic data of the eye. One or more axis of the eye can be determined in relation to the optical axis 43AO of the eye as described herein. In many embodiments, the visual axis extends substantially parallel to the measurement axis of the tomography system, and location of the visual axis determined from the anterior nodal point of the eye as described herein. The optical axis 43AO extends through the centers of curvature of the lenses of the eye. In many embodiments, the center 43PUC of the pupil 43PU of the eye is located away from the optical axis 43AO extending through the pupil. The location of the optical axis of the eye remains substantially fixed when the pupil of the eye dilates.

In the embodiments shown, the optical axis of the eye can be determined so as to provide accurate determination of the structures of the eye in order to accommodate variability among eyes and changes of tissues of an eye of a subject. The optical axis of an eye of a subject can be accurately determined when the pupil constricts and dilates and the accommodation of the lens changes, for example. For example, the embodiments shown in FIG. 9 illustrate the fovea located about 2.5× further from the optical axis than a normal eye, and the pupil is shown displaced in a temporal direction. For example, the center of the pupil can be displaced nasally or temporally away from the optical axis and the location of the optical axis remains substantially fixed when the optical axis has been determined in response to locations of the centers of curvature. In many embodiments, the pupillary axis extends through the center of the entrance pupil and the center of curvature of the cornea, and the pupillary axis can be located on the nasal side of the optical axis or the temporal side of the optical axis, for example.

The location of the optical axis can be determined in response to the locations of the centers of curvature of one or more of the anterior corneal surface 43CAS, the posterior corneal surface 43CPS, the anterior lens capsule surface 43LAC, the posterior lens capsule surface 43LPC, and combinations thereof, for example. The anterior corneal surface 43CAS has a center of curvature 43C1, and the posterior corneal surface 43CPS has a center of curvature 43C2. The anterior lens capsule 43LAC has a center of curvature 43C3, and the anterior corneal surface 43CAS has a center of curvature 43C1. Each of the centers of curvature can be determined in three dimensional space with respect to the eye coordinate reference system 150, and the locations of the centers of curvature used to determine the optical axes of the eye. The optical axis of the eye can be oriented and positioned so as to decrease the separation distance of the optical axis of the eye to the centers of curvature. For example, the optical axis can be determined with least squares fitting so as to minimize the distances from the optical axis to the centers of curvature. In many embodiments, the optical axis extends through the centers of curvature of the eye.

The centers of curvature of the optical surfaces of the eye can be determined in one or more of many ways. For example, tomography data of each surface can be fit to determine the center of curvature, and the locations of each of the centers of curvature determined. In many embodiments, one or more of the surfaces may deviate from a sphere, and the center of curvature determined from least squares approximate of the center of surface. Alternatively or in combination, the surface can be fit to an elliptical or other surface, and the centers of curvature determined from the fit surface. For example, the fit surface may comprise a three-dimensional elliptical surface, and the locations of the foci of the ellipse used to determine the center of the ellipse. The optical surface of the eye may comprise a toric surface, and the centers of curvature of portions of a surface fit to the tonic optical surface used to determine locations of the center of curvature of the eye. In many embodiments, the optical surface of the eye is fit with one or more with one or more of a Fourier transform, polynomials, a spherical harmonics, Taylor polynomials, a wavelet transform, or Zernike polynomials.

In many embodiments, the processor comprises instructions to fit profile data of the optical surface of the eye with one or more with one or more of a Fourier transform, polynomials, a spherical harmonics, Taylor polynomials, a wavelet transform, or Zernike polynomials. Each fit optical surface of the eye can be used to determine the center of curvature of the optical surface, and the centers of curvature used to determine the optical axis of the eye. The optical axis of the eye can then be used to reference one or more structures of the eye, such as axis of the eye, when the eye contacts the patient interface. In many embodiments, the non-contact optical axis of the eye is determined when the eye is free to fixate without contacting the patient interface, and the contact optical axis is determine when the eye contacts the patient interface.

Several structure optical structures of the eye can be identified in relation to the non-contact optical axis measured when the eye is free to move and view and object, and these optical structures mapped onto the eye contacting the patient interface, in response to locations and orientations of the contact optical axis and the non-contact optical axis. The orientation may comprise an orientation of the optical axis and a cyclotorsional angle of rotation about the optical axis or other axis extending in an anterior-posterior direction such as the fixation axis, the line of sight, or the pupillary axis, for example.

Figure 10:
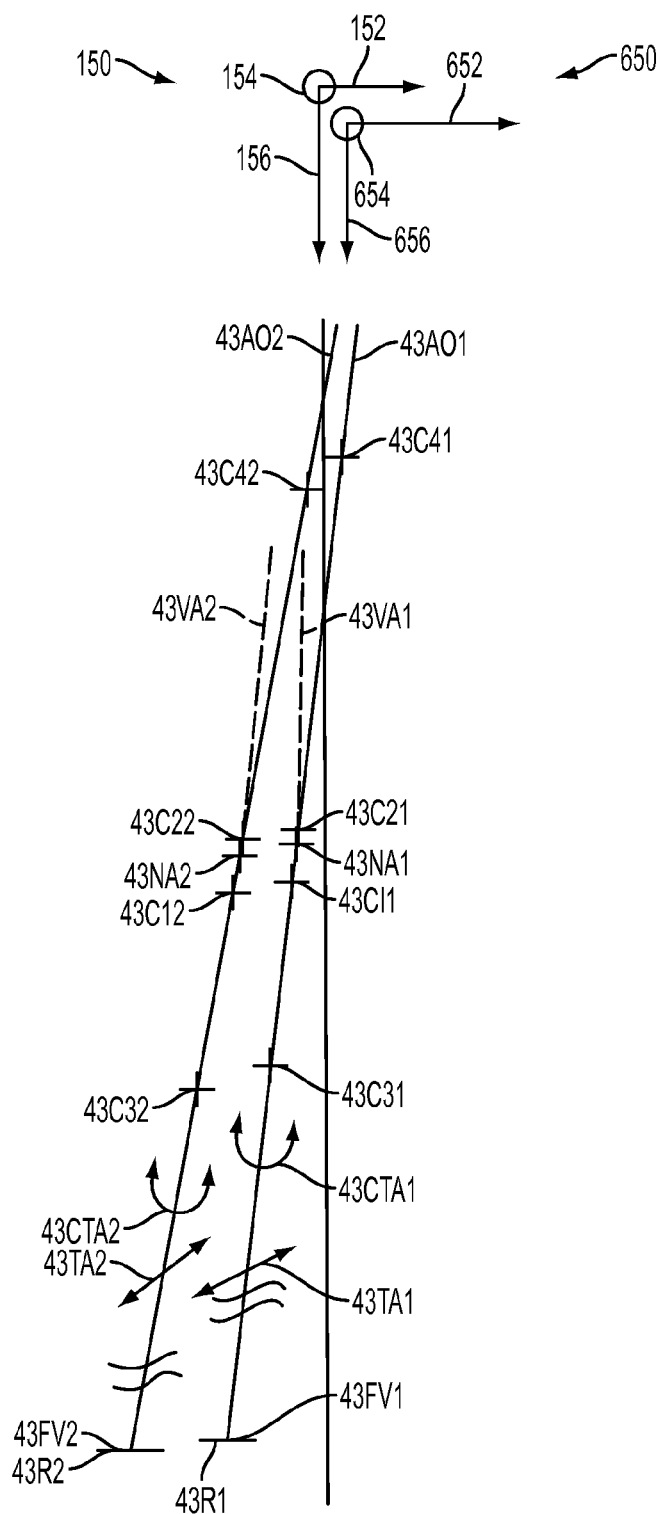
FIG. 10 shows a first optical axis of a non-contact measurement measured without contact of the eye and an second optical axis of a contact measurement measured with a patient interface contacting the eye, in which the first and second optical axes can be used to determine locations of structures of the eye when the eye contacts the patient interface, in accordance with embodiments.

FIG. 10 shows a first optical axis 43AO1 of a non-contact measurement and a second optical axis 43AO2 of a contact measurement, in which the first and second optical axes can be used to determine locations of structures of the eye when the eye contacts the patient interface. The first optical axis 43AO1 extends through a first center of curvature 43C11, a second center of curvature 43C21, a third center of curvature 43C31, and a fourth center of curvature 43C41, for example. The second optical axis 43AO2 extends through a first center of curvature 43C12, a second center of curvature 43C22, a third center of curvature 43C32, and a fourth center of curvature 43C42, for example.

The first optical axis 43AO1 extends through a first anterior nodal point 43NA1 of the eye and a first posterior nodal point 43NP1 of the eye. A first visual axis 43VA1 extends from the first anterior nodal point 43NA1 to a fixation light such as fixation light 119 as described herein.

The path of the visual axis can be determined from the location of the anterior nodal point of the eye and the location of the fixation light, which can be placed such that the visual axis 43A1 extends substantially parallel to measurement axis 699 the longitudinal dimension 656 of non-contact coordinate reference system 650, for example. The first optical axis can be used to define a first cyclo torsional angle 43CTA1 of the eye and a first treatment axis of the eye 43TA1. The first optical axis extends to a first location of the retina 43R1 that may be located on a first location of the fovea 43FV1. The first distances from the retina to the centers of curvature can be used to define the locations of structures of the eye, and to identify distortion of the eye. The non-contact coordinate reference system 650 may comprise the coordinate reference system of a separate diagnostic imaging device as described herein, or the coordinate reference system 150 of the laser system 2 prior to contacting the eye with the patient interface, for example. In many embodiments, the first locations of the first centers of curvature are determined with reference to coordinate reference system 650.

One or more of the optical structures of the eye can be difficult to determine when the patient interface contacts the eye, as the eye may not move freely, and the fixation light, if present can be blurry in at least some embodiments. For example the line of sight, visual axis, and treatment axis can be difficult to identify when the eye contacts the patient interface. The locations of one or more of the line of sight, visual axis, or the treatment axis can be determined in accordance with the embodiments disclosed herein.

The axes of the eye can be determined in one or more of many ways when the patient interface contacts the eye in accordance with embodiments disclosed herein. For example, the second optical axis 43AO2 extends through a second anterior nodal point 43NA2 of the eye and a second posterior nodal point 43NP2 of the eye when the eye contacts the patient interface. A second visual axis 43VA2 extends from the second anterior nodal point 43NA2. The path of the second visual axis 43VA2 can be determined from the location of the second anterior nodal point 43NA2 and the orientation and angles of the first visual axis 43VA1 with respect to the first anterior nodal point 43NA1, such that the second visual axis 43VA2 extends from the second anterior nodal point 43NA2 and the second optical axis 43AO2 with angles similar to the first visual axis 43VA1 extending from the first anterior nodal point 43NA1 and first optical axis 43AO1. The second optical axis can be used to define a second cyclo torsional angle 43CTA2 of the eye and a second treatment axis of the eye 43TA2. The second treatment axis 34CTA2 can be determined in response to cyclotorsion of the eye about the optical axis 43AO when the eye 43 rotates from first cyclotorsional angle 43CTA1 to second cyclotorsional angle 43CTA2. In many embodiments, difference in angle between the second cyclotorsional angle 43CTA2 and first cyclotorsional angle 43CTA1 is determined, the second treatment axis 43TA2 is determined in response to the difference in the cyclotorsional angle of the eye. Although reference is made to the cyclotorsional angles, in many embodiments, correction for changes in head tilt with respect to the measurement axis can be provided with measurement of the torsional angles of the eye around the optical axis as described herein. For example, the head of the patient can tilt from the first measurement to the second measurement, and the measurement of the cyclotorsional angle of the eye can correct for the head tilt.

The second optical axis extends to a second location of the retina 43R2 that may be located on a second location of the fovea 43FV2. The second distances from the retina to the centers of curvature can be used to define the locations of structures of the eye, and to identify distortion of the eye, for example when these distances vary between the first non-contact measurements and the second contact measurements. The contact coordinate reference system 150 may comprise the coordinate reference system 150 of the laser system 2 when the patient interface contacts the eye, for example.

In many embodiments, the first locations of the first centers of curvature are determined with reference to coordinate reference system 650 for non-contact measurements, and the locations of the second centers of curvature are determined with coordinate reference system 150 when the eye contacts the patient interface. For example, the coordinate reference system 150 of the laser system can be used for first non-contact measurements of the eye and comprises the non-contact coordinate reference system 650, and the second contact measurements of the eye may comprise the coordinate reference system 150, in which the locations of the structures of the eye can be mapped from the first locations of coordinate reference system 650 to the second locations of coordinate reference system 150, in order to determine locations of optical structures of the eye when the patient interface contacts the eye, such as the visual axis and line of sight as described herein.

In many embodiments, each center of curvature may comprise a narrow cross-section of a bundle of light rays normal to the optical surface of the eye that do not coincide at a single point, and the center of curvature may comprise a volumetric region of space defined with the bundle of rays similar to a circle of least confusion. Although the first centers of curvature may not lie exactly on a line, the first optical axis as described herein can be considered to extend through the first centers of curvatures when the first optical axis is located and oriented to decrease separation of the first optical axis to each of the first centers of curvature. Although the second centers of curvature may not lie exactly on a line, the second optical axis as described herein can be considered to extend through the second centers of curvatures when the first optical axis is located and oriented to decrease separation of the second optical axis to each of the second centers of curvature.

In many embodiments, the location and orientations of the first optical axis 43VA1, the second optical axis 43VA2, the first cyclotorsional angle 43CTA1, and the second cyclotorsional angle 43CTA2, can be used to determine parameters of a coordinate mapping function in order to determine locations of first tissue structures of the eye on an image of the eye contacting the patient interface shown on the display as described herein. For example, the locations of one or more of the first visual axis, the first pupil, or the first line of sight can be shown on the image of the eye contacting the patient interface, which may comprise a real time image of the eye, for example.

The structures of the eye can be mapped from the first non-contact coordinate reference system 650 to the second coordinate reference system 150 in one or more of many ways. For example, the location and orientation of the second optical axis can be determined and used as a reference axis to map structures of the eye such as one or more of the natural pupil of the eye, the visual axis of the eye, the line of sight of the eye, or the treatment axis of the eye, and combinations thereof, for example. In many embodiments, the cyclotorsional angle of the eye around the optical axis is determined in each of the first non-contact coordinate reference system 650 and the second coordinate reference system 150, and the structures of the eye mapped from the first non-contact coordinate reference system to the second coordinate reference system in response to the angles, for example in response to a change in the first cyclo torsional angle and the second cyclo torsional angle.

In many embodiments, the coordinate reference locations of the structures of the eye from the first non-contact measurements of coordinate reference system 650 are mapped to coordinate reference locations of the second measurement coordinate reference system 150. In many embodiments a mapping function is determined in order to map the structures of the eye from the first non-contact measurements to the second contact measurements for display on images obtained when the interface contacts the eye as described herein. In many embodiments, the mapping function takes the form of:

(X2, Y2, Z2)=M(X1, Y1, Z1)

Where X1, Y1, Z1, are the X, Y and Z coordinates along dimensions 652, 654 and 656, respectively, of first non-contact reference coordinate system 650, and X2, Y2, Z2, are the X, Y and Z coordinates along dimensions 152, 154 and 156, respectively, of the second reference coordinate system 150, for example. A person of ordinary skill in the art can determine the mapping function M(X1, Y1, Z1) with the first locations first structures of the eye and second locations of second structures of the eye, in accordance with the teachings disclosed herein. In many embodiments, the mapping function is determined with locations of the first centers of curvature and the first cyclotorsional angle and the second centers of curvature and the second cyclotorsional angle, for example.

In embodiments where the first measurement comprises a non-contact measurement of an eye at a separate diagnostic device and the second measurement comprises a non-contact measurement from the laser system, the coordinate references can be similarly transformed to determine locations of the structures of the eye as described herein. In many embodiments, the second non-contact measurement of the eye can be used to align the treatment axis 43TRA of the eye with the laser system, for example in order to determine the second treatment axis 43TRA2 in response to an astigmatic axis of the eye as described herein.

While the topography measurement system can be coupled to the laser system in many ways, in many embodiments the topography measurement system comprises a coupling structure to couple a topography measurement structure to the patient interface.

FIGS. 11A-11E show a topography measurement structure configured to couple to a patient interface 52 as described herein to measure the eye prior to the eye contacting the patient interface. The topography measurement structure may comprise one or more of a ring or other structure for a keratometry reading of the eye, a Placido disc topography of the eye, a reflection of a plurality of points from the cornea topography of the eye, a grid reflected from the cornea of the eye topography. In many embodiments, the measurement structure comprises a Placido disc structure configured to couple to a component of the patient interface, for example. The topography measurement structure can be illuminated, for example, so as to form a virtual image of the measurement structure when reflected from the cornea. One illumination strategy could make use of the internal existing illuminator of the system itself. Alternatively or in combination, the topography structure may comprise a ring illuminator either mounted to the patient interface or to the structure of the laser system.

In many embodiments, topography measurement structure is back illuminated with light from the laser system to illuminate the eye with the topography measurement structure. Alternatively or in combination the topography measurement structure may comprise a plurality of light sources such as light emitting diodes to illuminate the eye with the topography measurement structure.

Figure 11A:
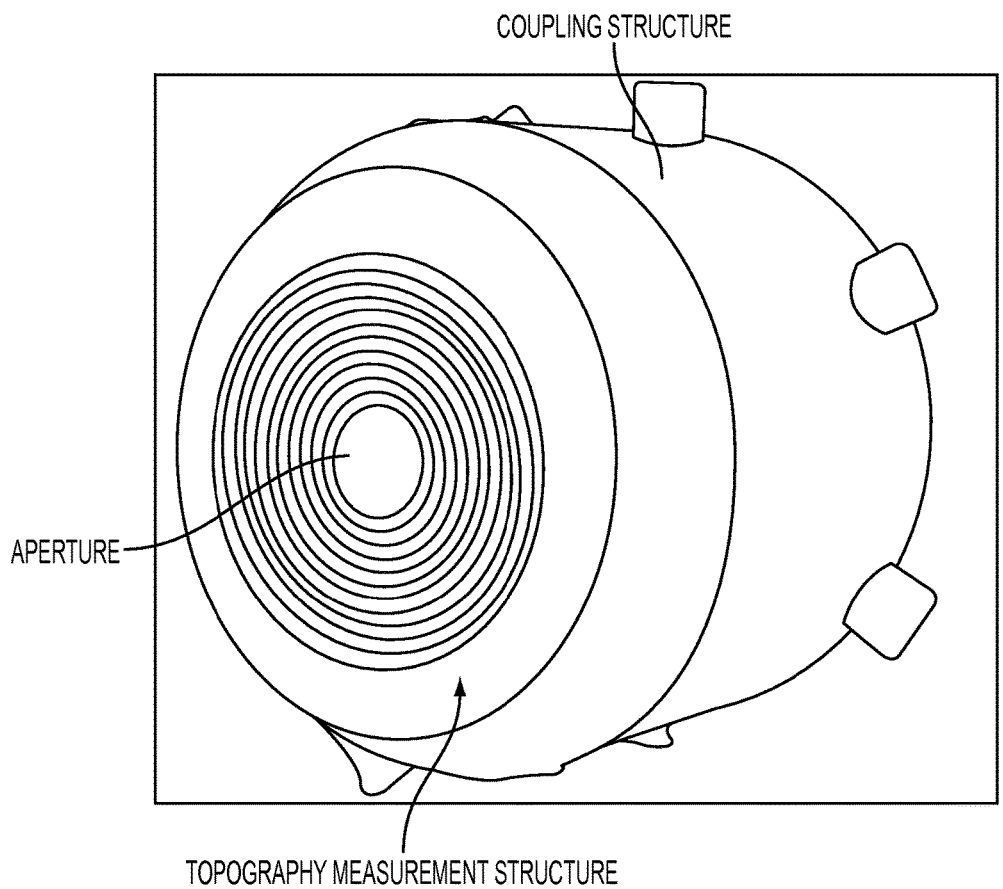
FIG. 11A shows a topography measurement structure configured to couple to a patient interface to measure the eye prior to the eye contacting the patient interface, in accordance with embodiments.
Figure 11B:
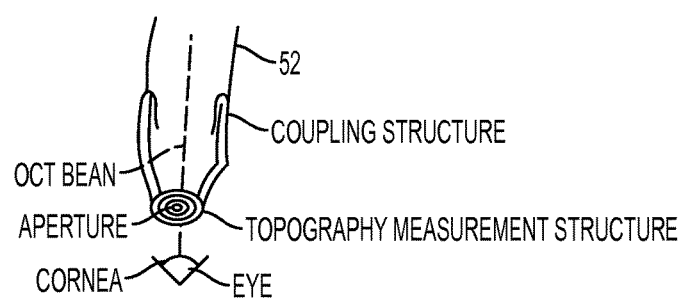
FIG. 11B shows components of the patient interface and the topography measurement structure configured to couple to the patient interface, in accordance with embodiments.
Figure 11C:
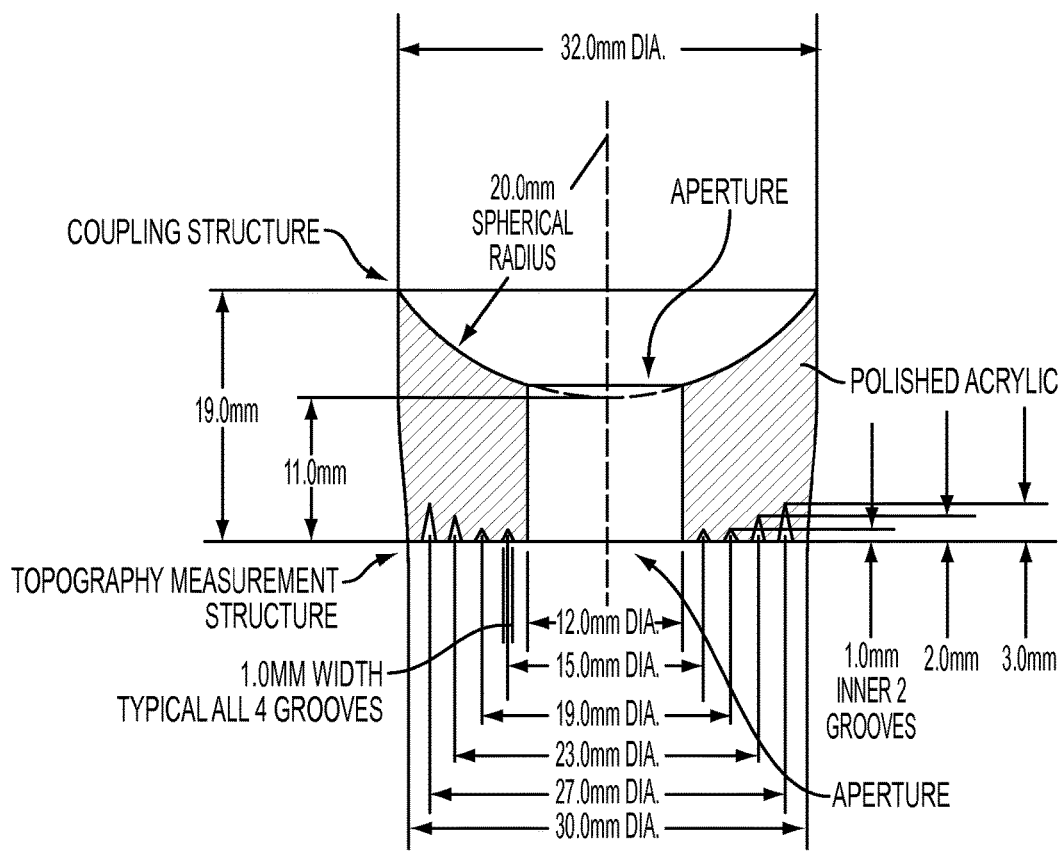
FIG. 11C shows a sectional view of the topography measurement structure.
Figure 11D:
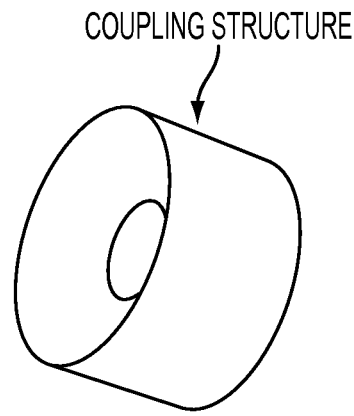
FIG. 11D shows a perspective view of the interface end of the topography measurement structure.
Figure 11E:
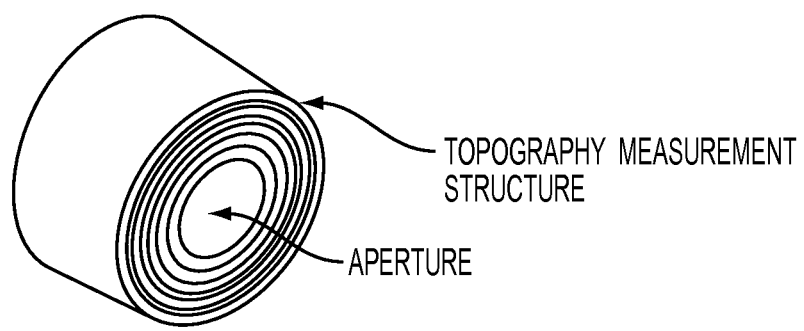
FIG. 11E shows a perspective view of the working end of the topography measurement structure.

FIG. 11B shows the topography measurement structure removable coupled to the patient interface to position the topography measurement structure in relation to the eye when the patient has been placed on the support of the laser eye surgery system as described herein. The OCT measurement beam can be used to position the eye. This use of the OCT measurement beam may be particularly important to achieve absolute curvature readings of the Placido system as the diameter of the reflected Placido rings may depend not only on the curvature of the cornea but also from the distance of the ring illuminator and the cornea. OCT can help to minimize these variations. Additionally, this measurement information can also be used to actively track position the patient's chair and move the eye into the correct or desired position. Additionally, the OCT system and optionally also the camera can be used to locate the actual position of the Placido ring in relation to the system to enable high precision measurements. Alternatively or in combination, the focus of the video camera as describe herein can be used to position the eye for measurement. When the topography of the patient has been measured and the axis determined, for example, the topography measurement system can be decoupled from the patient interface structure and the patient interface coupled to the eye as described herein.

The Placido disk illuminator can be constructed in many different ways. Having a clear aperture in the center of the ring structure to allow the video system to be used as is may be particularly important. Other embodiments may comprise a combination of different engineered diffusers and masks which can be optimized on the diffusing angle used to the detection of the rings from the cornea. Or, if polarized light is used, a combination of quarter wave plate or depolarizer and diffuser with ring apertures can be used. For full utilization, the light illuminated on the blocked rings can make the blocked rings act as reflecting wedges so the light is fully utilized. In such cases, an angle which enables total reflection may be helpful. Utilizing a combination of a strong negative lens and the Placido disk illuminator can also increase the light intensity of the outer rings for better contrast.

In many embodiments, the topography measurement structure comprises an external illumination structure such as a ring illuminator illuminates the eye to form a ring shaped virtual image of the illumination structure, and the astigmatic axis of the eye determined based on measurements of the virtual image of the eye as described herein. The external illuminator can be configured to couple to the patient interface for measurement of the eye and removed when the eye has been docked to the patient interface. Alternatively, the external illuminator may comprise a substantially fixed structure that remains fixed to the laser system throughout a plurality of procedures.

The corneal topography data and thickness data can be combined in one or more of many ways. For example, the corneal topography data can be used to determine the shape profile of the anterior corneal surface, and the corneal thickness profile data can be fit to the anterior corneal surface profile in order to determine the profile of the posterior surface, for example. In many embodiments, the anterior corneal surface profile is measured and determined without the patient interface contacting the eye, and the corneal thickness profile is measured and determined when the patient interface contacts the eye. The corneal surface profile data measured without contacting the eye can be combined with the corneal thickness profile data measured with the patient interface contacting the eye, and the location of refractive incisions determined in response to both profiles, for example.

FIG. 11B shows components of the patient interface and the topography measurement structure configured to couple to the patient interface.

Figure 12:
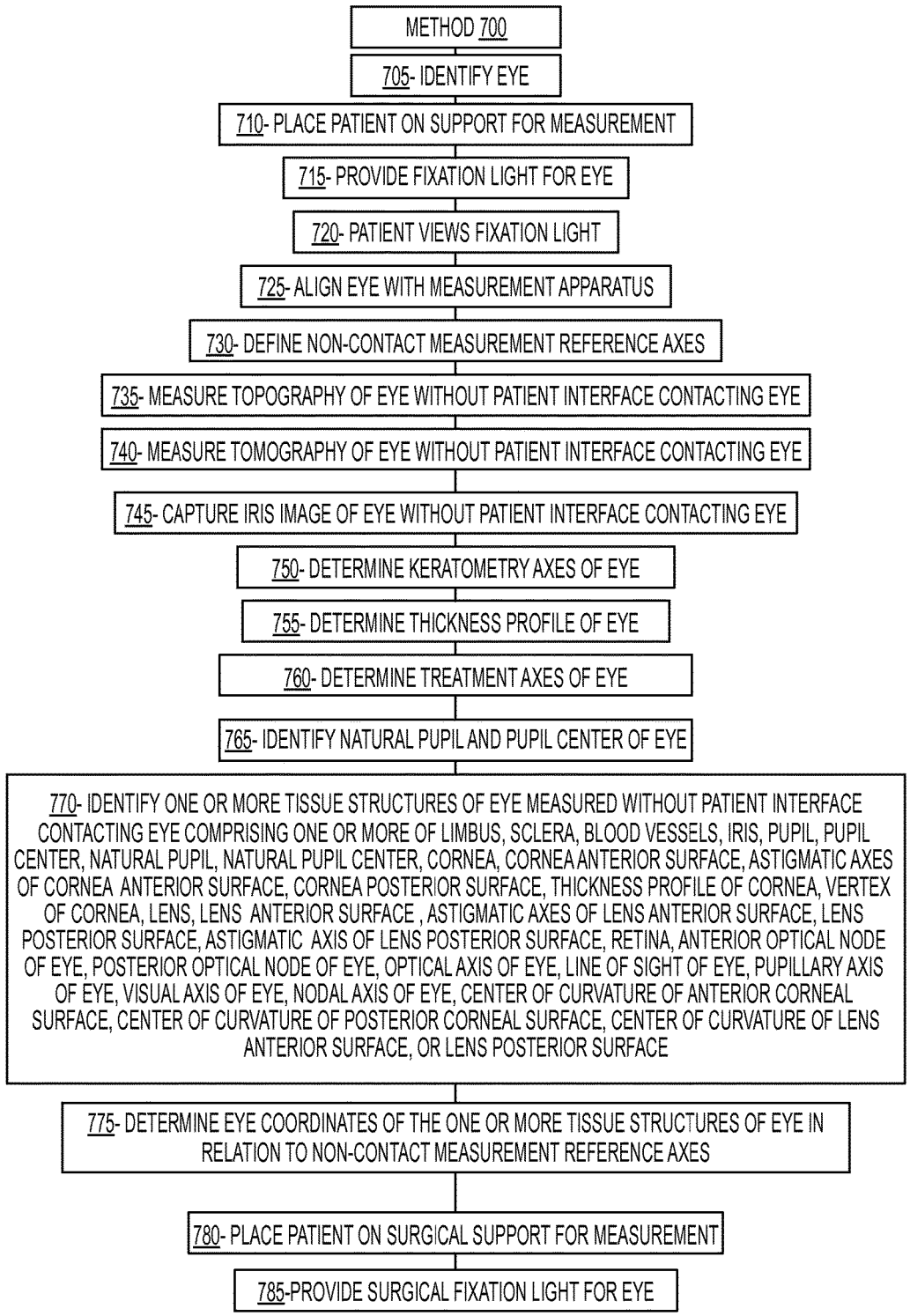
FIG. 12 shows a method of treating an eye with a laser beam, in accordance with embodiments.
Figure 12:
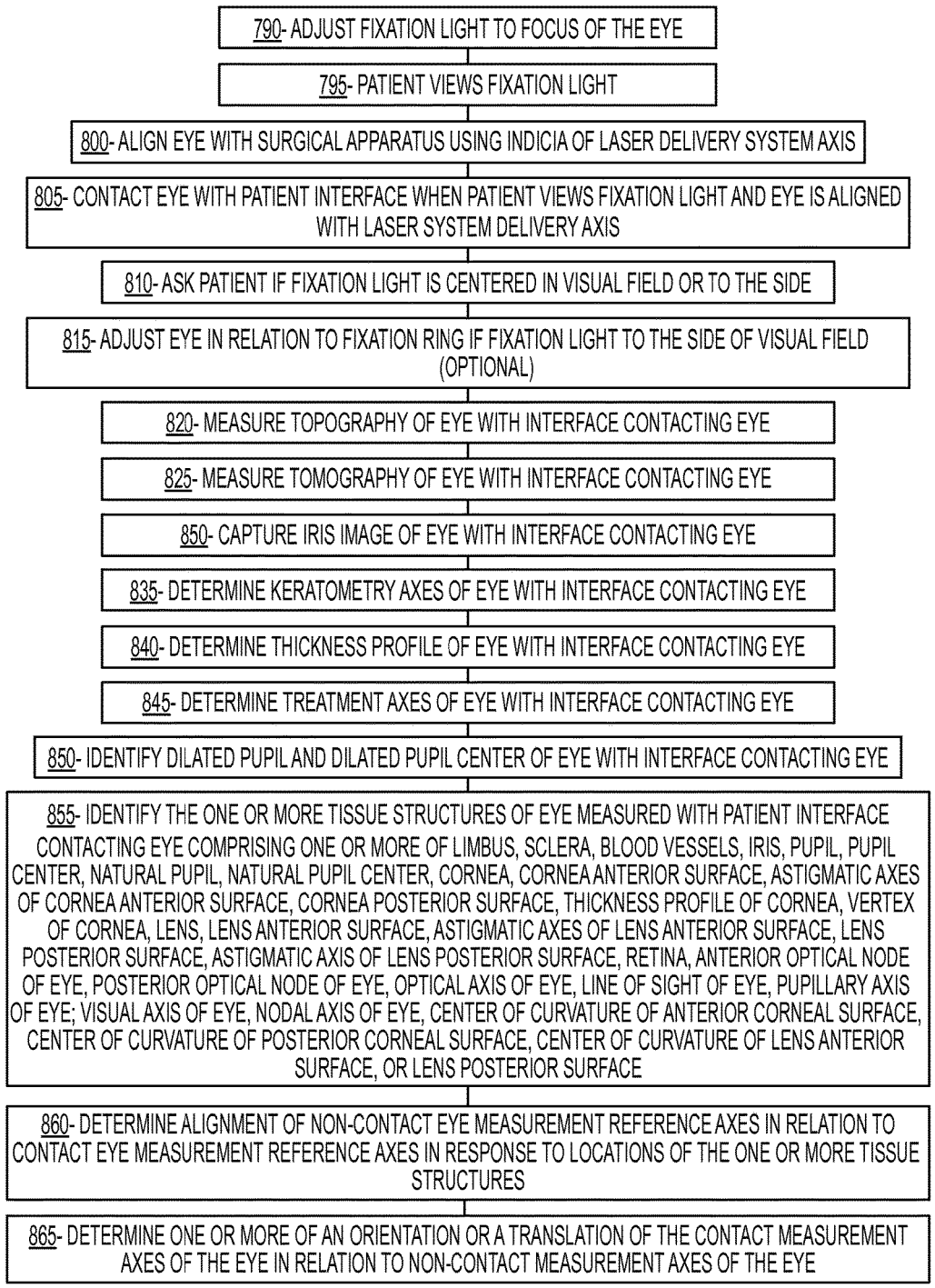
Figure 12:
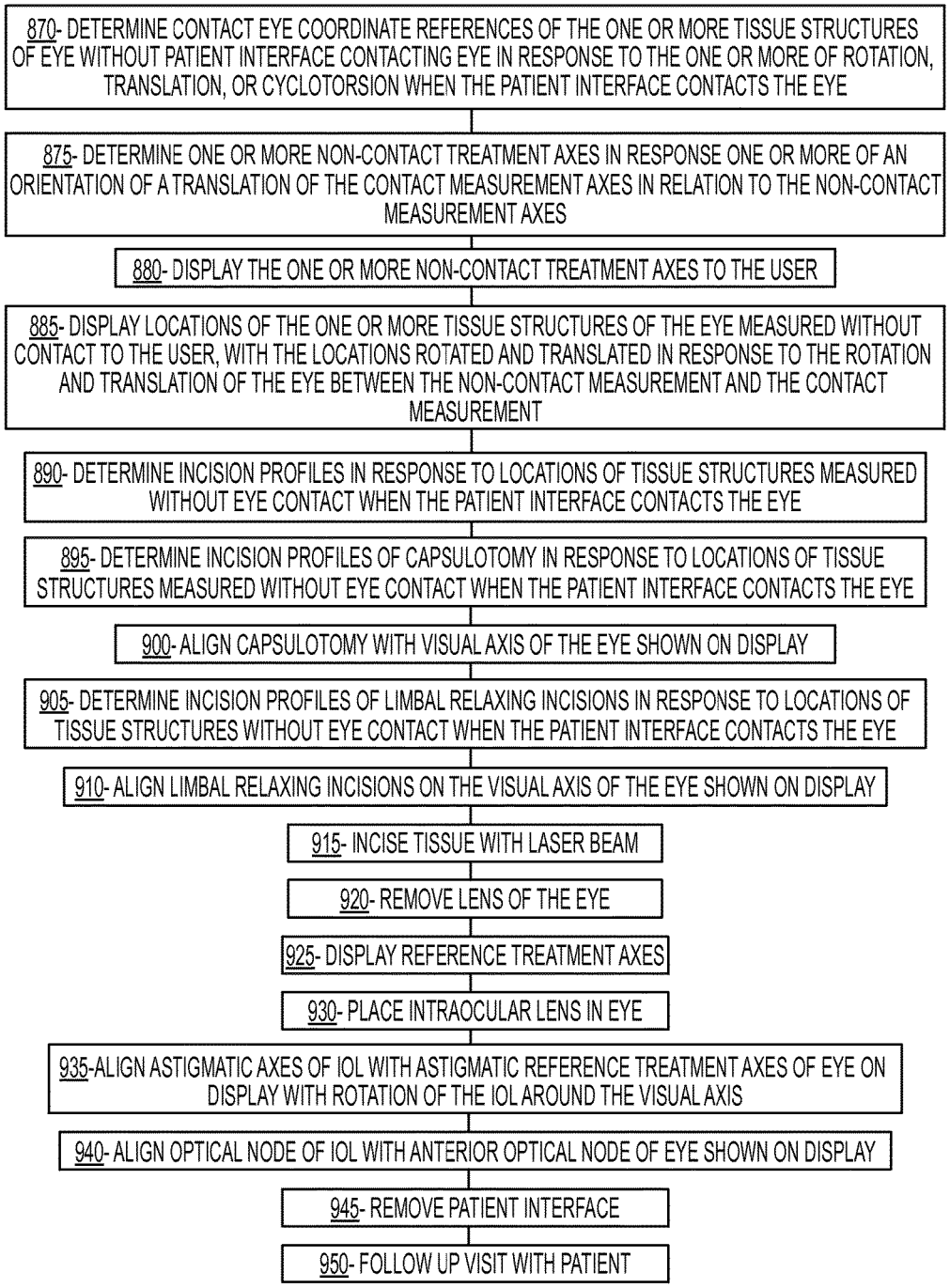

FIG. 12 shows a method 700 of treating an eye with a laser beam.

Method 700, the steps of the method 700 comprise one or more of the following steps.

At a step 705, the eye is identified.

At a step 710, the patient is placed on the support for measurement.

At a step 715, provide fixation light for eye.

At a step 720, patient views fixation light.

At a step 725, align eye with measurement apparatus.

At a step 730, define non-contact measurement reference axes.

At a step 735, measure topography of eye without patient interface contacting eye.

At a step 740, measure tomography of eye without patient interface contacting eye.

At a step 745, capture Iris image of eye without patient interface contacting eye.

At a step 750, determine keratometry axes of eye.

At a step 755, determine thickness profile of eye.

At a step 760, determine treatment axes of eye.

At a step 765, identify natural pupil and pupil center of eye.

At a step 770, identify one or more tissue structures of eye measured without patient interface contacting eye comprising one or more of limbus, sclera, blood vessels, iris, pupil, pupil center, natural pupil, natural pupil center, cornea, cornea anterior surface, astigmatic axes of cornea anterior surface, cornea posterior surface, thickness profile of cornea, vertex of cornea, lens, lens anterior surface, astigmatic axes of lens anterior surface, lens posterior surface, astigmatic axis of lens posterior surface, retina, anterior optical node of eye, posterior optical node of eye, optical axis of eye, line of sight of eye, pupillary axis of eye, visual axis of eye, nodal axis of eye, center of curvature of anterior corneal surface, center of curvature of posterior corneal surface, center of curvature of lens anterior surface, or lens posterior surface.

At a step 775, determine eye coordinates of the one or more tissue structures of eye in relation to non-contact measurement reference axes.

At a step 780, place patient on surgical support for measurement.

At a step 785, provide surgical fixation light for eye.

At a step 790, adjust fixation light to focus of the eye.

At a step 795, patient views fixation light.

At a step 800, align eye with surgical apparatus using indicia of laser delivery system axis.

At a step 805, contact eye with patient interface when patient views fixation light and eye is aligned with laser system delivery axis.

At a step 810, ask patient if fixation light is centered in visual field or to the side.

At a step 815, adjust eye in relation to fixation ring if fixation light to the side of visual field.

At a step 820, measure topography of eye with interface contacting eye.

At a step 825, measure tomography of eye with interface contacting eye.

At a step 830, capture Iris image of eye with interface contacting eye.

At a step 835, determine keratometry axes of eye with interface contacting eye.

At a step 840, determine thickness profile of eye with interface contacting eye.

At a step 845, determine treatment axes of eye with interface contacting eye.

At a step 850, identify dilated pupil and dilated pupil center of eye with interface contacting eye.

At a step 855, identify the one or more tissue structures of eye measured with patient interface contacting eye comprising one or more of limbus, sclera, blood vessels, iris, pupil, pupil center, natural pupil, natural pupil center, cornea, cornea anterior surface, astigmatic axes of cornea anterior surface, cornea posterior surface, thickness profile of cornea, vertex of cornea, lens, lens anterior surface, astigmatic axes of lens anterior surface, lens posterior surface, astigmatic axis of lens posterior surface, retina, anterior optical node of eye, posterior optical node of eye, optical axis of eye, line of sight of eye, pupillary axis of eye, visual axis of eye, nodal axis of eye, center of curvature of anterior corneal surface, center of curvature of posterior corneal surface, center of curvature of lens anterior surface, or lens posterior surface.

At a step 860, determine alignment of non-contact eye measurement reference axes in relation to contact eye measurement reference axes in response to locations of the one or more tissue structures.

At a step 865, determine one or more of an orientation or a translation of the contact measurement axes of the eye in relation to non-contact measurement axes of the eye.

At a step 870, determine contact eye coordinate references of the one or more tissue structures of eye without patient interface contacting eye in response to the one or more of rotation, translation, or cyclotorsion when the patient interface contacts the eye.

At a step 875, determine one or more non-contact treatment axes in response one or more of an orientation of a translation of the contact measurement axes in relation to the non-contact measurement axes.

At a step 880, display the one or more non-contact treatment axes to the user.

At a step 885, display locations of the one or more tissue structures of the eye measured without contact to the user, with the locations rotated and translated in response to the rotation and translation of the eye between the non-contact measurement and the contact measurement.

At a step 890, determine incision profiles in response to locations of tissue structures measured without eye contact when the patient interface contacts the eye.

At a step 895, determine incision profiles of capsulotomy in response to locations of tissue structures measured without eye contact when the patient interface contacts the eye.

At a step 900, align capsulotomy with visual axis of the eye shown on display.

At a step 905, determine incision profiles of limbal relaxing incisions in response to locations of tissue structures without eye contact when the patient interface contacts the eye.

At a step 910, align limbal relaxing incisions on the visual axis of the eye shown on display.

At a step 915, incise tissue with laser beam.

At a step 920, remove lens of the eye.

At a step 925, display reference treatment axes.

At a step 930, place intraocular lens in eye.

At a step 935, align astigmatic axes of IOL with astigmatic reference treatment axes of eye on display with rotation of the IOL around the visual axis.

At a step 940, align optical node of IOL with anterior optical node of eye shown on display.

At a step 945, remove patient interface.

At a step 950, follow up visit with patient.

FIG. 12 shows a method 700 in accordance with embodiments. Several modifications and variations can be provide, such as the steps can be performed in any order, one or more of the steps may comprise substeps, one or more steps can be removed, one or more steps can be repeated, and a person of ordinary skill in the will recognize many variations in accordance with method disclosed herein. Further, the circuitry of system 2 as described herein, for example the processor of system 2, can be configured with instructions to perform one or more of the steps of method 700, and the tangible medium of the processor may embody instructions to perform one or more of the steps of method 700. In many embodiments, the tangible medium comprises instructions of a computer readable memory having instructions of a computer program to perform one or more of the steps of method 700. Alternatively or in combination, the logic array, such as the field programmable gate array as described herein can be programmed to perform one or more of the steps of method 700. In many embodiments, the processor comprises a plurality of processors and may comprise a plurality of distributed processors.

Figure 13:
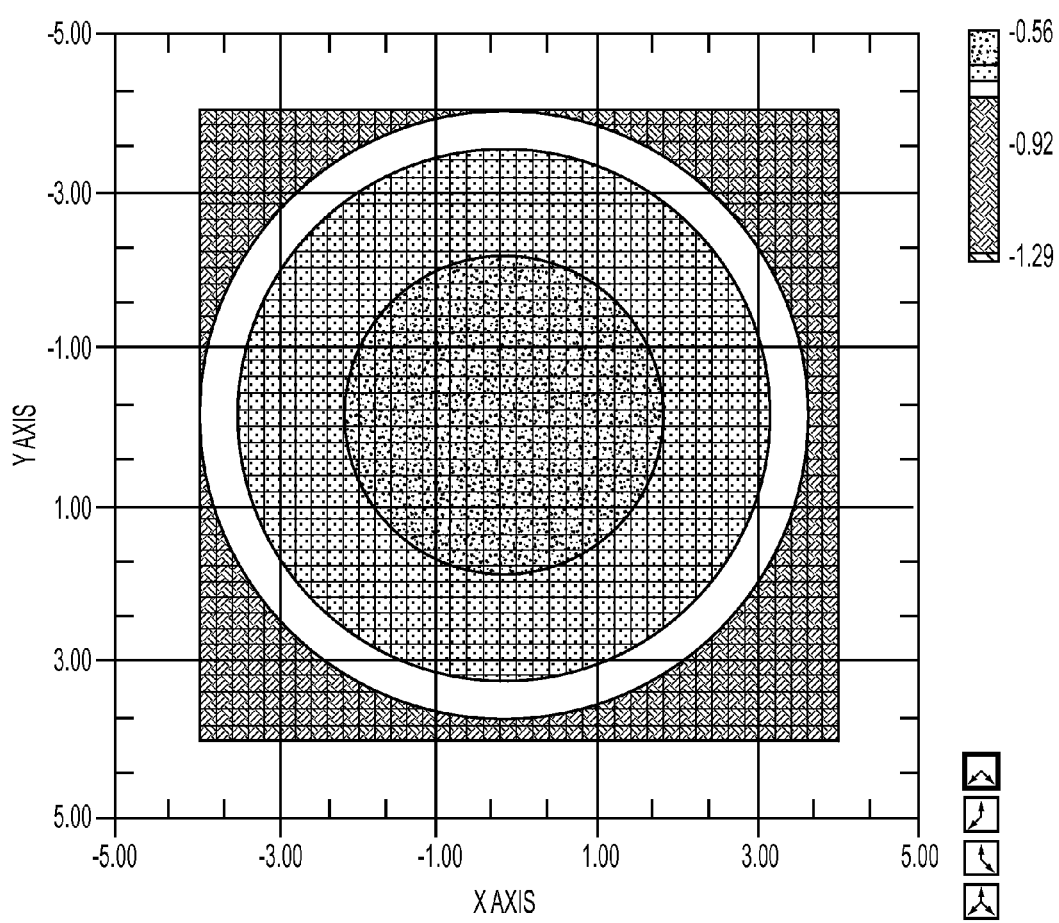
FIG. 13 shows a corneal thickness profile map measured from a person with an OCT system, in accordance with embodiments.

FIG. 13 shows a corneal thickness profile map measured from a human subject with an OCT system as described herein. The corneal thickness profile map can be fit with a spherical surface and the residual plotted against a sphere as shown. The data shows a deviation of over one micron across the surface. Work in relation to embodiments suggests that an eye treated to correct refractive error will have greater amounts of error. The corneal thickness map can be used to determine an axis of the eye as described herein, for example an astigmatic axis of the eye when the patient interface couples to the eye.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A method comprising:
    using one or more of an imaging device and a profile measurement device, generating one or more of a first image and a first shape profile of an eye of a patient when no patient interface is either in contact with the eye or located on an optical path between the eye and the one or more of the imaging device and the profile measurement device;
    thereafter, placing a patient interface in contact with the eye, wherein the patient interface includes a suction ring which is in contact with the eye and an optically transmissive element which is located on the optical path between the eye and the one or more of the imaging device and the profile measurement device when the patient interface is placed in contact with the eye; and
    generating one or more of a second image and a second shape profile of the eye with the patient interface placed in contact with the eye;
    comparing the first image with the second image or comparing the first shape profile with the second shape profile to determine one or more of a position and an orientation of the eye when the patient interface is in contact with the eye.

2. The method of claim 1,
    wherein the step of generating one or more of a first image and a first shape profile of the eye includes measuring the first shape profile of a cornea of the eye when the patient is supported with a patient support of a laser surgery system; and
    wherein the second image is generated when the patient is supported with the patient support of the laser surgery system.

3. The method of claim 2, further comprising determining an axis of treatment of an astigmatism of the eye based on the shape profile, the shape profile comprising one or more of a keratometry reading of the eye, a corneal topography of the eye, an optical coherence tomography of the eye, a Placid disc topography of the eye, a reflection of a plurality of points from the cornea topography of the eye, a grid reflected from the cornea of the eye topography, a Hartmann-Shack topography of the eye, a Scheimpflug image topography of the eye, a confocal tomography of the eye, or a low coherence reflectometry of the eye.

4. The method of claim 2, further comprising determining an axis of treatment of a plurality of arcuate incisions based on the shape profile, the plurality of arcuate incisions extending along an arc transverse to the axis of treatment.

5. The method of claim 4, further comprising displaying locations of the plurality of arcuate incisions on the second image of the eye after mapping the locations of the plurality of arcuate incisions from first locations of the first image to second locations of the second image, the second locations being different from the first locations due to distortion of the eye with the patient interface placed in contact with the eye, and wherein the first image and the second image are generated with a camera of the laser surgery system.

6. The method of claim 5, further comprising applying a plurality of pulsed laser beams to locations of the eye to treat the eye by making the plurality of arcuate incisions.

7. The method of claim 4, further comprising applying a plurality of pulsed laser beams to locations of the eye to treat the eye by making the plurality of arcuate incisions.

8. The method of claim 1, further comprising:
    modifying the first image to provide a distorted first image based on a correlation of the first image with the second image; and
    providing the distorted first image on a display visible to a user.

9. The method of claim 8, wherein the modifying step includes the user adjusting one or more of a location or an angle of the first distorted image on the display and wherein locations of a plurality of laser beam pulses are adjusted in response to the location or the angle of the first distorted image on the display.

10. The method of claim 9, further comprising applying the plurality of pulsed laser beams to locations of the eye to treat the eye.

11. The method of claim 8, wherein the modifying step includes overlaying the distorted first image on the second image on the display to determine a position and an angle of the eye for treatment, and a processor determining the position and the angle of the distorted first image on the display in response to user input to adjust locations of a plurality of laser beam pulses.

12. The method of claim 11, further comprising applying the plurality of pulsed laser beams to locations of the eye to treat the eye.

13. The method of claim 1, further comprising:
modifying the second image to provide a corrected second image based on a correlation of the second image with the first image.

14. The method of claim 1, wherein the patient interface further includes one or more of a liquid or a viscoelastic material disposed between a cornea of the eye and the optically transmissive element and wherein the one or more of the liquid or the viscoelastic is in contact with the cornea.

15. The method of claim 1, wherein the first image comprises a first plurality of image structures corresponding to a plurality of tissue structures of the eye and located at a first plurality of locations of the first image, and the second image comprises a second plurality of image structures corresponding to the plurality of tissue structures of the eye and located at a second plurality of locations of the second image, wherein the first plurality of locations are different from the second plurality of locations due to distortion of the patient interface.

16. The method of claim 1, wherein the first image and the second image correspond to a coordinate reference of a laser treatment system, the method further comprising mapping a plurality of locations of the first image from first locations of the coordinate reference of the laser system to second locations of the coordinate reference of the laser system based on a correlation of the first image with the second image.

17. The method of claim 1, wherein the first image and the second image correspond to a first coordinate reference of an ancillary diagnostic device and a second coordinate reference of a laser treatment system, respectively, the method further comprising mapping a plurality of locations of the first image from first locations of the first coordinate reference to second locations of the second coordinate reference of the laser system based on a correlation of the first image with the second image.

18. The method of claim 1, wherein the first image of the eye and the second image of the eye comprise images of an iris of the eye and wherein one or more structures of the first image and the second image correspond to one or more structures of the iris.

19. The method of claim 1, further comprising applying a plurality of pulsed laser beams to locations of the eye to treat the eye, wherein the locations are determined in response to at least one of the first image, first shape profile, second image and second shape profile.

* * * * *